US010392161B2

(12) United States Patent
Berge

(10) Patent No.: US 10,392,161 B2
(45) Date of Patent: *Aug. 27, 2019

(54) CONTAINER ASSEMBLY WITH VENT

(71) Applicant: Silgan White Cap LLC, Downers Grove, IL (US)

(72) Inventor: Gary L. Berge, Crystal Lake, IL (US)

(73) Assignee: Silgan White Cap LLC, Downers Grove, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/983,848

(22) Filed: May 18, 2018

(65) Prior Publication Data
US 2018/0265259 A1 Sep. 20, 2018

Related U.S. Application Data

(63) Continuation of application No. PCT/US2016/016623, filed on Feb. 4, 2016.

(51) Int. Cl.
| B65D 33/01 | (2006.01) |
| A61L 2/00 | (2006.01) |
| B65D 75/58 | (2006.01) |
| B65D 41/04 | (2006.01) |
| B65D 41/34 | (2006.01) |

(Continued)

(52) U.S. Cl.
CPC ............. B65D 33/01 (2013.01); A61L 2/00 (2013.01); A61L 2/02 (2013.01); B65D 41/0485 (2013.01); B65D 41/3447 (2013.01); B65D 75/5883 (2013.01); C08L 101/00 (2013.01); A61L 2202/23 (2013.01); B65D 2213/00 (2013.01)

(58) Field of Classification Search
CPC .............. B65D 47/122; B65D 41/3428; B65D 75/008; B65D 75/5883; B65D 33/01; A61L 2/00
USPC ...... 222/92, 107; 383/80, 100–103, 904–907
See application file for complete search history.

(56) References Cited

U.S. PATENT DOCUMENTS

| D97,465 S | 11/1935 | Conner |
| 2,148,864 A | 2/1939 | Kistner |
(Continued)

FOREIGN PATENT DOCUMENTS

| DE | 296 09 596 U1 | 10/1996 |
| JP | 10181758 A | 7/1998 |
(Continued)

OTHER PUBLICATIONS

U.S. Appl. No. 29/472,406, filed Nov. 12, 2013, Taber et al.
(Continued)

Primary Examiner — Lien M Ngo
(74) Attorney, Agent, or Firm — Reinhart Boerner Van Deuren s.c.

(57) ABSTRACT

A container assembly including a pouch, spout and closure is provided. When the pouch and spout are attached, one or more cavities are formed between the inner surfaces of the sidewall of the pouch and the external surface of a mounting portion of the spout. One or both of the spout and pouch include a vent which provides for fluid communication between the cavity and the ambient environment on the outside of the pouch. The vents are configured to allow for pressure equalization of the cavity relative to the outside of the pouch during sterilization of the container assembly.

20 Claims, 40 Drawing Sheets

(51) Int. Cl.
  *C08L 101/00* (2006.01)
  *A61L 2/02* (2006.01)

(56) References Cited

U.S. PATENT DOCUMENTS

| | | |
|---|---|---|
| 3,463,341 A | 8/1969 | Fields |
| 4,305,516 A | 12/1981 | Perne et al. |
| D272,324 S | 1/1984 | Mumford et al. |
| D273,368 S | 4/1984 | Hayes |
| 4,503,986 A | 3/1985 | Nixdorff et al. |
| 4,505,401 A | 3/1985 | Berglund |
| D278,311 S | 4/1985 | Brown et al. |
| 4,573,601 A | 3/1986 | Berglund |
| 4,653,657 A | 3/1987 | Papavasilopoulos |
| 4,805,791 A | 2/1989 | Begley |
| 4,852,751 A | 8/1989 | Halfacre |
| 5,040,692 A | 8/1991 | Julian |
| 5,295,600 A | 3/1994 | Kowal |
| D359,683 S | 6/1995 | Beach et al. |
| D361,265 S | 10/1995 | Doxey |
| 5,810,184 A | 9/1998 | Adams et al. |
| 5,823,383 A | 10/1998 | Hins |
| 5,853,095 A | 12/1998 | Marshall et al. |
| 5,927,549 A | 7/1999 | Wood |
| 5,957,312 A | 9/1999 | Adams et al. |
| 6,050,451 A | 4/2000 | Hess, III et al. |
| 6,129,228 A | 10/2000 | Adams et al. |
| 6,131,806 A | 10/2000 | Hess, III et al. |
| D445,678 S | 7/2001 | Malmborg |
| 6,273,307 B1 | 8/2001 | Gross et al. |
| 6,330,959 B1 | 12/2001 | Dark |
| D454,066 S | 3/2002 | Trabal |
| D460,357 S | 7/2002 | Kras et al. |
| 6,439,429 B1 | 8/2002 | Gross |
| D467,501 S | 12/2002 | Tacchella |
| 6,557,714 B2 | 5/2003 | Babcock et al. |
| D476,565 S | 7/2003 | Rosen |
| 6,612,466 B1 | 9/2003 | Malin |
| D489,978 S | 5/2004 | Brown |
| 6,783,014 B2 | 8/2004 | Luker |
| 6,811,047 B1 | 11/2004 | Hicks et al. |
| 6,860,406 B2 | 3/2005 | Kobetsky et al. |
| 6,958,033 B1 | 10/2005 | Malin |
| D542,654 S | 5/2007 | Szczesniak |
| D542,655 S | 5/2007 | Szczesniak |
| D542,656 S | 5/2007 | Szczesniak |
| D544,348 S | 6/2007 | Szczesniak |
| D547,657 S | 7/2007 | Tacchella |
| D551,975 S | 10/2007 | Gornoll et al. |
| D552,483 S | 10/2007 | Rigardo |
| D564,884 S | 3/2008 | Rittman |
| D574,241 S | 8/2008 | Braukmann et al. |
| D579,332 S | 10/2008 | Krivoshein |
| 7,677,422 B2 | 3/2010 | Lee |
| 7,735,666 B2 | 6/2010 | Niwa et al. |
| 7,753,233 B2 | 7/2010 | Umenaka |
| D631,349 S | 1/2011 | Arnell et al. |
| 7,882,977 B2 | 2/2011 | Johnson |
| D633,386 S | 3/2011 | Taber et al. |
| D634,199 S | 3/2011 | Taber et al. |
| D634,200 S | 3/2011 | Taber et al. |
| D646,263 S | 10/2011 | Yuan et al. |
| 8,105,226 B2 | 1/2012 | Wada |
| D661,185 S | 6/2012 | Battat |
| 8,231,020 B2 | 7/2012 | Taber et al. |
| 8,231,025 B2 | 7/2012 | Johnson |
| D671,187 S | 11/2012 | Saringer |
| D672,238 S | 12/2012 | Aziz et al. |
| D672,241 S | 12/2012 | Sawicki et al. |
| D679,590 S | 4/2013 | Stull et al. |
| D679,597 S | 4/2013 | Tamarindo |
| D682,688 S | 5/2013 | Murray |
| 8,443,999 B1 | 5/2013 | Reinders |
| D684,055 S | 6/2013 | Kwon |
| D684,056 S | 6/2013 | Kwon |
| D684,057 S | 6/2013 | Kwon |
| D684,058 S | 6/2013 | Kwon |
| 8,468,635 B2 | 6/2013 | Nikitczuk et al. |
| D686,495 S | 7/2013 | Murray |
| 8,528,757 B2 | 9/2013 | Bisio |
| 8,528,758 B2 | 9/2013 | Morlot et al. |
| D693,220 S | 11/2013 | Luo |
| 8,613,548 B2 | 12/2013 | Murray |
| 8,616,394 B2 | 12/2013 | Kim |
| 8,695,819 B1 | 4/2014 | Anderson |
| D705,061 S | 5/2014 | Jo et al. |
| D705,062 S | 5/2014 | Jo et al. |
| D710,772 S | 8/2014 | Maiorana et al. |
| 8,807,361 B2 | 8/2014 | Luo |
| D712,266 S | 9/2014 | Romer et al. |
| D712,743 S | 9/2014 | Neputy et al. |
| D712,744 S | 9/2014 | Neputy et al. |
| 8,950,939 B2 | 2/2015 | Last et al. |
| 9,309,032 B2 | 4/2016 | Berge et al. |
| D756,777 S | 5/2016 | Berge et al. |
| D760,081 S | 6/2016 | Berge |
| 9,533,802 B2 | 1/2017 | Berge |
| D790,344 S | 6/2017 | Neputy et al. |
| 2004/0200797 A1 | 10/2004 | Hicks et al. |
| 2004/0245286 A1 | 12/2004 | Kobetsky et al. |
| 2005/0011911 A1 | 1/2005 | Vaughan |
| 2005/0040181 A1 | 2/2005 | Kurosawa et al. |
| 2005/0139607 A1 | 6/2005 | Kobetsky et al. |
| 2005/0205438 A1 | 9/2005 | Hierzer et al. |
| 2006/0062497 A1 | 3/2006 | Murray |
| 2007/0110344 A1 | 5/2007 | Murray |
| 2008/0124432 A1 | 5/2008 | Ma |
| 2008/0135513 A1 | 6/2008 | Umenaka |
| 2009/0223963 A1 | 9/2009 | Bisio |
| 2010/0213213 A1 | 8/2010 | Albers et al. |
| 2011/0210122 A1 | 9/2011 | Benoit-Gonin et al. |
| 2012/0024858 A1* | 2/2012 | Sholes ............... B65D 47/243 220/367.1 |
| 2012/0211460 A1 | 8/2012 | Tamarindo |
| 2012/0325769 A1 | 12/2012 | Essebaggers et al. |
| 2013/0270270 A1 | 10/2013 | Reinders |
| 2014/0010481 A1 | 1/2014 | Last et al. |
| 2014/0048536 A1 | 2/2014 | Bisio |
| 2014/0263475 A1 | 9/2014 | Totten |
| 2015/0129533 A1 | 5/2015 | Taber et al. |
| 2015/0232237 A1 | 8/2015 | Berge et al. |
| 2016/0122095 A1 | 5/2016 | Berge |
| 2017/0319001 A1* | 11/2017 | Butscher ............... A47J 31/407 |

FOREIGN PATENT DOCUMENTS

| | | |
|---|---|---|
| JP | 10258850 | 9/1998 |
| JP | 2002104447 A | 4/2002 |
| JP | 2005-082193 | 3/2005 |
| JP | 2011246128 A | 12/2011 |
| JP | 2014-019447 | 2/2014 |
| KR | 20020024043 | 3/2002 |
| KR | 20090041946 | 4/2009 |
| KR | 200455090 | 8/2011 |
| KR | 200466355 | 4/2013 |
| WO | WO 20041045977 A1 | 6/2004 |
| WO | WO 2008/050361 A1 | 5/2008 |

OTHER PUBLICATIONS

International Searching Authority, "International Search Report," issued in connection with International Application No. PCT/US2016/016623, dated Oct. 27, 2016, 3 pages.

International Searching Authority, "Written Opinion," issued in connection with International Application No. PCT/US2016/016623, dated Oct. 27, 2016, 10 pages.

International Searching Authority, "International Search Report and Written Opinion," issued in connection with International Patent Application No. PCT/US2015/015241, dated May 21, 2015, 8 pages.

Silgan White Cap, "Secure-Spout—9mm Spout with Fitment" Brochure, believed to be publically available on Jun. 11, 2014 and

(56) References Cited

OTHER PUBLICATIONS representative of closure and spout believed to be publically available on Jun. 11, 2014, 3 pages.
Flexible Packaging, "Silgan White Cap to Introduce Secure-Spout Pouch Technology at Global Pouch Forum," published on Jun. 1, 2014, accessed online on Nov. 18, 2015, [URL:http://www.flexpackmag.com/keywords/4416-silgan-white-cap], 2 pages.
Images of Spouts and Closures, document believed to be publicly available at least by Aug. 2012, 1 page.
Gualapack System, Image of Spouts and Caps, accessed online on Apr. 1, 2013, [URL:http://www.gualapack.com/img/pagine/prodotti/tappi/1.jpg], believed to be publicly available from Gualapack System at least by Aug. 2012, 1 page.
Gualapack System, Image of first stacked caps, accessed online on Apr. 1, 2013, [URL:http://www.gualapack.com/img/pagine/prodotti/innovazione/1.jpg], believed to be publicly available from Gualapack System at least by Aug. 2012, 1 page.
Gualapack System, Image of second stack caps, accessed online on Apr. 1, 2013, [URL:http://www.gualapack.com/img/pagine/prodotti/innovazione/2.jpg], believed to be publicly available from Gualapack System at least by Aug. 2012, 1 page.
Gualapack System, Image of third stacked caps, accessed online on Apr. 1, 2013, [URL:http://www.gualapack.com/img/pagine/prodotti/innovazione/3.jpg], believed to be publicly available from Gualapack System at least by Aug. 2012, 1 page.
International Searching Authority, "International Search Report and Written Opinion," issued in connection with PCT/US2015/056238, dated Dec. 30, 2015, 9 pages.
International Bureau, "International Preliminary Report on Patentability," issued in connection with International Application No. PCT/US2016/016623, dated Aug. 16, 2018, 12 pages.

\* cited by examiner

US 10,392,161 B2

1

CONTAINER ASSEMBLY WITH VENT

CROSS-REFERENCE TO RELATED PATENT APPLICATION

The present application claims the benefit of and priority to International Application No. PCT/US2016/016623, filed on Feb. 4, 2016, which is incorporated herein by reference in its entirety.

BACKGROUND OF THE INVENTION

The present invention relates to a container assembly including a vent. Specifically, the container assembly includes a pouch which holds a material having a liquid or gel-like consistency, a closure, and a spout. When the pouch and spout are sealed together, cavities are formed between the external surface of the spout and the inner surfaces of the sidewalls of the pouch. One or both of the spout and pouch include one or more vents that allows for fluid communication between cavities and the outside of the pouch.

SUMMARY OF THE INVENTION

In one embodiment, a container comprises a pouch formed from a plastic material to define an interior for containing a substance and an open end into which the substance may be placed from the outside of the pouch. The container also includes a fitment including a fluid-tight wall defining a flow channel through which the substance may flow with respect to the interior of the pouch.

A sealing formation which is joined to the fitment and sealed to the material at the open end of the pouch with a fluid-tight seal forms a fluid-tight interface between the open end of the pouch and the fitment. A support formation which joins the fitment to the open end supports the fitment relative to the open end such that the fitment, sealing formation, support formation and pouch material form a cavity at the interface.

A vent, in one of the support formation and the pouch material which forms the cavity, provides a fluid passage between the cavity and outside of the pouch such that when the pressure of a fluid surrounding the pouch is changed, the vent permits the fluid to flow relative to the cavity to equalize the pressure within the cavity and at the outside of the pouch.

In another embodiment, a fitment for a pouch is formed from a plastic material to define an interior for containing a substance and an open end into which the substance may be placed from the outside of the pouch. The fitment comprises a wall having an exterior surface and an interior surface defining a flow channel extending between a first opening and a second opening. The fitment also comprises a sealing formation formed on the exterior surface and sealable to the material at the open end of the pouch with a fluid-tight seal to form a fluid-tight interface between the open end of the pouch and the wall.

A support formation is formed on the exterior surface and joinable to the open end to form a cavity between the wall, sealing formation, support formation and pouch material. A vent in the support formation provides a fluid passage between the cavity and outside of the pouch such that when the pressure of a fluid surrounding the pouch is changed, the vent permits the fluid to flow relative to the cavity to equalize the pressure within the cavity and at the outside of the pouch.

2

In one embodiment, a method for sterilizing the contents of a container assembly is disclosed. A container assembly including a pouch, a spout, and a closure is provided. The spout includes a flow channel through which the contents may flow from the interior of the pouch to a location outside the pouch. The spout also includes a bottom sealing wall surrounding the flow channel, the outer perimeter of the bottom wall configured for forming a fluid-tight interface with the inner surface of the sidewall of the pouch when the pouch and spout are sealed. The contents of the pouch are only accessible to a location outside the pouch through the flow channel when the pouch and spout are sealed together. The spout also includes one or more ribs extending radially outwardly from the flow channel. The ribs are located above the bottom sealing wall.

The spout is sealed to the pouch to form a fluid-tight interface. When the pouch and spout are sealed together, one or more cavities are formed. Each cavity is bounded in its entirety by the inner surface of the sidewall of the pouch and the outer surface of the spout.

Vents are provided in one of the spout and the pouch. The vents provide fluid communication between each cavity and the outside of the pouch. The contents of the container assembly are sterilized after the spout, pouch and closure have been assembled.

BRIEF DESCRIPTION OF THE DRAWINGS

This application will become more fully understood from the following detailed description, taken in conjunction with the accompanying figures, wherein like reference numerals refer to like elements in which.

DETAILED DESCRIPTION

Figure 1:
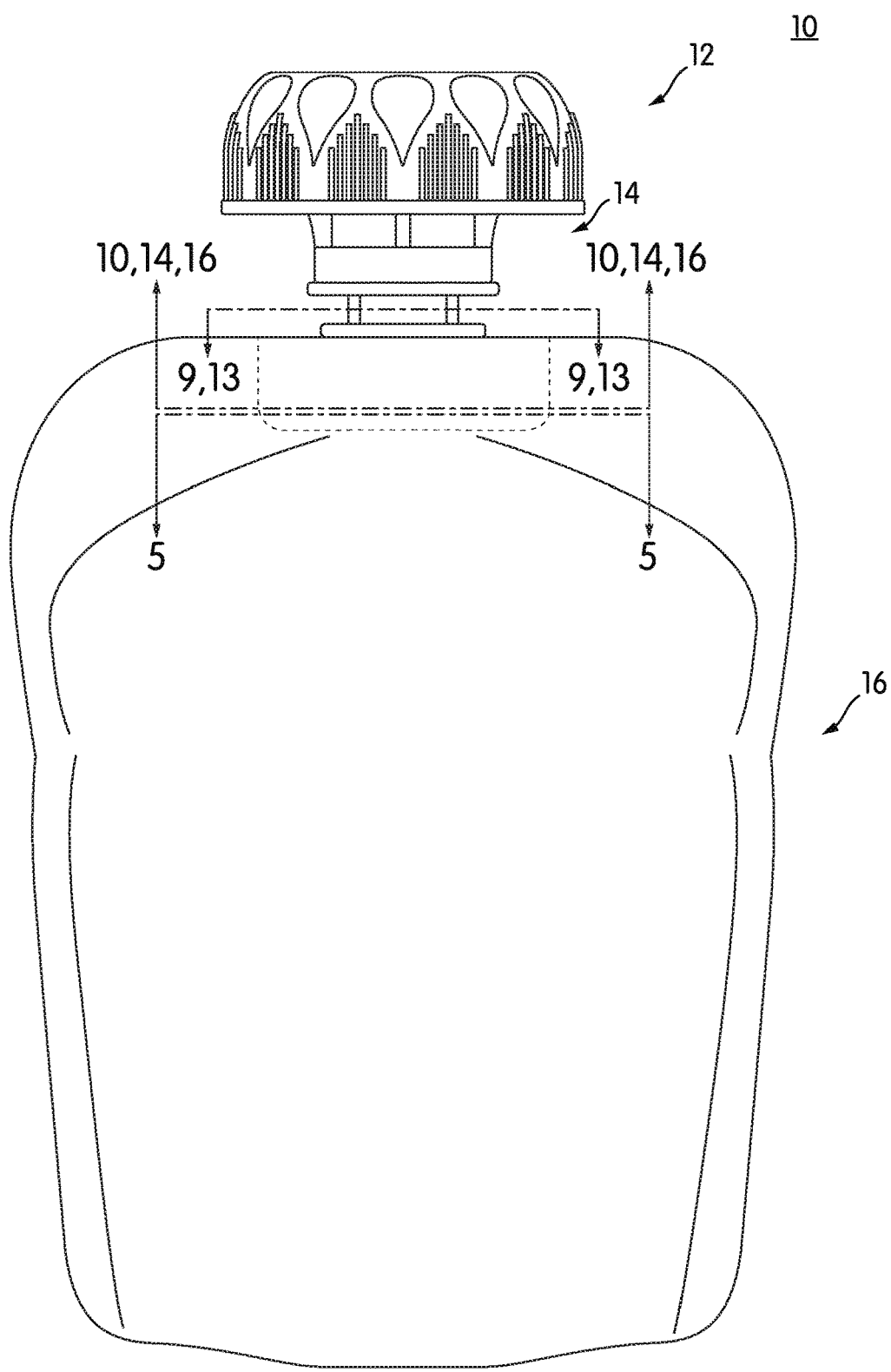
FIG. 1 shows a container assembly according to one embodiment.

Referring generally to the figures, various embodiments of a container assembly including a pouch, closure and related spout are described. The spout and/or pouch includes one or more vents that provide for fluid communication between the ambient environment and internal spaces formed between the pouch and the spout to allow for pressure within the internal spaces to equalize with respect to the ambient environment.

In some embodiments, the closure has an inner wall enclosed by an end wall with an internal thread on the inner surface of the inner wall. The closure may include a sealing rim that extends down from the inner surface of the end wall. The inner wall is radially surrounded by an outer sidewall, with a passage between the inner wall and the outer sidewall that allows airflow through the closure. In some embodiments, the closure includes a tamper indicating band, also referred to as a tamper band or safety band. The tamper band or safety band is configured to provide a visual indication to the end user that the closure has not been opened since being sealed by the manufacturer.

The tamper band, which in one embodiment is a ring or loop of material located below the end of the inner wall, is attached to the inner wall of the closure with hinge connectors and frangible connectors. The tamper band includes an internal surface having an internal rim or rib that interacts with the spout to permanently deform the tamper band upon removal of the closure by a user. Specifically, upon movement of the closure relative to the spout, the elements of the tamper band engage with the elements of the spout, and further movement of the closure causes the frangible connectors to break. As a result, the tamper band is broken and displaced, providing the visual indication to a user that the closure is opened while at the same time keeping the broken tamper band secured to the closure. Compared to at least some conventional tamper bands, the tamper bands discussed herein are configured to provide increased visibility after the closure is opened. Specifically, as discussed in more detail below, the tamper band not only includes break points of connection with the main portion of the closure, but also includes hinge connections which allow the tamper band to rotate outward, increasing the visibility of the broken tamper band.

In addition, the closure and the tamper band discussed herein may be particularly suitable for containers, for example food or drink containers, intended for use by children. For example, because the tamper band remains attached to the closure after the container is opened, the likelihood that the tamper band is accidentally swallowed by a user may be reduced. For example, because the tamper band is removed along with the removal of the closure, it does not remain near the opening of the container where a user may place their mouth. In addition, in contrast to many single walled closures, the closure embodiments discussed herein include inner and outer walls separated by a space that allows passage of air through the closure. This configuration may allow a user to breath and seek medical attention if the closure becomes lodged in the airway of a user.

Before turning to the figures, which illustrate the embodiments in detail, it should be understood that the present application is not limited to the details or methodology set forth in the description or illustrated in the figures. It should also be understood that the terminology is for the purpose of description only and should not be regarded as limiting.

Referring generally to the figures, in various embodiments, a container assembly includes a pouch and a container closure assembly that includes a closure that is molded and a separately molded spout having a plastic neck finish are provided. In general the closure is attached to the spout via an engagement structure, such as threading. The closure includes an integral tamper band that, upon removal interacts with the spout to both break the tamper band and to push the broken tamper band outward enhancing the visibility/detectability of the broken tamper band. The spout and/or the pouch includes one or more vents to allow equalization of pressure located between the spout and pouch and the outside environment. In addition, the spout includes a structure located at the lower, input end of the spout that acts to limit or prevent flexible sidewalls of the pouch from occluding the input end of the spout, that may otherwise occur as the contents of the pouch are being consumed through the spout.

FIG. 1 shows a container assembly 10 according to an embodiment. Container assembly 10 includes a container, shown as pouch 16 and a closure assembly, including a closure 12 and a spout 14. Spout 14 is coupled to pouch 16. In general, pouch 16 includes container contents, such as liquid, semi-liquid, or powdered food or beverage, within pouch 16, and spout 14 provides a channel through which the contents of pouch 16 can be accessed. In the embodiment shown, pouch 16 is a flexible, squeezable type of container, which may be formed from a flexible material. In various embodiments, the flexible material may be a material such as a thermoplastic sheet or a foil pouch. In other embodiments, closure 12 and spout 14 may be used in conjunction with other types of containers, such as plastic bottles, composite (paper, cardboard, etc.) boxes, or pouches fabricated from suitable laminated materials. In specific embodiments, the contents of pouch 16 may be food or beverage intend for consumption by a child, such as baby food, yogurt, apple sauce, etc.

The spout 14 may be assembled with the closure 12 before insertion into the pouch 16 that has been prefilled with contents, or the spout 14 may be inserted into an empty pouch 16 that is then filled with contents through the spout 14, after which the closure 12 is added to the spout 14.

As shown in FIG. 1, spout 14 is coupled to pouch 16 adjacent to the upper end of pouch 16. In this arrangement, spout 14 protrudes from the upper end of pouch 16, and closure 12 acts to seal spout 14. As will be generally understood, the lower end of pouch 16 may provide an end wall or rim providing a stable base for pouch 16 to sit in the upright position shown in FIG. 1.

Figure 2:
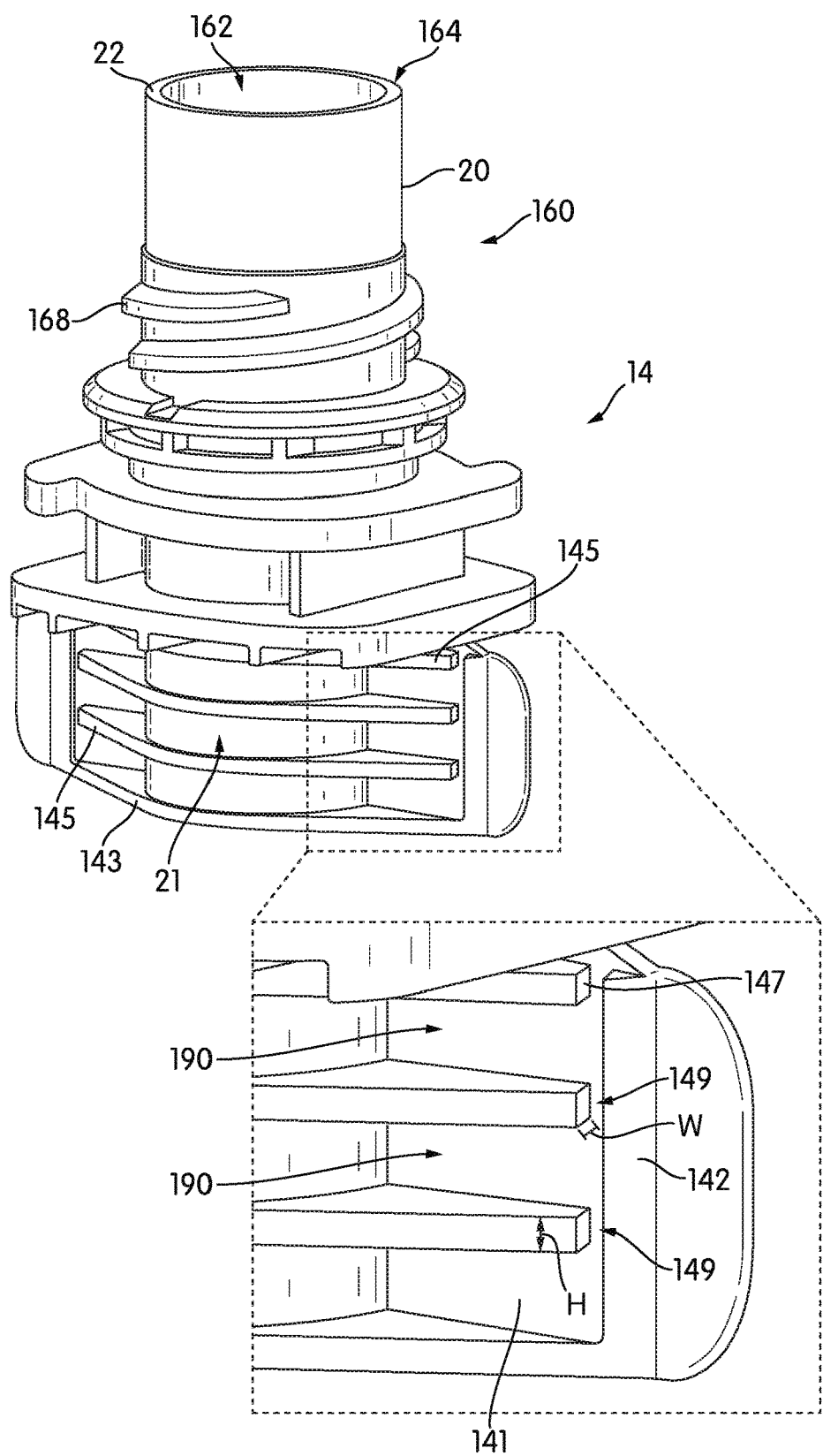
FIG. 2 is a perspective view of a spout including a mounting portion having a vent according to one embodiment.

Referring to FIG. 2, spout 14 according to one embodiment in shown. As shown in FIG. 2, spout 14 includes a tube 20 extending about the longitudinal axis of the spout 14 and defining a central channel 162 that extends through spout 14 from an input or inlet opening 164 to an output or outlet opening 166. In general, central channel 162 provides a pathway from the interior of a container (such as pouch 16) to the exterior of the container through which container contents can be accessed and removed. An upper spout portion 160 includes a closure engagement structure, shown as threads 168 that engage cooperating threads of closure 12.

Below threads 168, the spout 14 may include one or more annular flanges that extend radially out from the exterior surface of the tube 20. As shown in FIG. 2, in one embodiment spout 14 includes an upper flange 15, a middle flange 17, and a lower flange 19.

Figure 3:
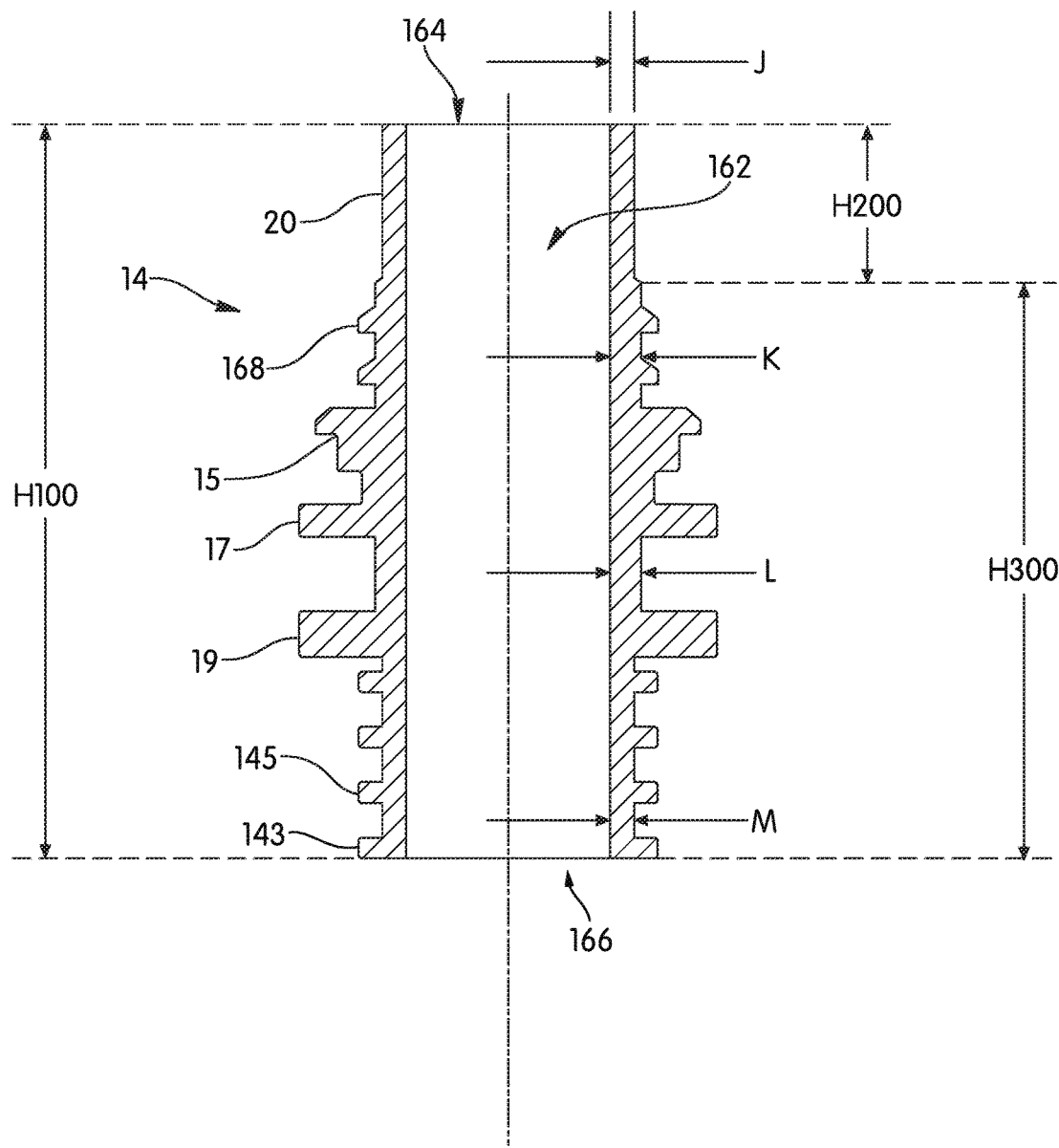
FIG. 3 is a cross-sectional view of the spout of FIG. 2 according to one embodiment.

Referring to FIG. 3, in various embodiments, spout 14 is molded from plastic and has thicknesses along the length of spout 14 that facilitates accurate molding of spout 14. As shown in FIG. 3, upper spout portion 160 has a thickness J and a height H200. In various embodiments, upper spout portion 160 has a thickness J between 0.025 inches and 0.040 inches, specifically between 0.028 inches and 0.032 inches, and more specifically about 0.030 inches (e.g., plus or minus 0.005 inches). In various embodiments, spout 14 has a total height H100, and H200 is less than 30% of H100 and more specifically is less than 25% of H100. In addition, spout 14 has a thickness K located between threads 168, and in various embodiments, thickness K is between 0.035 inches and 0.045 inches, specifically between 0.038 inches and 0.042 inches, and more specifically about 0.040 inches (e.g., plus or minus 0.005 inches). Spout 14 has a thickness L located between flanges 17 and 19, and in various embodiments, thickness L is between 0.038 inches and 0.048 inches, specifically between 0.041 inches and 0.045 inches, and more specifically about 0.043 inches (e.g., plus or minus 0.005 inches). Spout 14 has a thickness M located between ribs 145, and in various embodiments, thickness M is between 0.038 inches and 0.048 inches, specifically between 0.041 inches and 0.045 inches, and more specifically about 0.043 inches (e.g., plus or minus 0.005 inches). In various embodiments, the areas having thicknesses K, L and M have a height shown as H300, and in various embodiments, H300 is greater than 60% of H100, and more specifically greater than 70% of H100.

Spout 14 also includes a mounting portion 140. Referring to FIG. 2, a mounting portion 140 according to one embodiment is shown. As seen in FIG. 2, mounting portion 140 surrounds a lower portion 21 of tube 20. In some embodiments, mounting portion 140 may have a generally trapezoidal shape, e.g. a rhomboid shape, with rounded vertices. As shown in FIG. 2, the mounting portion 140 includes wings 28 having generally flat planar portions located at diametrically opposite ends of the mounting portion 140. The wings 28 are configured to form a fluid-tight interface with the pouch 16 when the pouch 16 is attached to the wings 28. In other embodiments, the mounting portion 140 may include other structures such as additional flanges, rings, etc., instead of wings 28 that allow for coupling to and support of the spout 14 to the pouch 16.

When the spout 14 is attached to the pouch 16, the wings 28 extend within the pouch 16 and are attached to the inner surfaces of the sidewalls of the pouch 16, such that spout 14 is supported from the pouch 16 as shown in FIG. 1. The fluid-tight attachment or bonding between the pouch 16 and the wings 28 may involve an adhesive, a melted thermoplastic, heat welding, ultrasonic welding, or other means for sealing the structures together.

Figure 4:
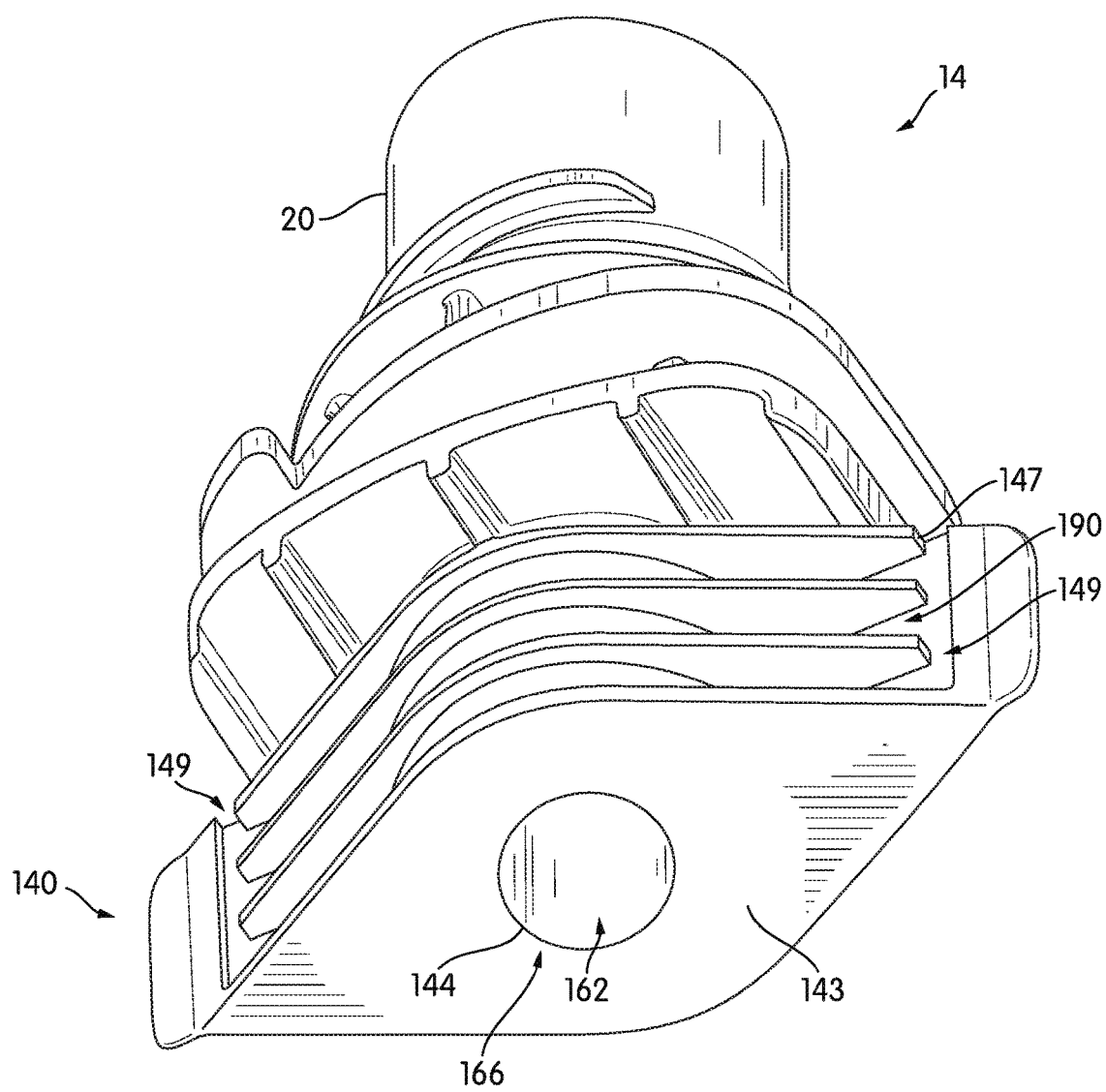
FIG. 4 is bottom perspective view of the spout of FIG. 2 according to one embodiment.

As shown in FIG. 4, mounting portion 140 includes a bottom sealing wall 143 including an opening 144. Opening 144 of the bottom sealing wall 143 provides for fluid communication between the contents stored in the cavity of pouch 16 and the central channel 162 of spout 14.

Figure 5:
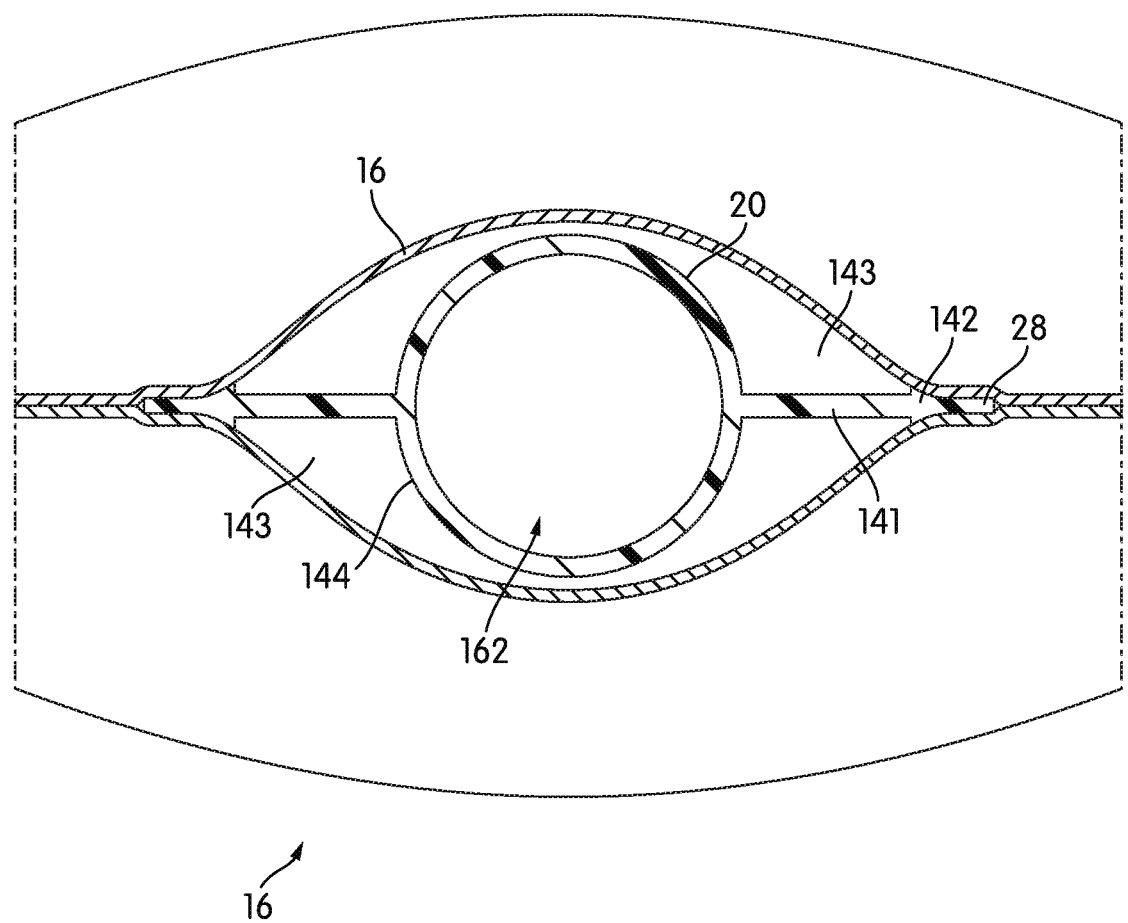
FIG. 5 is a bottom sectional view from above taken along line 5-5 of FIG. 1 according to one embodiment
Figure 6:
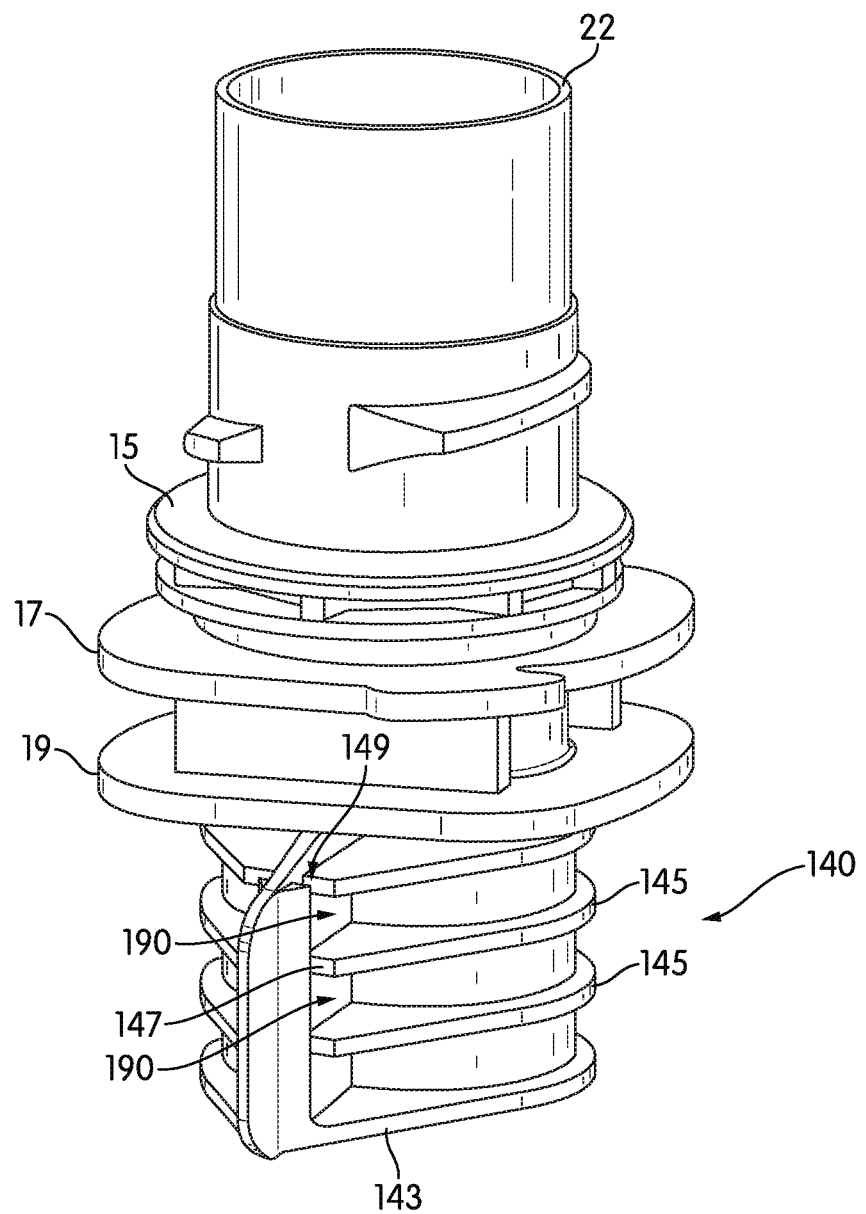
FIG. 6 is a perspective view of the spout of FIG. 2 according to one embodiment.
Figure 7:
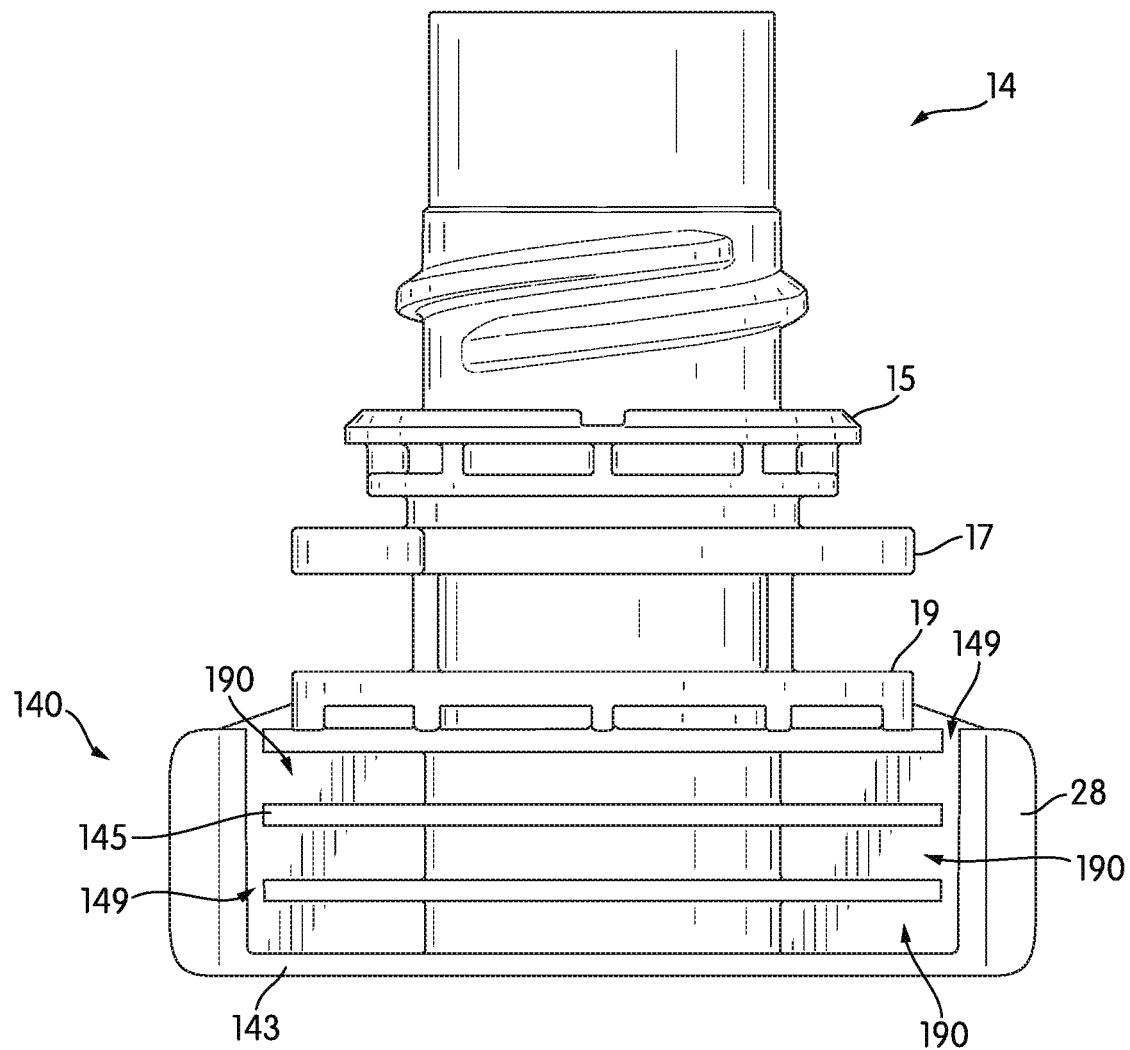
FIG. 7 is a front view of the spout of FIG. 2 according to one embodiment.

Referring to FIG. 5, a bottom sectional view taken along line 5-5 of FIG. 1 is shown. Line 5-5 of FIG. 1 extends along a plane located between and extending parallel to the upper surface of bottom sealing wall 143 and the bottom surface of the bottommost rib 145 located directly above bottom sealing wall 143. As shown in FIG. 5, the perimeter of bottom sealing wall 143 extends uninterruptedly between the diametrically opposed wings 28 such that when spout 14 is attached to pouch 16, the perimeter of bottom sealing wall 143 forms an uninterrupted fluid-tight interface with pouch 16. This fluid-tight attachment or bonding between the pouch 16 and the bottom sealing wall 143 may involve an adhesive, a melted thermoplastic, heat welding, ultrasonic welding, or other means for sealing the structures together.

As also shown in FIG. 5, with the exception of opening 144, the bottom sealing wall 143 forms a solid surface free of any gaps or holes extending from a top surface of bottom sealing wall 143 to a bottom surface of bottom sealing wall 143. The interface between the opening 144 and the tube 20 extending through the bottom sealing wall 143 is a fluid tight interface which may involve an adhesive, a melted thermoplastic, heat welding, ultrasonic welding, or other means for sealing the structures together. Alternatively, the tube 20 and bottom sealing wall 143 may be monolithically molded. As such, bottom sealing wall 143 is configured such that when the spout 14 is sealed to pouch 16, the only fluid communication between the contents in the cavity of pouch 16 and the external environment is through the central channel 162.

Referring to FIG. 2, mounting portion 140 further includes one or more ribs 145 circumferentially extending about lower portion 21 of tube 20. In some embodiments, mounting portion 140 also includes a support wall 141 extending between wings 28. As shown in FIG. 2, ribs 145 extend perpendicularly outward from the front and back surfaces of support wall 141. In other embodiments, mounting portion 140 may be formed without a support wall 141, and each rib 145 may include a single flange circumferentially surrounding and extending radially from tube 20. In such embodiments of a mounting portion 140 formed without a support wall 141, wings 28 may be integrated into the structure of the mounting portion 140 by extending wings 28 from the ends of bottom sealing wall 143.

As shown in FIG. 2, ribs 145 have a maximum diameter (as measured between the rounded vertices of mounting portion 140) no greater than the maximum diameter (as also measured between the rounded vertices of mounting portion 140) of bottom sealing wall 143. The contour of the perimeter of ribs 145 generally mirrors the contour of the perimeter of bottom sealing wall 143. When the pouch 16 and spout 14 are attached, the outer perimeter of the ribs 145 is configured to form a fluid fluid-tight attachment or bonding with the inner sidewall of the pouch 16. This fluid tight attachment may involve an adhesive, a melted thermoplastic, heat welding, ultrasonic welding, or other means for sealing the structures together.

When the mounting portion 140, including ribs 145, is sealed, bonded, or otherwise attached to pouch 16, air may become trapped between the spaces 190 defined between adjacent ribs 145 and/or between the bottommost rib 145 and the bottom sealing wall 143. As the ambient temperature and/or pressure in which the assembled pouch 16 and spout 14 assembly are stored changes or fluctuates, the pressure within spaces 190 and/or the volume of the air trapped in spaces 190 may also change. These changes in ambient pressure and/or temperature may occur unintentionally, for example during storage or transport. In other embodiments, the changes in ambient pressure and/or temperature may be imparted intentionally, e.g. during preservation of sterilization procedures. For example, a container assembly 10 undergoing high pressure processing (HPP) or pascalization would undergo extreme changes in ambient pressure.

As a result of fluctuating or changing pressures and/or volumes occurring relative to spaces 190, forces may be imparted on the attachments between the spout 14 and pouch 16 formed at the interfaces between the mounting portion 140 and the inner surfaces of the sidewalls of the pouch 16 (e.g. between the interface of the wings 28 and pouch 16, between the interface of the bottom sealing wall 143 and pouch, between the interface of the ribs 145 and the pouch 16, etc.) In turn, these resultant forces may act to affect or impair the fluid-tight sealing engagement formed between the pouch 16 and the mounting portion 140 of spout 14.

Referring to FIGS. 2-22, various embodiments of a container assembly 10 incorporating one or more vents are shown. These vents, as shown in the illustrative embodiments, are configured to provide fluid communication between the outside of the cavities extending between and bounded by the inner surfaces of the sidewalls of pouch 16 and the external surfaces of the mounting portion 140, such as, e.g. spaces 190. By providing a path for air to travel between spaces 190 and the ambient environment, the internal pressure within spaces 190 may be equalized with the pressure external to the container assembly 10. By allowing for the pressure inside the spaces 190 to be substantially the same as the pressure external to the container assembly 10, forces may be prevented from acting upon and adversely affecting the fluid tight seal of the attachment between the pouch 16 and mounting portion 140.

Referring to FIGS. 2-10, one embodiment of a spout 14 incorporating a vent is shown. As shown in FIG. 2, the shape, size and configuration of ribs 145 generally mirrors the shape, size and configuration of bottom sealing wall 143. However, whereas the bottom sealing wall 143 extends from one wing 28 to opposite wing 28, the ends of ribs 145 are cut short, creating a gap 149 between end portions 147 of ribs 145 and the wings 28. Because the ribs 145 are cut short, end portions 147 are defined by a rectangular faces having a height H and width W.

Figure 8:
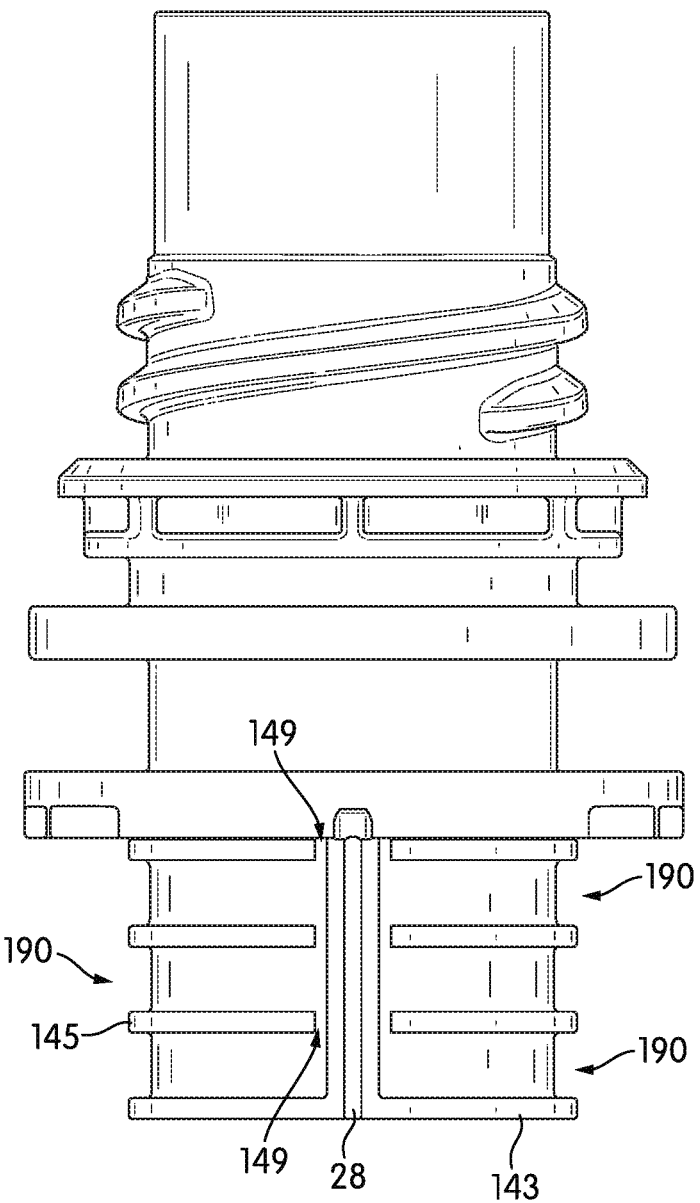
FIG. 8 is a side view of the spout of FIG. 2 according to one embodiment.
Figure 9:
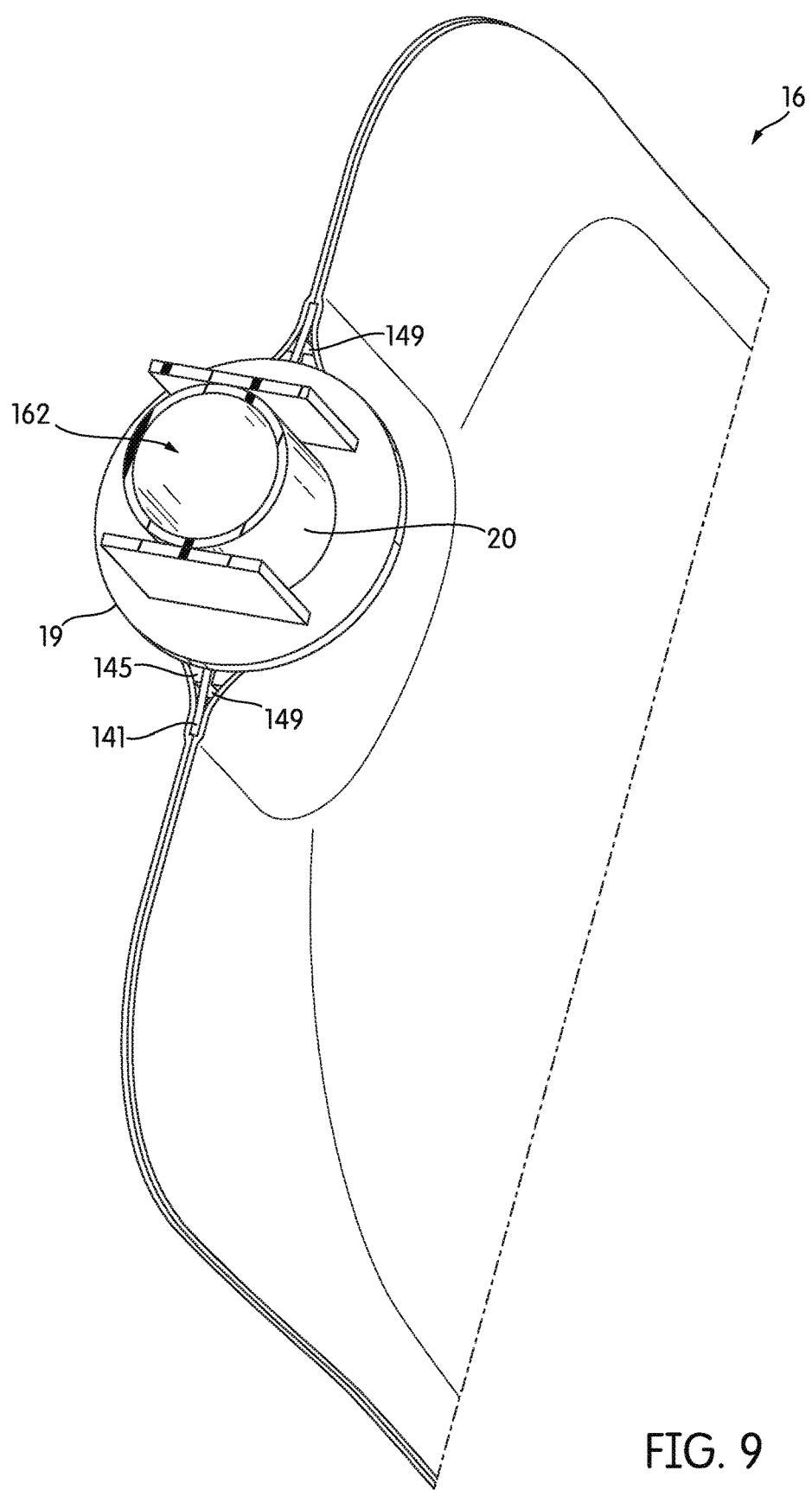
FIG. 9 is a perspective view from above of the spout of FIG. 2 sealed to the pouch-type container of FIG. 1 according to one embodiment.
Figure 10:
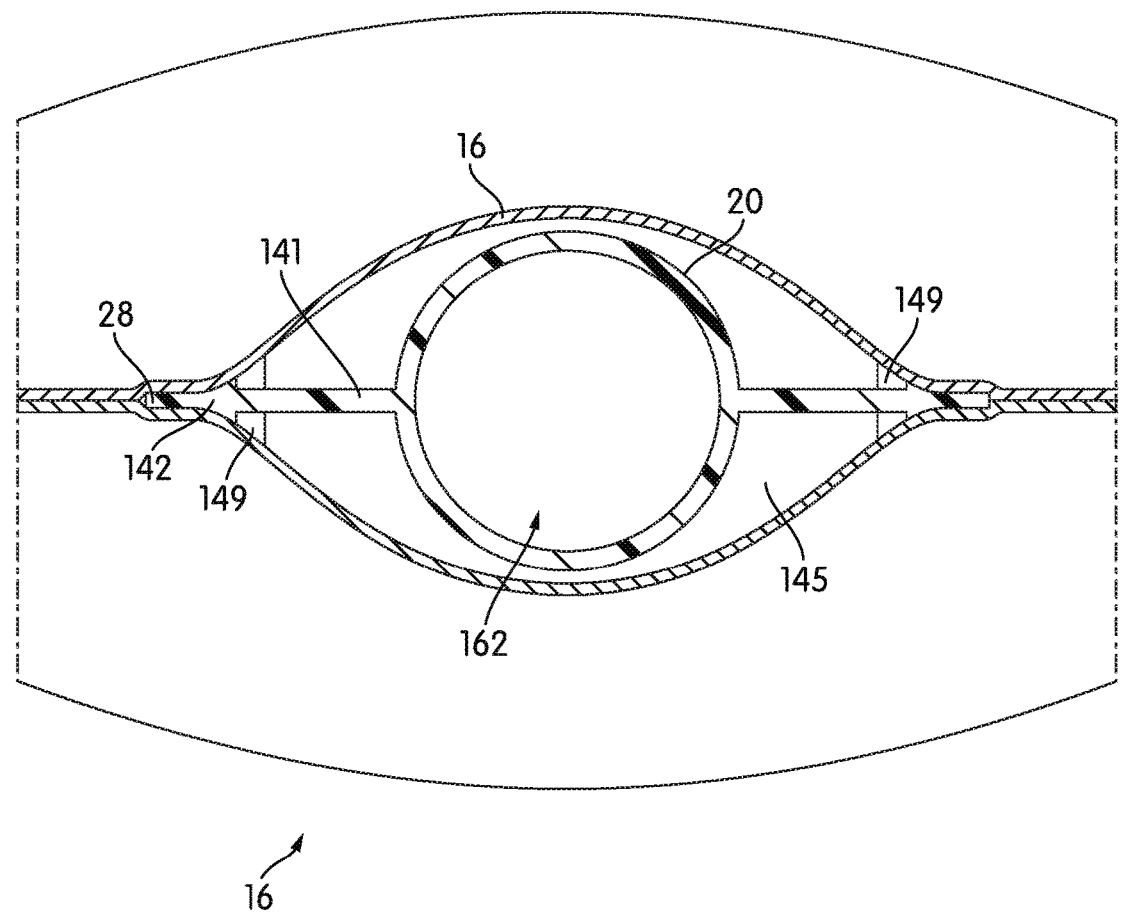
FIG. 10 is a top sectional view taken along line 10-10 of FIG. 1 according to one embodiment.

As shown in FIGS. 8-10, when the pouch 16 and spout 14 are attached, gaps 149 define vents through which the spaces 190 are in fluid communication with the outside environment. As shown in FIGS. 4, 5 and 10, wings 28 may optionally include a transition portion 142 that extends along a curve from the flat portion of wings 28. The outer perimeters of ribs 145 are configured to form a fluid-tight interface with the pouch 16 when the pouch 16 is attached to the ribs 145 of mounting portion 140. This fluid-tight attachment or bonding between the pouch 16 and the ribs 145 may involve an adhesive, a melted thermoplastic, heat welding, ultrasonic welding, or other means for sealing the structures together. As shown in FIG. 10, the outer perimeter of each rib 145 is configured to form an uninterrupted fluid-tight interface along the entire length of each rib 145 with the inner surfaces of the sidewalls of pouch 16 when the pouch 16 and spout 14 are attached. The structure of the end portions 147 and the curve of the transition portion 142 are configured such that when the pouch 16 and spout 14 are sealed together, the pouch 16 lays taut against the outer perimeter of the mounting portion 140 and the pouch is prevented from occluding gaps 149.

Figure 11:
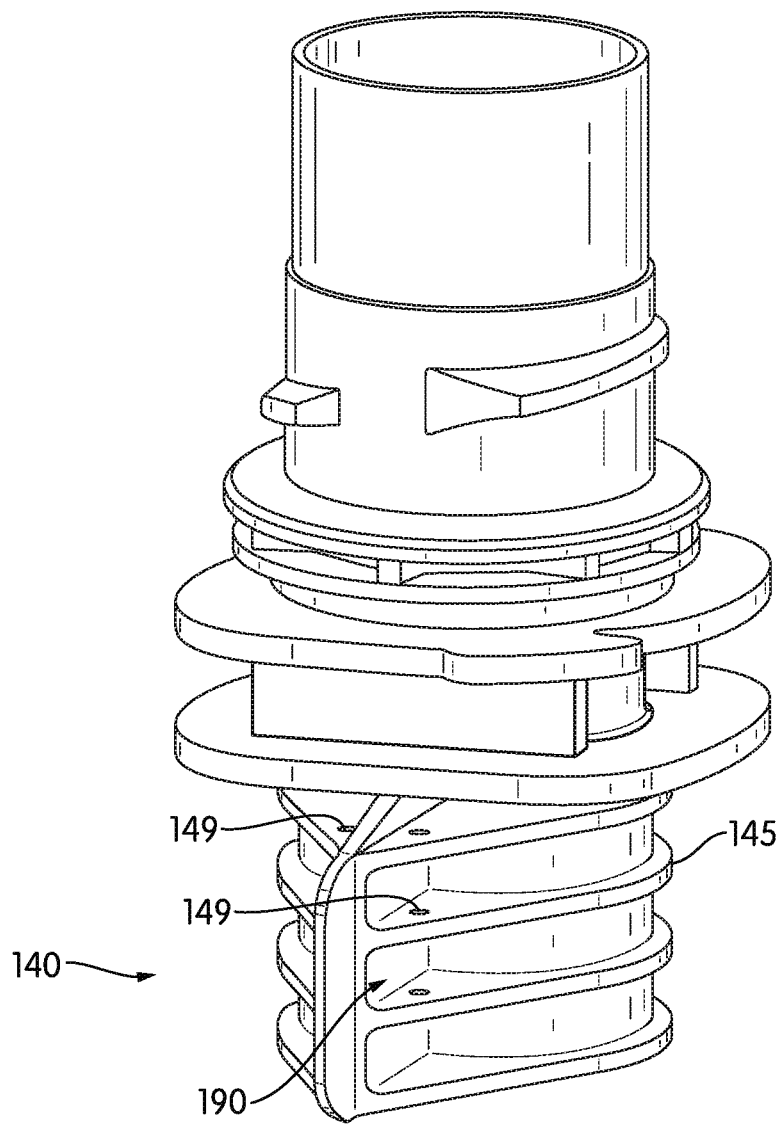
FIG. 11 is a perspective view of a spout including a mounting portion having a vent according to one embodiment.
Figure 14:
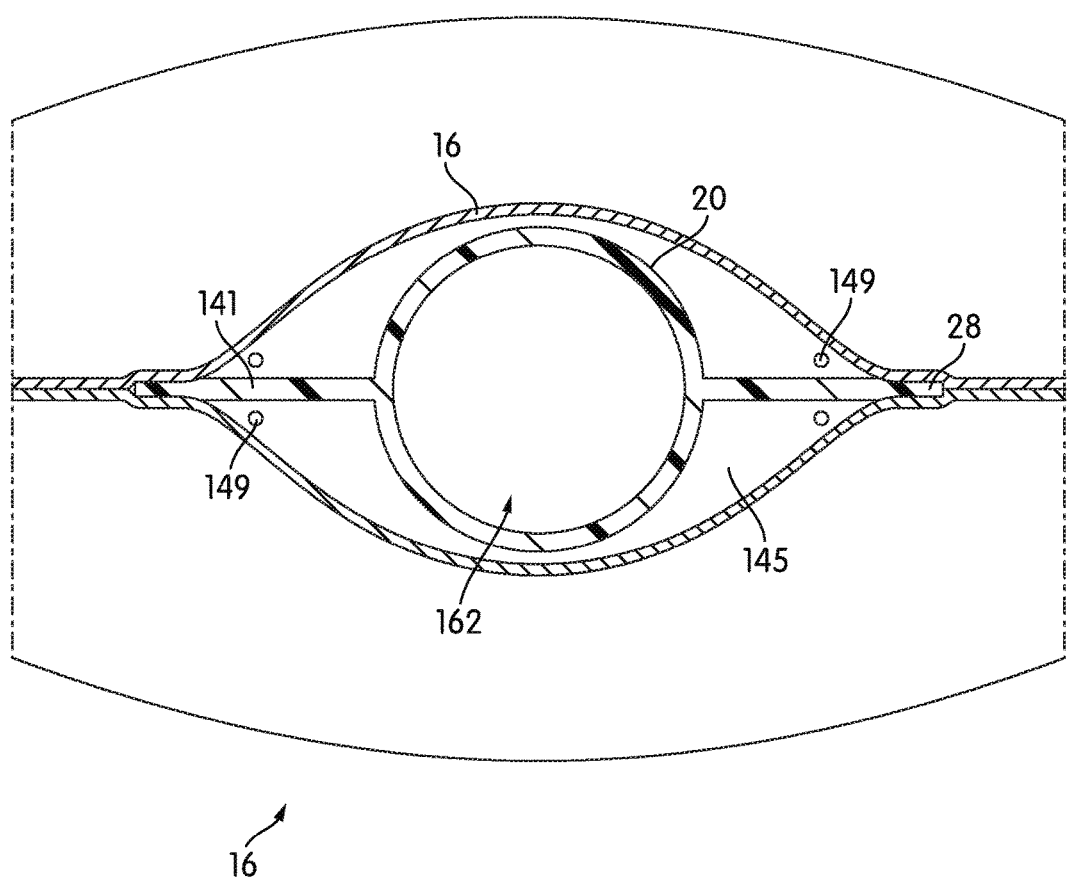
FIG. 14 is a top sectional view taken along line 14-14 of FIG. 1 according to one embodiment.

Referring to FIGS. 11-14, another embodiment of a spout incorporating a venting feature is shown. As shown in FIG. 11 the shape, size and configuration of ribs 145 generally mirrors the shape, size and configuration of bottom sealing wall 143. Also, as seen in FIG. 14 similar to the uninterrupted perimeter of the bottom sealing wall 143, the perimeter of the ribs 145 is uninterrupted, allowing the pouch 16 to form an uninterrupted fluid tight seal along the entirety of the perimeter of the ribs 145 from one wing 28 to opposite wing 28. This fluid-tight attachment or bonding between the pouch 16 and the ribs 145 may involve an adhesive, a melted thermoplastic, heat welding, ultrasonic welding, or other means for sealing the structures together.

Figure 12:
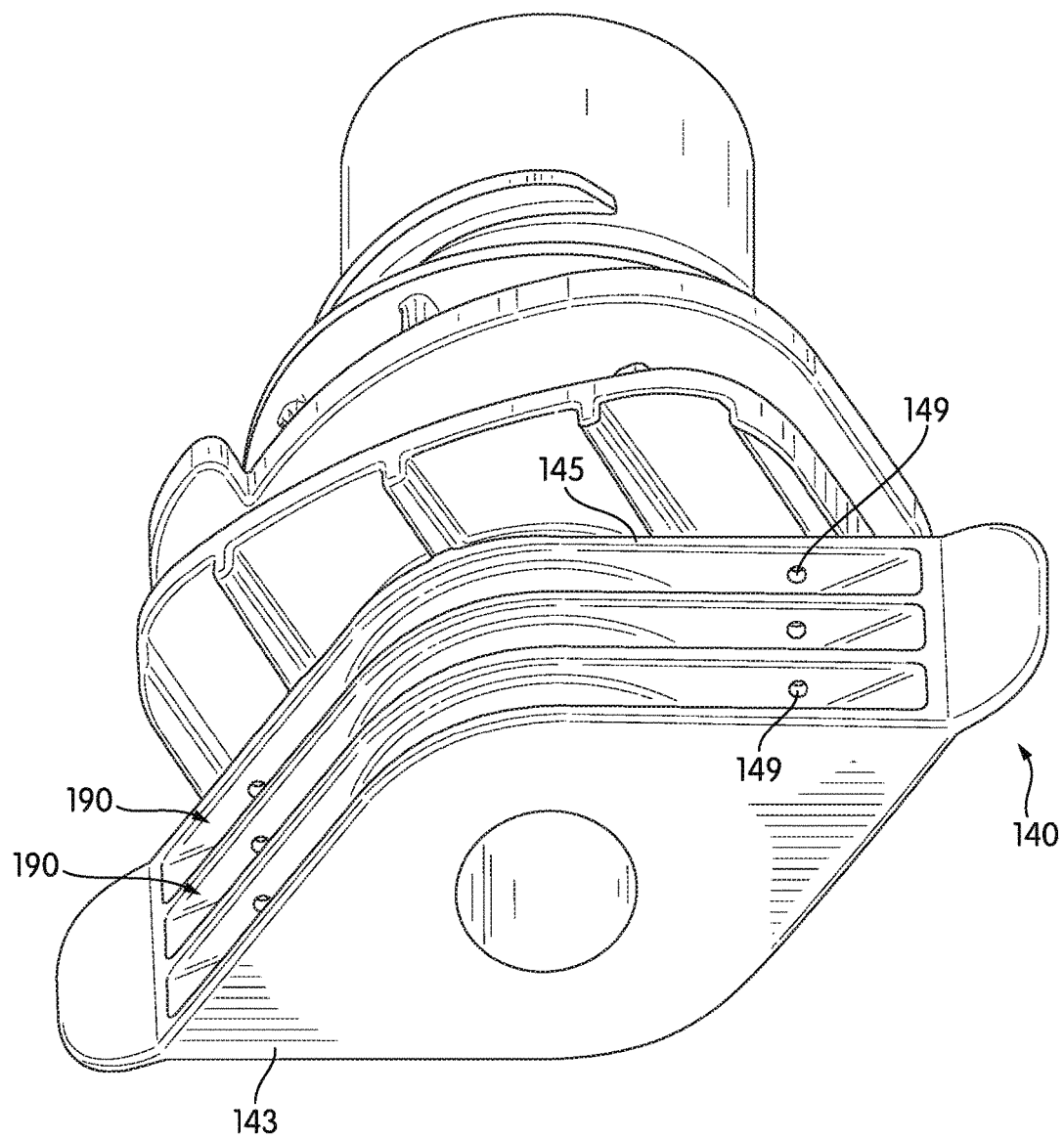
FIG. 12 is bottom perspective view of the spout of FIG. 11 according to one embodiment.
Figure 13:
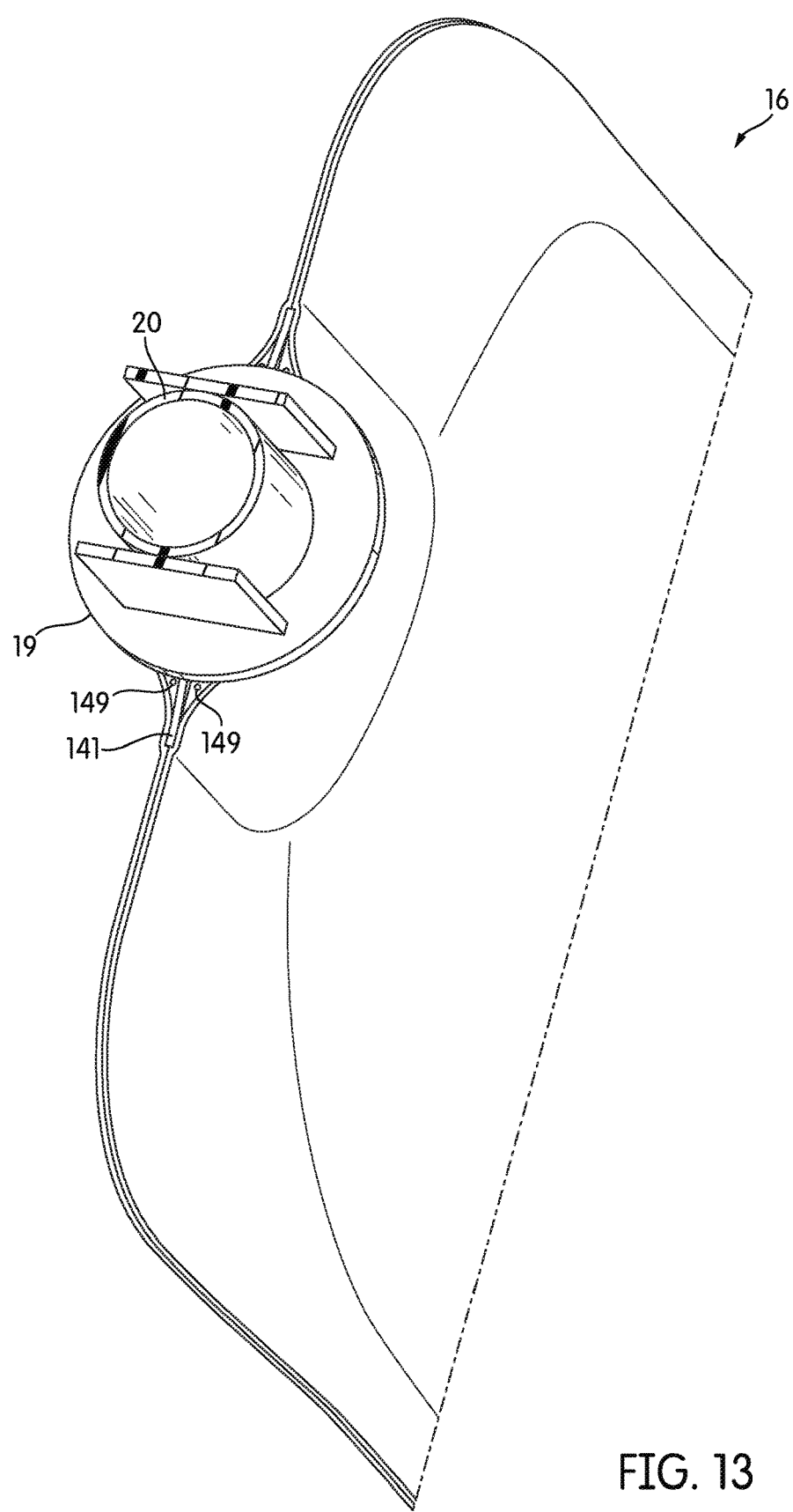
FIG. 13 is a perspective view from above of the spout of FIG. 11 sealed to the pouch-type container of FIG. 1 according to one embodiment.

As shown in FIG. 12, extending through each rib 145 from a top surface to a bottom surface of each rib 145 is a gap 149, formed as a hole or aperture extending from a top surface of each rib 145 to a bottom surface of each rib. As shown in FIG. 12, gaps 149 define vents which permit fluid communication between inner spaces 190 and the outside environment after the pouch and mounting portion 140 have been attached. The holes or apertures in ribs 145 forming gaps 149 can be formed in ribs 145 prior to attachment of spout 14 to pouch 16. In other embodiments, gaps 149 can be formed in ribs 145 after spout 14 and pouch 16 have been attached. Although in FIGS. 11-14 gaps 149 as illustrated as round holes, gaps 149 may have any shape or cross-section and the dimensions of gaps 149 may vary from those shown in the figures.

Figure 15:
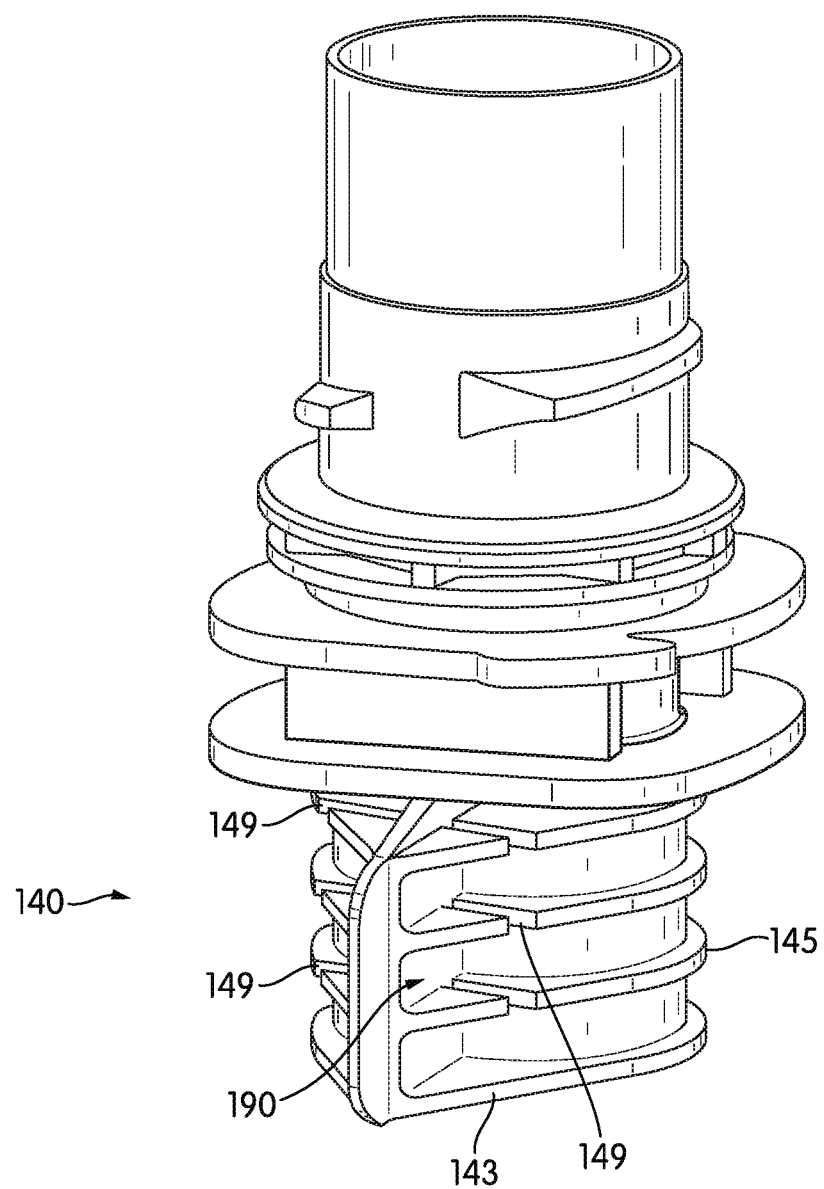
FIG. 15 is a perspective view of a spout including a mounting portion having a vent according to one embodiment.
Figure 16:
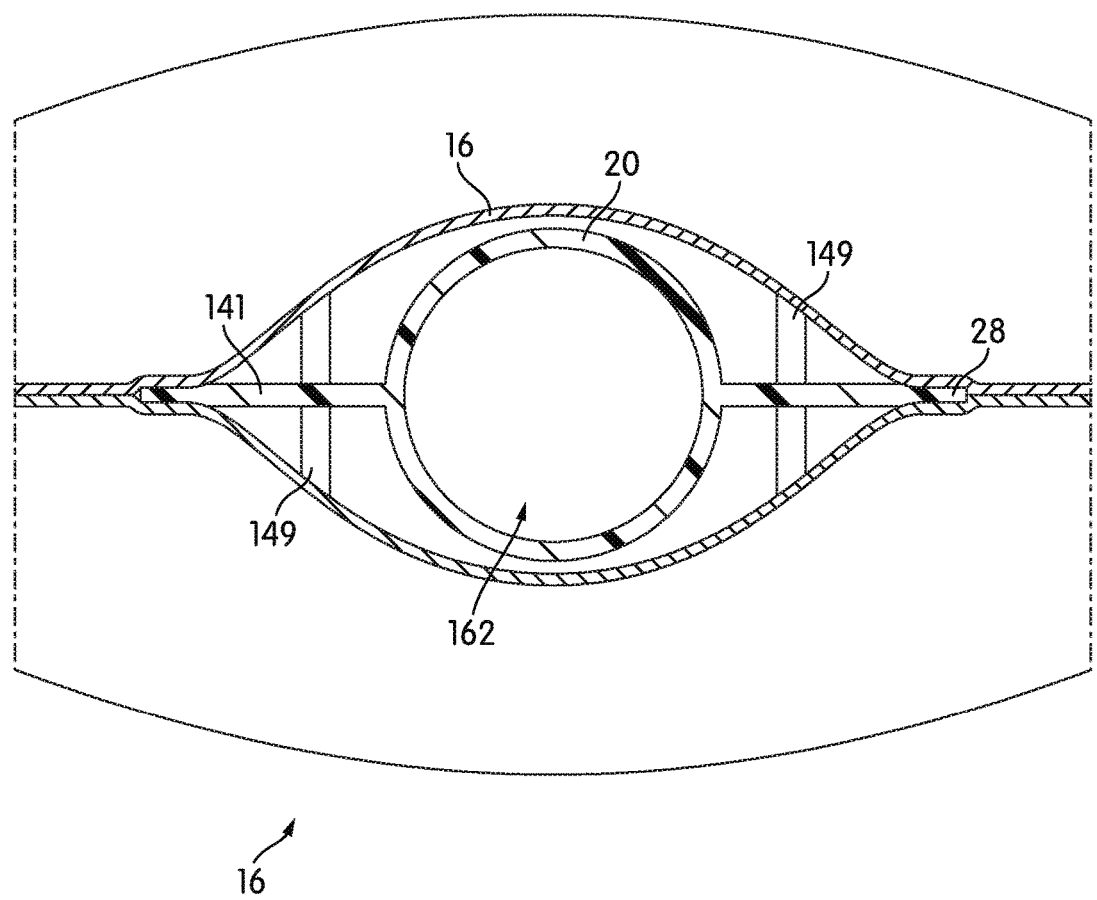
FIG. 16 is a top sectional view taken along line 16-16 of FIG. 1 according to one embodiment.

Referring to FIG. 15 and FIG. 16, another embodiment of a spout 14 incorporating a vent is shown. As shown in FIG. 15, the shape, size and configuration of ribs 145 generally mirrors the shape, size and configuration of bottom sealing wall 143. As illustrated by FIG. 15, in this embodiment, ribs 145 extend between wings 28, similar to bottom sealing wall 143. However, as shown in FIG. 16, unlike the bottom sealing wall 143 which has an uninterrupted outer perimeter (as shown in FIG. 5) the outer perimeter of ribs 145 is interrupted by gaps 149. The gaps 149 formed in the perimeter of ribs 145 extend from a bottom surface to a top surface of each rib 145. In FIG. 15 and FIG. 16 gaps 149 are shown as extending through the ribs 149 from the outer perimeter of ribs 145 to the support wall 141. However, in other embodiments gaps 149 may extend through the ribs 145 from the outer perimeter of ribs 145 to a depth that does not extend all the way to support wall 141. Gaps 149 may be formed along any portion of ribs 145 between first and second wings 28. Also, although in FIGS. 15 and 16 gaps 149 are illustrated as having a generally rectangular shape, gaps 149 may have any shape or cross-section and the dimensions of gaps 149 may vary from those shown in the figures.

As seen in FIG. 16, because gaps 149 are formed in the outer perimeter of ribs 145, the interface between the inner surfaces of the sidewalls of the pouch 16 and the ribs 145 is interrupted along those portions of the length of the ribs 145 at which gaps 149 are formed in the ribs 145. As also seen in FIG. 16, at those portion at which the outer perimeter of ribs 145 is in contact with the inner surfaces of sidewall of pouch 16, the outer perimeters of ribs 145 are configured to form a fluid-tight interface with the inner surfaces of the sidewalls of pouch 16. This fluid-tight attachment or bonding between the pouch 16 and the ribs 145 may involve an adhesive, a melted thermoplastic, heat welding, ultrasonic welding, or other means for sealing the structures together.

As seen in FIG. 16, at those portions along the length of ribs 145 at which gaps 149 are formed, the pouch 16 is attached to mounting portion 140 such that the pouch 16 lays taut against the outer perimeter of the mounting portion 140 so as to prevent the pouch from occluding gaps 149 and to allow for fluid communication between spaces 190 and the outside environment.

Figure 17:
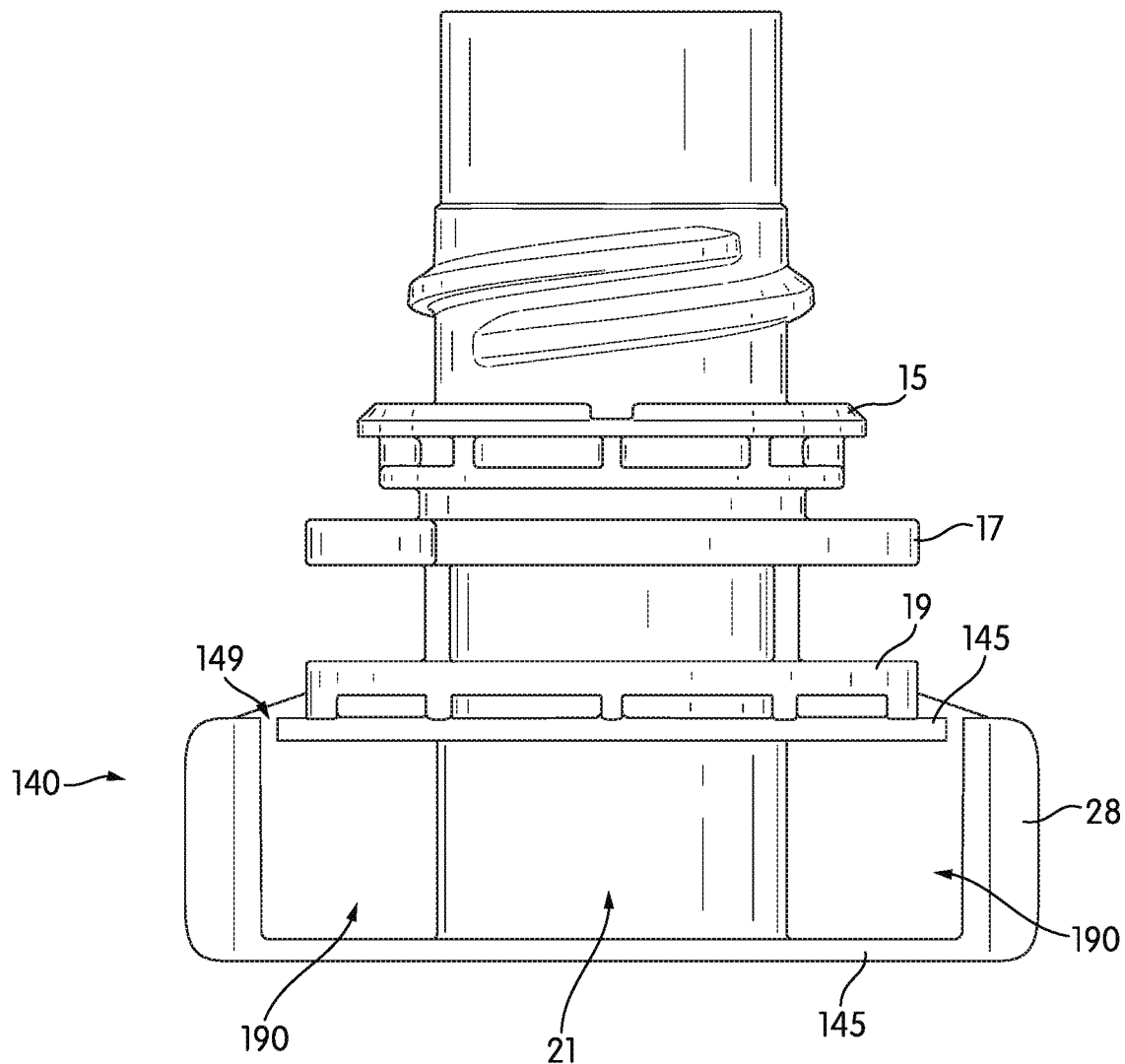
FIG. 17 is a front perspective view of one embodiment of a spout including a mounting portion having a vent according to one embodiment.

As illustrated by the various embodiments discussed above, spout 14 may include multiple ribs 145. Alternatively, in other embodiments, a spout 14 incorporating vents as shown in any of these embodiments may include only a single rib 145. Shown in FIG. 17 is one embodiment of a spout 14 including a single rib 145. The structure and configuration of the rib 145 and the corresponding vent formed by gaps 149 in the embodiment shown in FIG. 17 is similar to the structure and configuration of the ribs 145 and the corresponding vents formed by gaps 149 in the embodiment shown in FIG. 2. However, whereas in FIG. 2 the mounting portion 140 is illustrated as including three ribs, as seen in FIG. 17, the mounting portion includes a single rib 145. Although FIG. 17 illustrates an embodiment of a spout having only a single rib 145 and having a mounting portion 140 including a vent structure similar to the vent structure disclosed with reference to the embodiment of FIG. 2 discussed above, the use of a single rib 145 may be incorporated into any of the embodiments of the mounting portion 140 having a vent structure as discussed herein.

Figure 18:
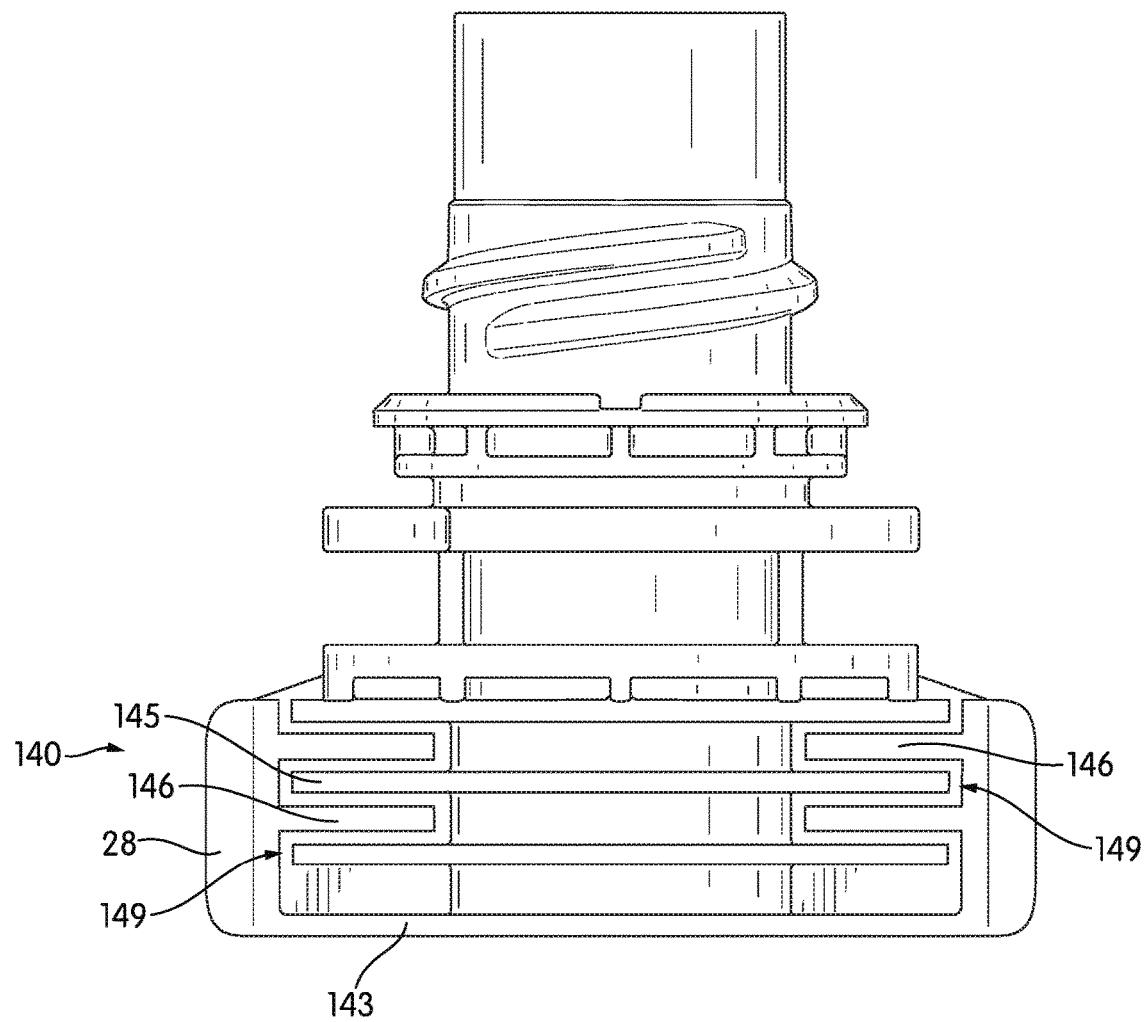
FIG. 18 is a front perspective view of another embodiment of a spout including a mounting portion having a vent according to one embodiment.

As shown in FIG. 18 spout 10 incorporating a venting feature as shown in any of the embodiments may also include one or more side projections 146. Although FIG. 18 illustrates an embodiment of a spout incorporating side projections 146 having a mounting portion 140 including a vent structure similar to the vent structure disclosed with reference to the embodiment of FIG. 2 discussed above, side projections 146 may be incorporated into any of the embodiments of the mounting portion 140 having a vent structure as discussed herein.

Referring to FIG. 18, side projections 146 may be configured to provide a greater surface area against which to seal the pouch 16 to allow for a more secure attachment of the spout 14 to the pouch 16. Also, side projections 146 may be configured to strengthen and prevent distortion or and damage to the spout 14 and to prevent damage to or accidental rupturing of the pouch 16 after the pouch 16 and spout 14 have been attached.

As shown in FIG. 18, in some embodiments side projections 146 project inwardly from wings 28. In other embodiments, side projections 146 extending perpendicularly outward from support wall 141 or radially outward from tube 20. Side projections 146 may be spaced in between adjacent ribs 145, and the outer perimeter of the side projections 146 may generally mirror the shape, size and configuration of the bottom sealing wall 143 and/or the ribs 145. Although in embodiment shown in FIG. 18 two side projections 146 are shown extending from each surface of on both wings 28, in other embodiments the number and positioning of side projections 146 may vary.

In one embodiment, not shown, side projection 146 may include a single side projection 146 having a height substantially similar to the height of wings 28 and extending from one wing 28 to the opposite wing 28 on both the front and rear sides of the mounting portion 140. In such an embodiment, the side projection 146 may form an annular wall which circumferentially surrounds the entire outer perimeter of ribs 145 around both the front and rear of the mounting portion 140. In such an embodiment, the side projection 146 may be configured so as to maximize the surface area of the mounting portion 140 to which the pouch 16 may be sealed. In some embodiments, the entirety of the bottom perimeter of the side projection may be attached to and circumferentially surround the upper surface of bottom sealing wall 143. In other embodiments, the side projection 146 may be attached to the mounting portion 140 only at wings 28. A mounting portion 140 having such a side projection 146 may be incorporated into the structure of any of the mounting portions 140 disclosed herein.

Figure 19:
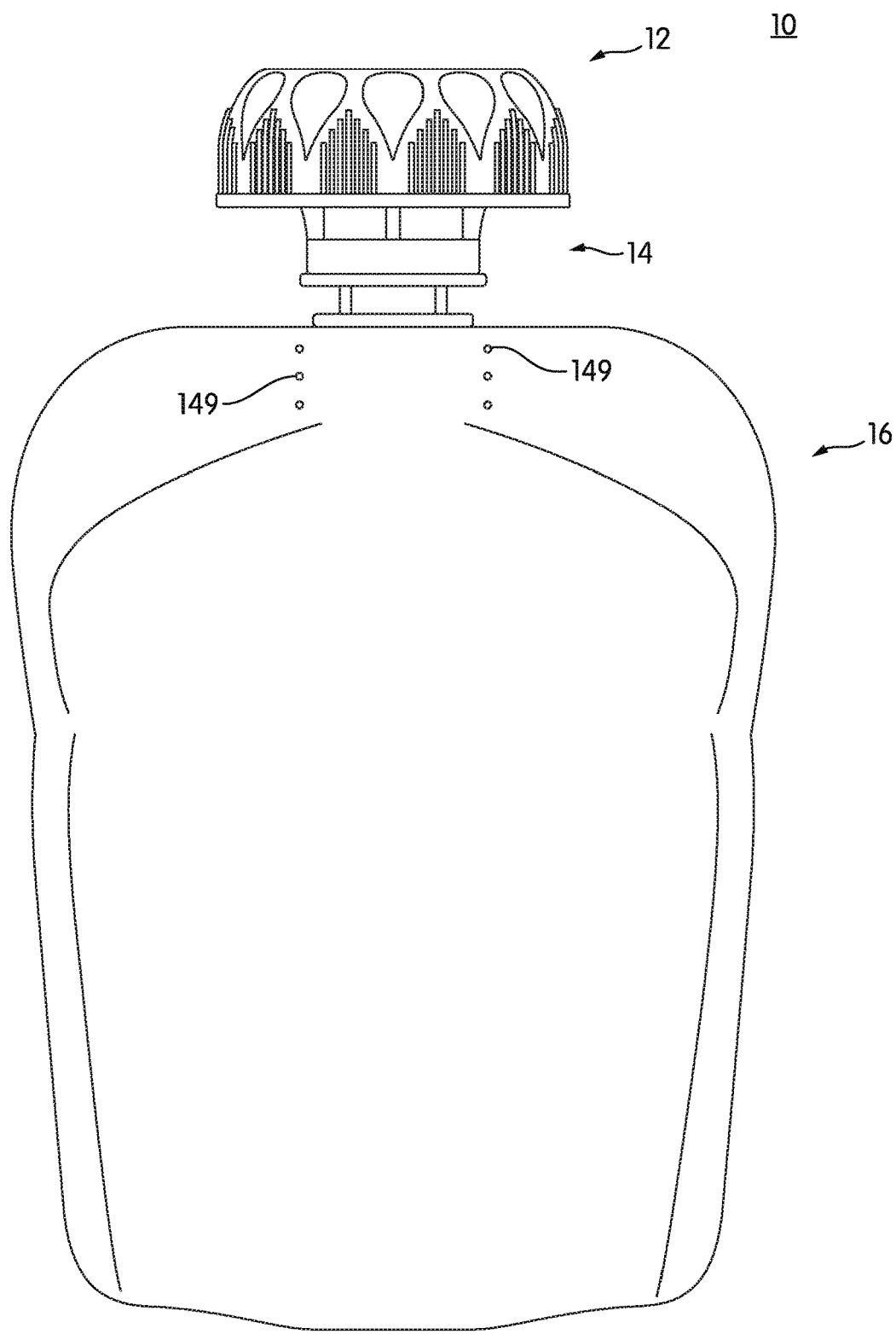
FIG. 19 shows a container assembly including a pouch having a vent feature according to one embodiment.
Figure 20:
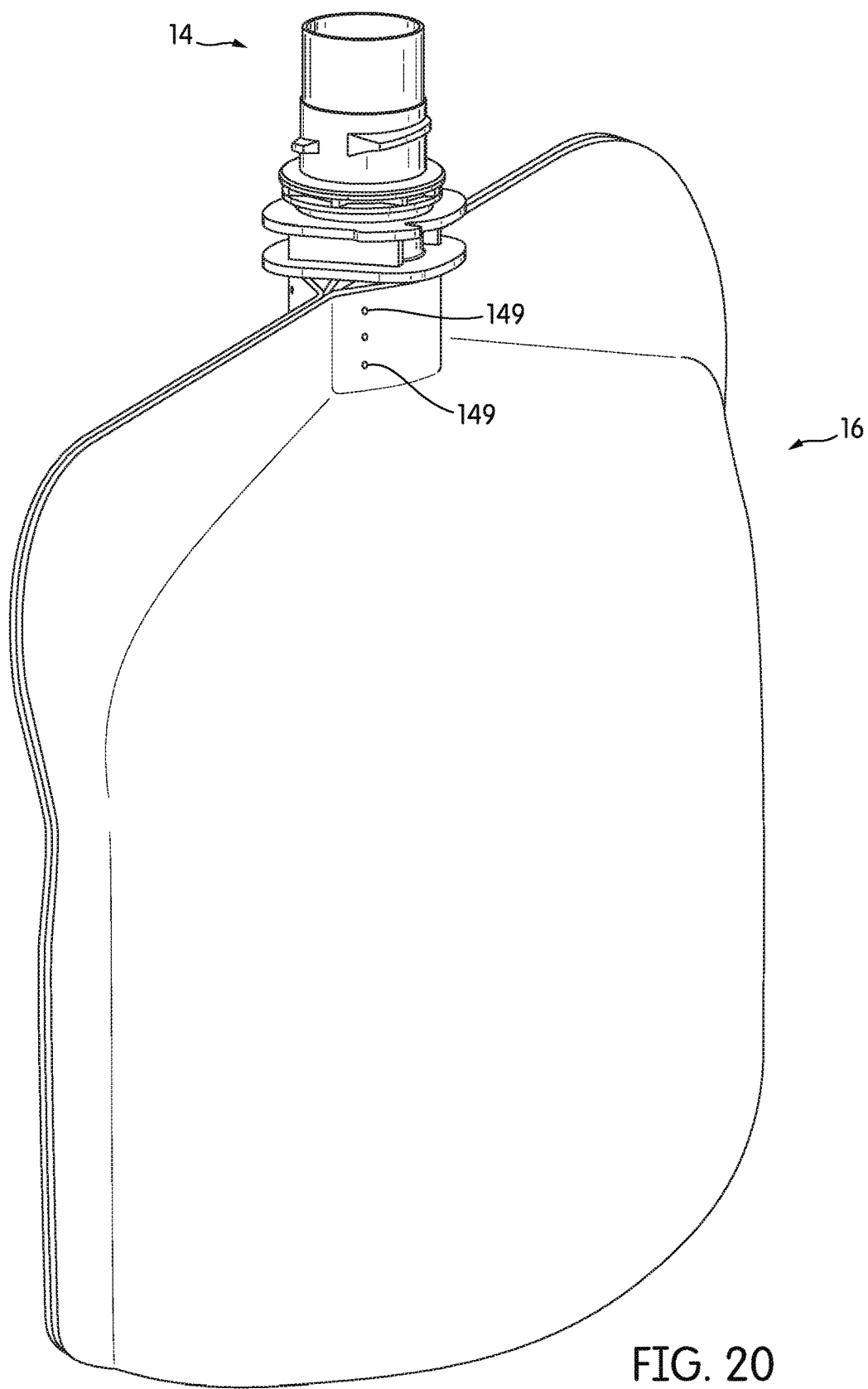
FIG. 20 is a perspective view of the container assembly of FIG. 19 according to one embodiment.

Referring to FIGS. 19-22, another embodiment of a container assembly 10 including vents that allow for fluid communication between the external environment and cavities (such as, e.g. spaces 190) formed between the inner surfaces of the sidewalls of pouch 16 and the external surfaces of mounting portion 140 when the mounting portion 140 and pouch are attached, is shown. As shown in FIGS. 19 and 20, gaps 149 are formed in the upper portion of pouch 16. Gaps 149 are formed as holes or apertures that extend from an outer surface of the sidewalls of pouch 16 to an inner surface of the sidewalls of pouch 16, creating a passageway through which fluid, such as, e.g., air, may pass. The holes or apertures in pouch 16 forming gaps 149 can be formed in pouch 16 prior to attachment of spout 14 to pouch 16. In other embodiments, gaps 149 can be formed in pouch 16 after spout 14 and pouch 16 have been attached. Although in FIGS. 19-22 gaps 149 as illustrated as round holes, gaps 149 may include any shape or cross-section and the dimensions of gaps 149 may vary from those shown in the figures.

Figure 22:
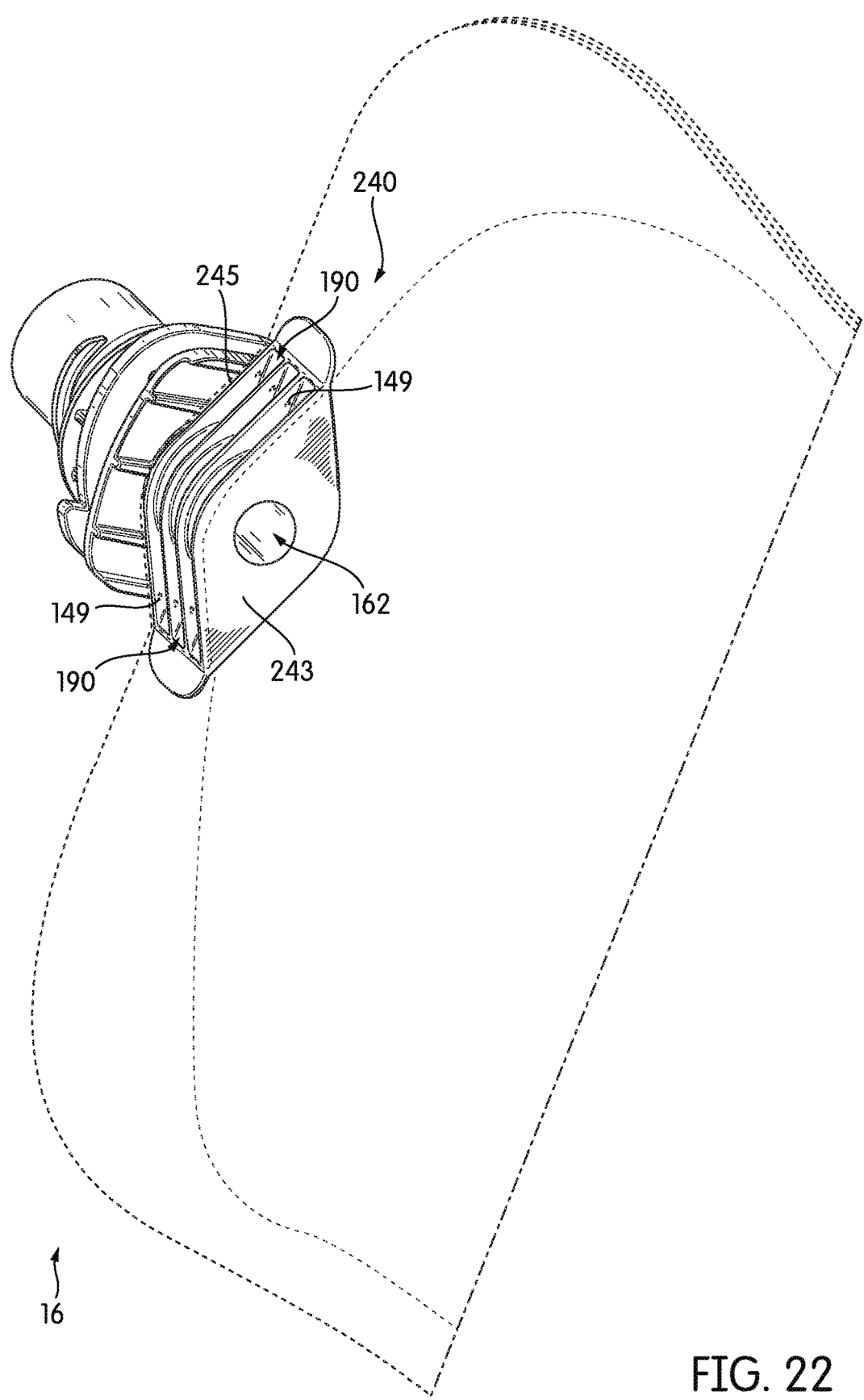
FIG. 22 is a bottom perspective view of the container assembly of FIG. 19 according to one embodiment.

As shown in FIGS. 20 and 22, in one embodiment, a pouch including gaps 149 is configured to be attached a mounting portion 240 which does not include any vent structure. As shown in FIGS. 20 and 22, the mounting portion 240 may include a bottom sealing wall 243 and ribs 245 whose outer perimeters are configured to form an uninterrupted, fluid-tight interface with the inner surfaces of the sidewalls of pouch 16 when the pouch 16 and spout 14 are attached. Additionally, the bottom sealing wall 243 and ribs 245 each include a solid structure that, with the exception of an opening through which tube 20 passes, includes no apertures or holes that pass from a bottom surface to a top surface. The openings in the bottom sealing wall 243 and ribs 245 through which tube 20 passes are attached to the exterior surface of tube 20 via a fluid-tight attachment.

Figure 21:
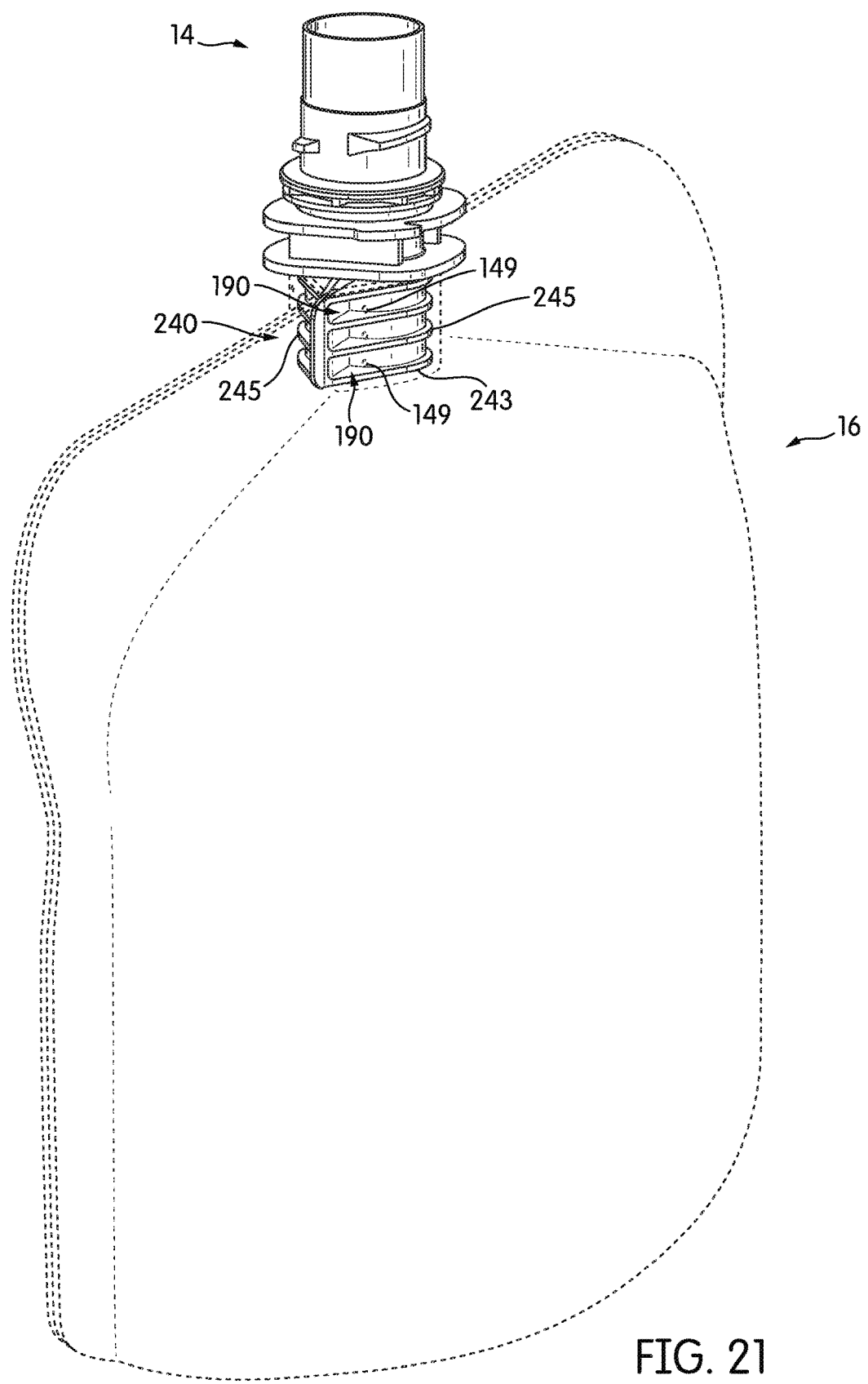
FIG. 21 is a perspective view of the container assembly of FIG. 19 according to one embodiment.

Referring to FIGS. 21 and 22, gaps 149 are arranged on the pouch 16 such that when pouch 16 and spout 14 are attached, the gaps 149 are aligned in between adjacent ribs 245 such that gaps 149 provide a vent that allows for fluid communication between spaces 190 formed between adjacent ribs 245 and between bottommost rib 245 and bottom sealing wall 243 and the outside of the pouch 16.

Although in the embodiment of FIGS. 20-22 pouch 16 including gaps 149 is shown attached to a mounting portion 240 that does not include a vent structure, the pouch 16 shown in the embodiment of FIGS. 20-22 may be used with and attached to a mounting portion 140 including vents according to any of the embodiments disclose herein. Similar to the embodiment shown in FIGS. 19-22, in such embodiments in which a mounting portion 140 including vents is attached to a pouch 16 also having gaps 149, pouch 16 is attached to spout 14 such that the gaps 149 of pouch 149 are aligned and positioned in between ribs 145 of the mounting portion 140, as similarly shown in FIGS. 21 and 22.

Discussed below are various embodiments of spout 14 and/or closure 12 that may be incorporated into a container assembly 10 including a vent, such those discussed in the embodiments of FIGS. 2-22 above.

Figure 23:
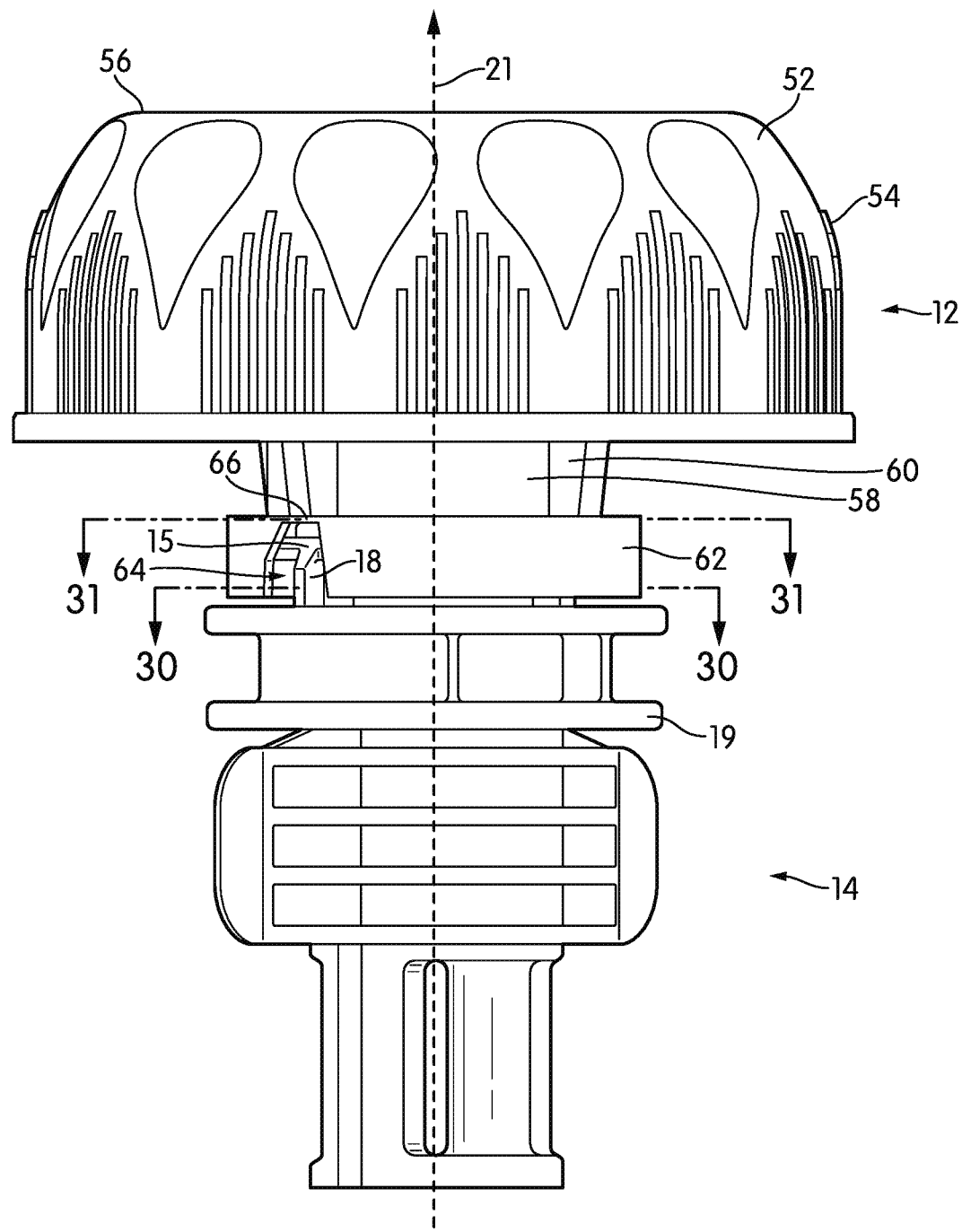
FIG. 23 is a front view of a closure attached to a spout according to one embodiment.

Referring to FIG. 23, a spout 14 is shown with a closure 12 according to one embodiment. The closure 12 has an outer sidewall 56 with an exterior surface 52, shown in this embodiment with a textured design 54 molded into the exterior surface 52. The textured design 54 facilitates gripping by a user. In other embodiments, the pattern may be etched onto the exterior surface 52, printed onto the exterior surface 52, or adhered to the exterior surface 52. The pattern of the textured design 54 may vary in size, complexity, symmetry, or distribution. The closure 12 may not include a textured design 54 in alternate embodiments.

The outer sidewall 56 is attached to an inner wall 58 by a support structure, shown as vertical stabilizers 60. Although the embodiment shown has four vertical stabilizers (all four stabilizers 60 are shown in FIG. 25), closure 12 may include a different number of vertical stabilizers 60 as may be appropriate based on the material of the closure, the dimensions of the closure, and the intended use of the container.

Figure 24:
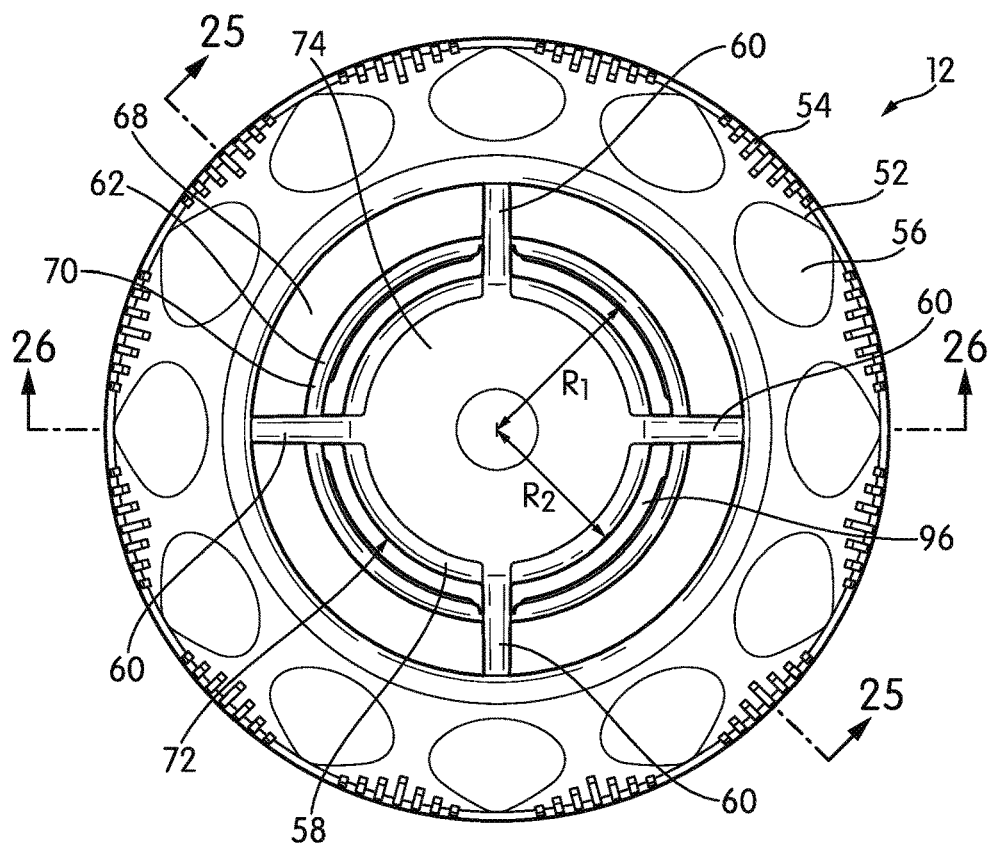
FIG. 24 is a top view of the closure of FIG. 23 according to one embodiment.

FIG. 24 shows the end wall 74 of the closure 12. The end wall 74 encloses the inner wall 58 of the closure 12, sealing in the contents of the pouch 16. FIG. 24 shows a channel 68 running through the closure 12 between the outer sidewall 56 and the inner wall 58. The channel 68 allows air to pass through the closure 12 as a safety measure to allow for one to breathe if the closure 12 is accidentally swallowed. The channel 68 prevents the complete obstruction of the airway by the closure 12 despite the presence of the end wall 74.

Figure 25:
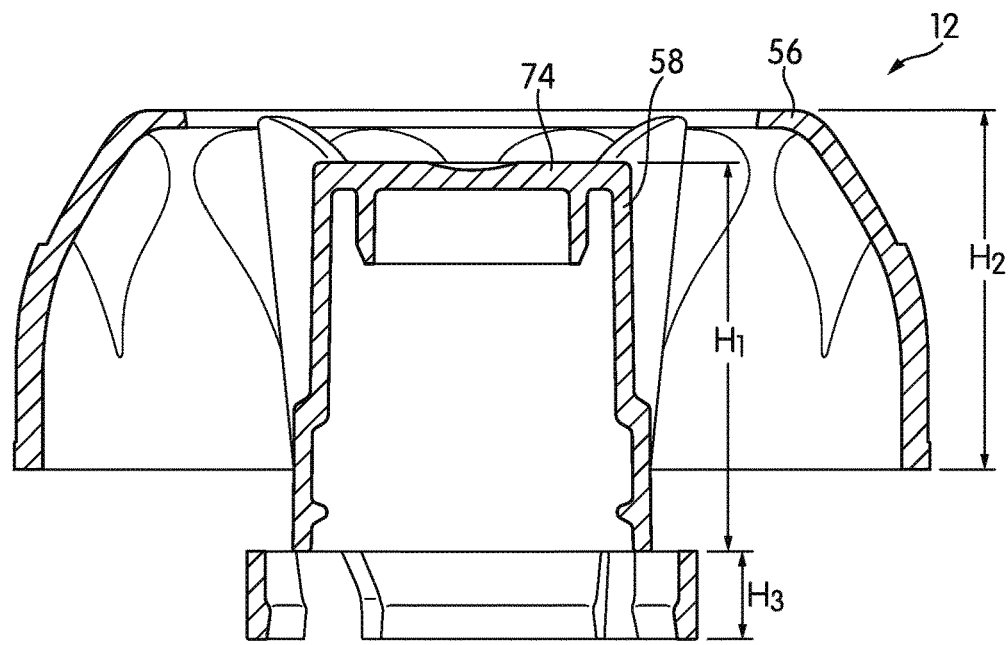
FIG. 25 is a cross-sectional view of the closure of FIG. 23 taken along line 25-25 in FIG. 24 according to one embodiment.

Referring to FIG. 25, one embodiment of a cross-sectional view of the inside of the closure 12 is shown. This cross-sectional view displays the inner wall 58 and the outer sidewall 56. The inner wall 58 has a height, shown as H1. The outer sidewall 56 has a height, shown as H2. The safety band 62 has a height, shown as H3. In this embodiment, the end wall 74 and the upper end of the inner wall 58 are longitudinally below the upper end of the outer sidewall 56. Thus, in the embodiment shown, H2 is less than H1 and H3 is less than both H1 and H2.

Figure 26:
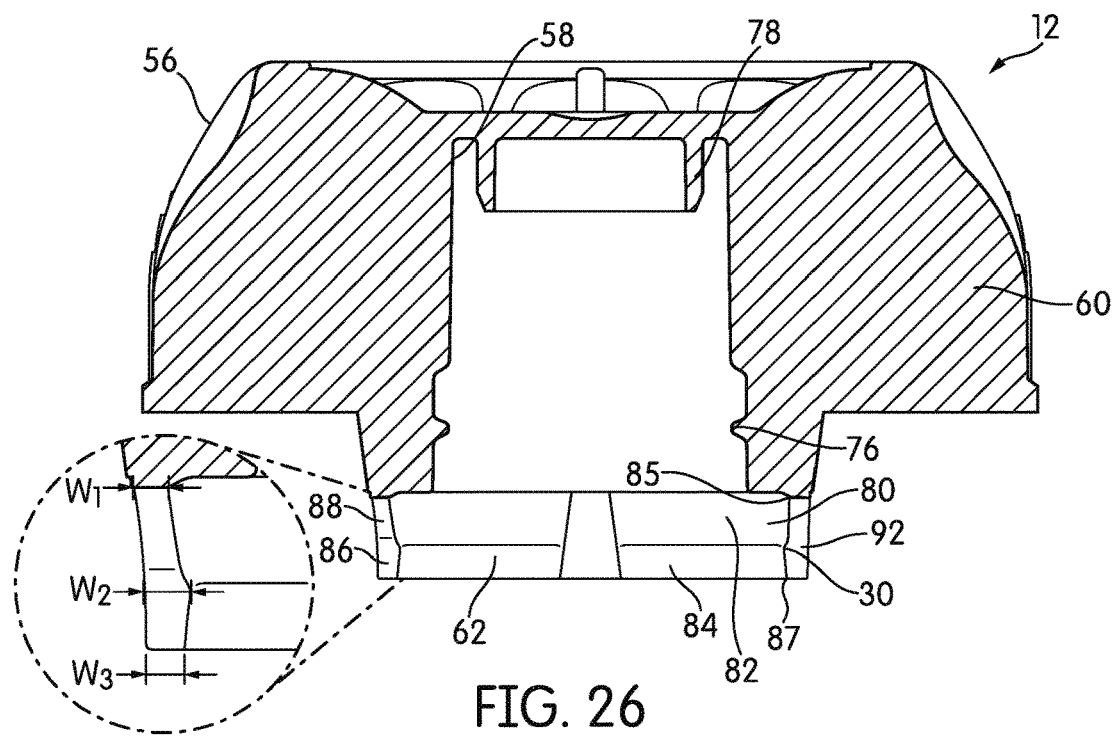
FIG. 26 is a cross-sectional view of the closure of FIG. 23 taken along line 26-26 in FIG. 24 according to one embodiment.

Referring to FIG. 26, a cross-sectional view of the inside of the closure 12 is shown. This cross-sectional view displays the vertical stabilizers 60 that connect the inner wall 58 and the outer sidewall 56. In this embodiment, the vertical stabilizers 60 are integrally formed with the outer sidewall 56 and the inner wall 58. In alternate embodiments, the vertical stabilizers 60 are formed independently of the outer sidewall 56 and the inner wall 58 and then attached (e.g., via welding) after formation. Inner wall 58 includes an interior thread 76 molded into the inner wall 58. The interior thread 76 of the inner wall 58 engages with the exterior thread 26 of the spout 14 to allow for sealing of the pouch 16 by rotation of the closure 12 on the spout 14.

Sealing of the pouch 16 is accomplished by the interaction of the top sealing surface 22 of the spout 14 with the sealing rim 78 of the closure 12. The sealing rim 78 of the closure 12 is an annular rim that extends downward from the end wall 74 into the interior area formed by the inner wall 58. The top sealing surface 22 fits into the area between the sealing rim 78 and the inner wall 58 to seal in the contents of the pouch 16.

FIG. 23 displays one embodiment of a safety band 62. Below the inner wall 58 the safety band 62 extends around spout 14. The safety band 62 of the closure 50 includes a gap 64. Above the gap 64 in the safety band 62, the frangible connection, shown as bridge of material 66 over the gap 64 in the safety band 62, is shown upstretched and unbroken, signifying to the user that the closure 12 has not previously been removed from spout 14. In some embodiments, the length of the bridge of material as it extends around the circumference of the safety band 62 measures between 0.015 and 0.030 inches. The frangible connection, shown as the band of material 66 over the gap 64 in the safety band 62 has a radial width or a radial dimension that is measured along a radius extending from the central axis. Similarly, the safety band 62 has a radial width or radial dimension that can be measured from an inner edge to an outer edge of the safety band 62 along a radius extending from the central axis.

As seen in FIG. 23, in this embodiment, located above lower flange 19 and mounting portion 140 of spout 14, the spout 14 includes an upper flange 15 and a tab 18. The tab 18 of the spout 14 engages with the gap 64 of the safety band 62 of the closure 12. FIG. 23 shows the safety band 62 of the closure 12 before the closure 12 has been rotated by a user. In this closed configuration of the safety band 62, the tab 18 protrudes into the gap 64 of the safety band 62. As shown in FIG. 23, the gap 64 is sized larger than the tab 18. This size differential allows for small movements of the closure 12 in relation to the spout 14 during packing, storing, and shipping without stretching or breaking of the bridge of material 66 over the gap 64 in the safety band 62. In some embodiments of the spout 14 and closure 12, the tab 18 may protrude only a portion of the distance into gap 64, and in other embodiments, tab 18 may protrude all the way through the gap 64.

As seen in FIGS. 23 and 24, the tabs 18 are positioned over and aligned with the wings 28 so that the user is able to clearly view the safety band 62 when looking at the front of the container assembly 10. In other embodiments, the tabs 18 are not positioned over the wings 28 of the mounting portion 140.

As shown in FIG. 24, the upper surface 70 of the safety band 62 is visible through the channel 68 because the inner radius R1 of the safety band 62 is greater than the outer radius R2 of the inner wall 58. The inner wall 58 of the closure 50 has an exterior surface 72. The outer radius R2 of the inner wall 58 is measured from the central axis to the exterior surface 72 of the inner wall 58. The relationship between the inner radius R1 of the safety band 62 and the outer radius R2 of the inner wall 58 allows for the movement of the safety band 62 upon opening of the closure 12 by the user. Without space 96 between the safety band 62 and the exterior surface 72 of the inner wall 58, mechanical forces may limit the degree of movement of safety band 62 on opening of the container assembly 10 which in turn may limit the visibility of the tamper indicating function provided by safety band 62. In one embodiment of closure 12, the radially exterior surface of the safety band 62 is a cylindrical surface.

When the container assembly 10 is opened, not only are the bands of material 66 above the gaps 64 in the safety band 62 stretched and broken, but the safety band 62 itself is displaced radially outward by the removal of the closure 12. If the closure 12 is placed back on the container assembly 10, the safety band 62 remains in the displaced position relative to its original position, having been pushed radially outwards away from the central axis and axially upwards by the upper flange 15. The displacement of the safety band 62 is shown in greater detail in FIG. 32 and FIG. 33.

FIG. 26 shows the cross-sectional shape and structure of the safety band 62. The safety band 62 has an internal surface 80 that extends around a majority of the circumference defined by the safety band 62. This internal surface 80 includes two portions, an upper portion 82 of the internal surface 80 of the safety band 62 and a lower portion 84 of the internal surface 80 of the safety band 62. The upper portion 82 extends radially inward and downward away from an upper edge 85 of inner surface 80 and the lower portion 84 of the internal surface 80 extends radially inward and upward from a lower edge 87 of inner surface 80 meet at a peak 30. In this arrangement, inner surface 80 forms a radially extending rib that cooperates with related structure on spout 14 to provide the tamper-indicating functionality discussed herein.

When assembled with spout 14, the upper portion 82 of the internal surface 80 of the safety band 62 is positioned against the upper flange 15 of the spout 14 when the closure 12 is assembled onto the spout 14. When the closure 12 is removed with an upwards twisting motion by the end user, the position of the lower portion 84 of the internal surface 80 of the safety band 62 as radially inside the upper portion 82 means that the entire safety band 62 is forced outwards against the upper flange 15. When the lower portion 84 is pushed against the upper flange 15, the safety band 62 hinges outwards and permanently deforms, signaling to the user that the closure 12 has been opened after manufacture.

The safety band 62 as shown in FIG. 26 includes three widths. W1 is the width of the safety band 62 at the top of the safety band 62 adjacent to the vertical stabilizers 60. W2 is the maximum width of the safety band 62, and is positioned in the longitudinal midsection of the safety band 62. W3 is the width of the safety band 62 at the bottom of the safety band 62, at the lowermost edge of the closure 12. In the embodiment shown, W2 is greater than W1 and W3.

When assembled, the slope of the internal surface 80 from W1 to W2 rests against the upper flange 15 of the spout 14. When the closure 12 is pulled upwards by a user, the resistance from the upper flange 15 forces the displacement of the safety band 62 radially outwards. W3 is smaller than W2 to allow for the sliding of the safety band 62 over the upper flange 15 of the spout 14 during initial assembly. When the closure 12 is initially placed onto the spout 14, the angled surface from the lower most edge of the closure 12 up to the longitudinal point at which the maximum width W2 occurs allows for placement of the closure 12 without any stretching or breaking of the bridge of material 66 over the gap 64 or any other damage to the safety band 62. In one embodiment, the safety band 62 snaps into place over the upper flange 15 during assembly.

FIG. 26 also displays the differences between the two lateral surfaces that define the gap 64 in the safety band 62. The embodiment of safety band 62 shown has two gaps 64, and the cross-sectional view intersects the gaps so that the left side of FIG. 26 displays the counterclockwise facing surface of the gap 64 and the right side of FIG. 26 displays the clockwise facing surface of the opposing gap 64.

Figure 28:
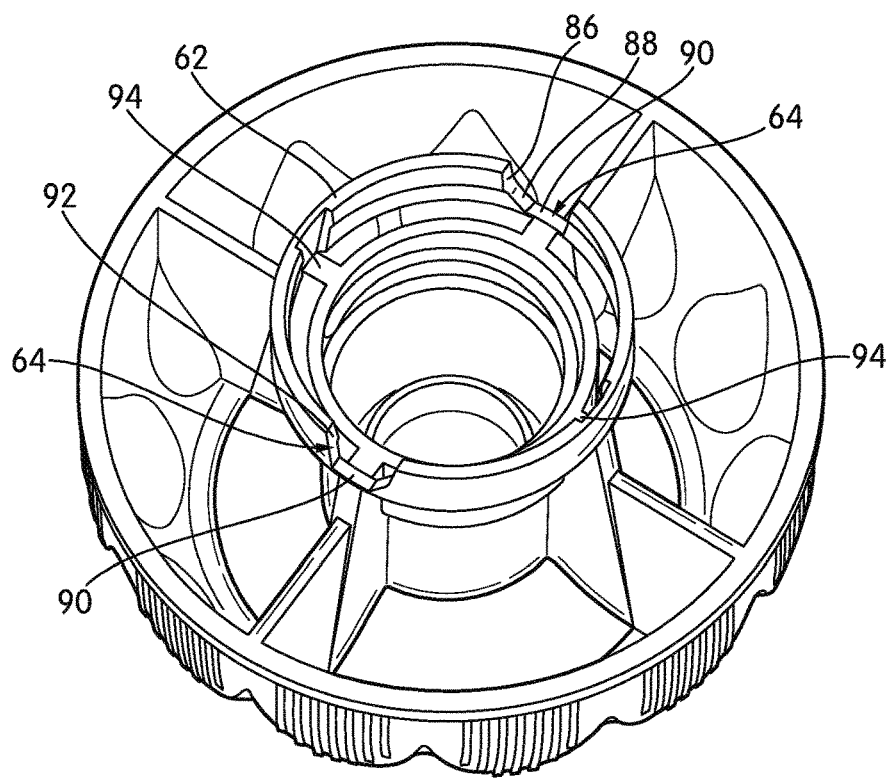
FIG. 28 is a bottom perspective view of the closure of FIG. 23 according to one embodiment.
Figure 29:
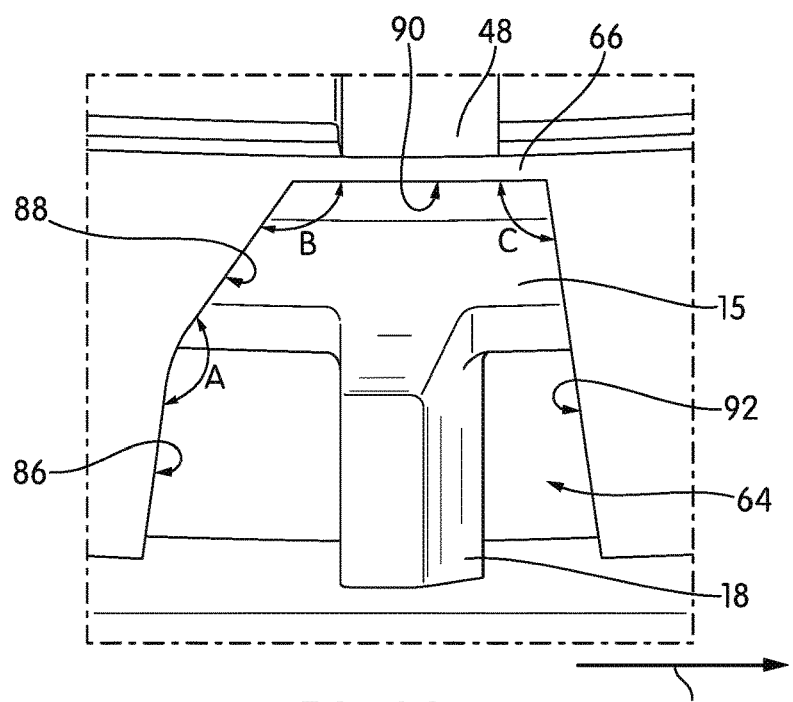
FIG. 29 is a detailed view of a portion of the closure and spout of FIG. 23 according to one embodiment.

Referring to FIGS. 26 and 29, safety band 62 includes two sets of four surfaces that extend between the radially inner surface and the radially outer surface of safety band 62 that each define a gap 64. The first inside surface 86 is the lower surface on the left side of the gap 64. The second inside surface 88 is the upper surface shown on the left side of the gap 64 in FIG. 26. The third inside surface 90 cannot be seen in FIG. 26 but can be seen in FIG. 28 and extends in the circumferential direction between the second inside surface 88 and the fourth inside surface 92. The third inside surface 90 is the bottom surface of the bridge of material 66 over the gap 64 in the safety band 62. In one embodiment of the closure 12, the third inside surface 90 is substantially parallel to the plane defined by the bottom edge of the safety band 62; i.e., the third inside surface is within +/−10 degrees of the plane defined by the bottom edge of the safety band 62. The fourth inside surface 92 of the gap 64 in the safety band 62 can be seen on the right side of the cross-sectional view of FIG. 26. In this embodiment, the longitudinal distance (or height) covered by the fourth inside surface 92 is the same as the longitudinal distance (or height) covered by the first inside surface 86 and the second inside surface 88. In various embodiments, because of the angled position (shown in FIG. 29) of second inside surface 88, the length of inside surface 88 is greater than if the angle of inside surface 88 matched the angle of inside surface 92. In this arrangement, the length of inside surface 88 may act as a lever arm facilitating breakage of bridge of material 66 during opening.

Referring again to FIG. 27 and FIG. 29, the four surfaces that define the gap 64 of the safety band 62 of the closure 50 meet at their edges. Where the first inner surface 86 and the second inner surface 88 meet, a first corner with an angle A is formed. Where the second inner surface 88 and the third inner surface 90 meet, a second corner with an angle B is formed. Where the third inner surface 90 and the fourth inner surface 92 meet, a third corner with an angle C is formed. In some embodiments of the closure 12, angle A, angle B, and angle C are all greater than 90 degrees but less than 180 degrees. In some embodiments of the closure 12, angle A is greater than both angle B and angle C. In some embodiments of the closure 12, angle C is the smallest of the three angles. In some embodiments, at least one of angle A or angle B is greater than 135 degrees.

Figure 30:
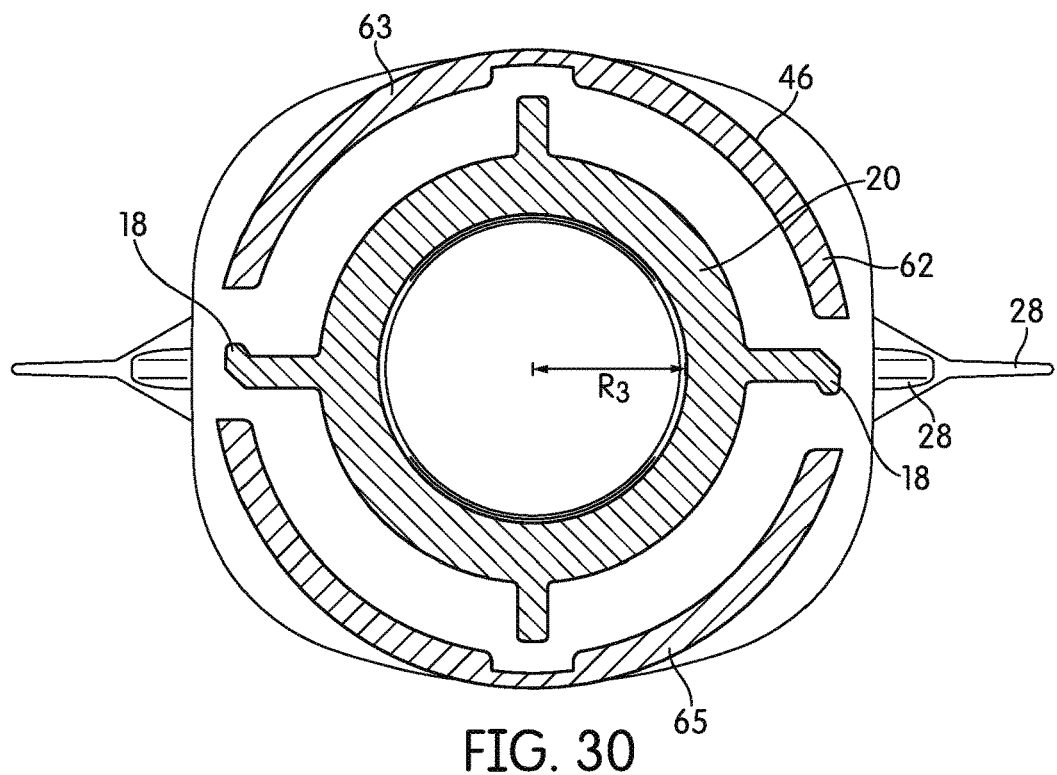
FIG. 30 is a cross-sectional view of the closure and spout of FIG. 23 taken along line 30-30 in FIG. 23 according to one embodiment.

Alternatively, referring to FIG. 30, the safety band 62 includes a first portion 63 and a second portion 65, extending between the clockwise and counterclockwise surfaces of the respective gaps 64. In one embodiment, first portion 63 and the second portion 65 of the safety band 62 each extend between 120 and 175 degrees around the circumference of inner wall 58. In other embodiments, first portion 63 and second portion 65 of the safety band 62 each extend at least 130 degrees and, more specifically, at least 150 degrees around the circumference of inner wall 58.

Figure 27:
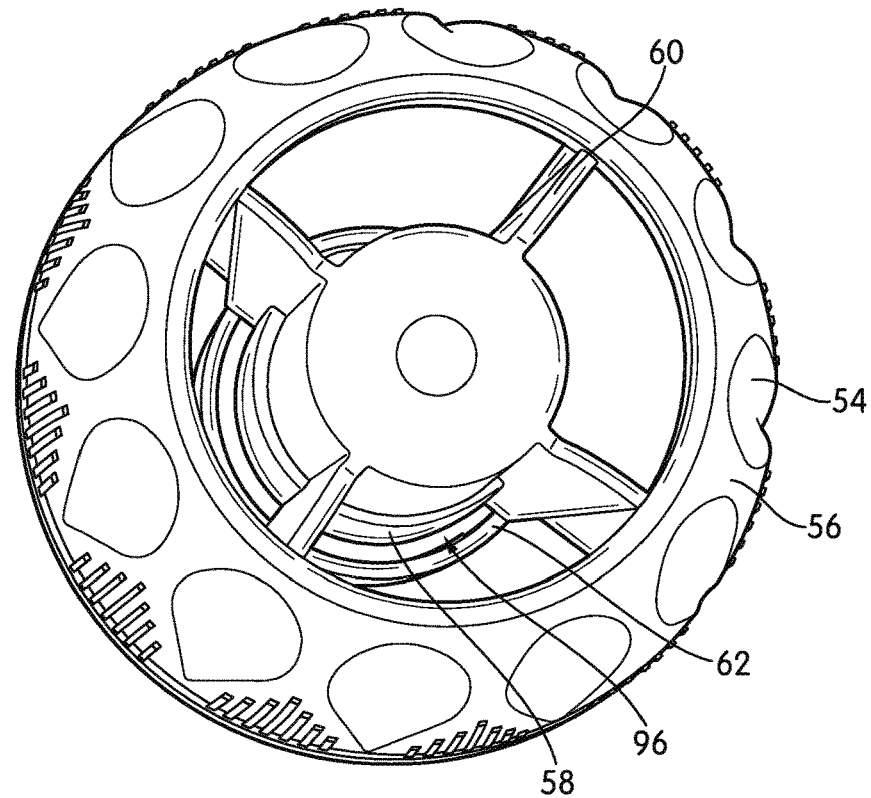
FIG. 27 is a top perspective view of the closure of FIG. 23 according to one embodiment.

Referring to FIG. 27, one embodiment of a top perspective view of the closure 12 is shown. In FIG. 27, raised surfaces and indentations on the exterior surface 52 of the outer sidewall 56 of the closure 50 are shown. This view emphasizes the space 96 between the safety band 62 and the inner wall 58. The space 96 is interrupted by the vertical stabilizers 60 that join the inner wall 58 to the outer sidewall 56, and that join the inner wall 58 to the safety band 62 at four points, three of which can be seen in FIG. 27. The orientation of the four vertical stabilizers 60 can also be seen in FIG. 27; in particular, this embodiment includes four evenly spaced vertical stabilizers 60 that extend outwards at 90° angles. Another embodiment may include two vertical stabilizers 60 at approximately 180 degrees from each other around the circumference safety band 62, i.e. within +/−10 degrees of 180 degrees. Other embodiments may include vertical stabilizers at different angles, or vertical stabilizers that do not join with the safety band 62.

In some embodiments, the vertical stabilizers 60, or any other features of the closure 12, may be described as diametrically opposite one another. This means that the features are approximately 180 degrees around a circumference from one another, within +/−10 degrees of 180 degrees. Additionally, if a range of error is not otherwise specified for a measurement described in degrees, the range of error should include all degrees within +/−10 of the measurement, inclusively.

Referring to FIG. 28, one embodiment of a bottom perspective view of the closure 12 is shown. The two hinge connectors 94 of the closure 12 can be seen in FIG. 7. In this embodiment, the hinge connectors 94 are diametrically opposite each other. This embodiment also has the hinge connectors 94 located equidistant around the circumference of the safety band 62 between the two gaps 64. In this embodiment, the first inside surface 86, the second inside surface 88, and the third inside surface 90 of one of the gaps 64 can be seen. FIG. 28 shows the second inside surface 88, the third inside surface 90, and the fourth inside surface 92 of the other gap. The third inside surfaces 90 of the gaps 64 extend in the circumferential direction between the second inside surfaces 88 and the fourth inside surfaces 92. The fourth inside surfaces 92 are planar surfaces that extend axially away from the third inside surfaces 90, but the first inside surfaces 86 and the second inside surfaces 88 form a convex angle with each other and extend both in the circumferential direction of the safety band 62 as well as extending axially.

Referring to FIG. 29, a detailed view of the tab 18 protruding into the gap 64 of the safety band 62 is shown. The frangible connector 48 extends axially upward from the bridge of material 66 above the gap 64 in the safety band 62. During opening, closure 12 is rotated in the counterclockwise direction indicated by arrow 67 in FIG. 29. In this embodiment, the frangible connector 48 is not as wide as the upper width of the gap 64, so that the bridge of material 66 is not reinforced and may stretch and break easily on opening of the closure 50 by a user. The left side of the bridge of material 66 will stretch and break as the second inside surface 88 and then the first inside surface 86 of the gap 64 hits the tab 18, forcing the tab 18 radially outwards. The right side of the bridge of material 66 will stretch and break as the annular rim 16 forces the safety band 62 outward as the closure 50 and safety band 62 are pulled up by the user. The combined distances of the first inside surface 86 and the second inside surface 88 increase the stress on the left side of the bridge of material 66; the greater the combined distances, the greater the stress on the left side of the bridge of material 66. FIG. 29 shows that the tab 18 is integrally formed with the alignment rim 16, giving it increased strength.

Referring to FIG. 30, a cross-sectional view of the inside of the closure 12 combined with the spout 14 is shown. The inner radius of the tube 20 is shown as R3. As previously noted, with closure 12 assembled, there is space or clearance between the surfaces that define gap 64 and tabs 18 such the safety band 62 are not accidentally damaged during packaging, shipping, and storage of the container assembly 10. The tabs 18 of the spout 14 are aligned with the wings 28 of the mounting portion 140.

The shape of the tabs 18 can be seen most clearly in FIG. 30. In this embodiment, the tabs 18 extend as far as the outer surface 46 of the safety band 62 but do not extend past the radially outer surface of safety band 62. To ensure that the tabs 18 do not break when the closure 12 is twisted by the user, the right side of the tabs 18 have a slanted angle. Thus, when the closure 12 is rotated counterclockwise to open the container assembly 10, the side of the safety band 62 facing the tab 18 will hit the tab 18 and be pushed against the direction of rotation. This will force the end of the safety band 62 that is against the tab 18 radially outwards, breaking the left side of the bridge of material 66 over the gap 64 and freeing that end of the safety band 62 to be forced radially outwards.

Figure 31:
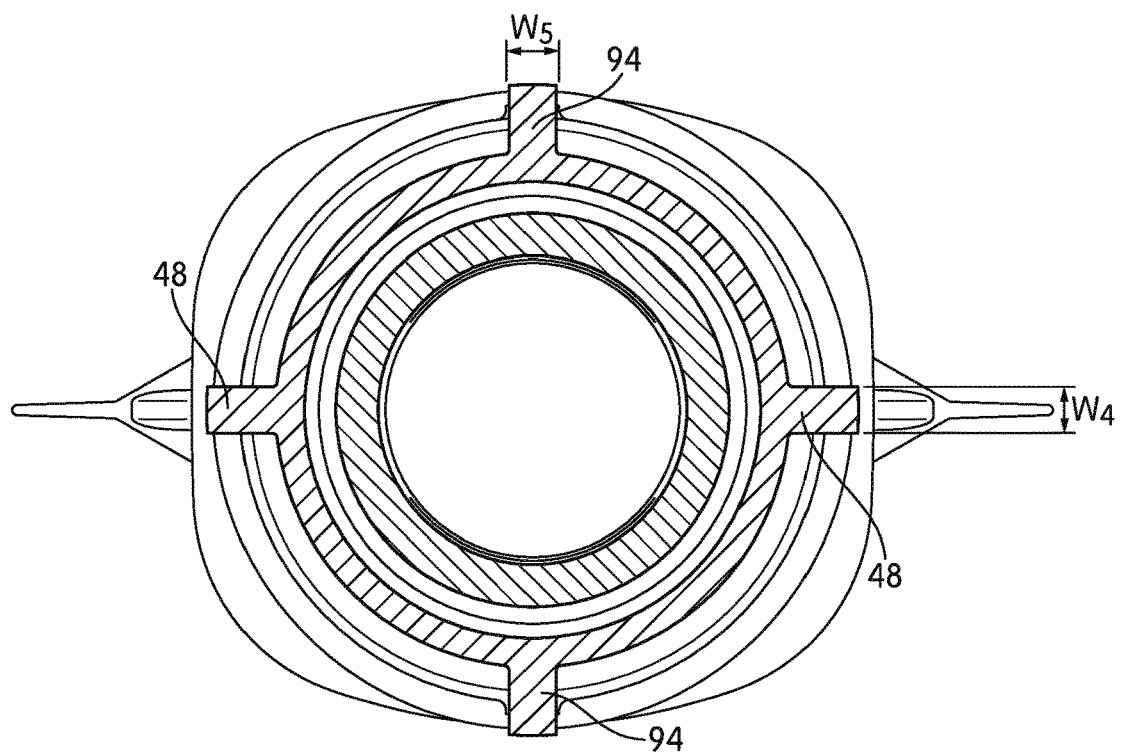
FIG. 31 is a cross-sectional view of the closure and spout of FIG. 23 taken along line 31-31 in FIG. 23 according to one embodiment.

Referring to FIG. 31, one embodiment of a cross-sectional view of the inside of the closure 12 combined with the spout 14 is shown. Here, the frangible connectors 48 and the hinge connectors 94 are shown. In this embodiment, the frangible connectors 48 are positioned over the wings 28 of the mounting portion 140 of the spout 14 and the hinge connectors 94 are located equidistant around the circumference of the safety band 62 between the frangible connectors 48. The frangible connectors 48 have a width shown as W4. In one embodiment, the frangible connectors 48 extend around the circumference of the safety band 62 for less than 0.015 inches. In another embodiment the frangible connectors 48 extend around the circumference of the safety band 62 for less than 0.030 inches. The hinge connectors 94 have a width shown as W5. In one embodiment, W4 is equal to W5.

Figure 32:
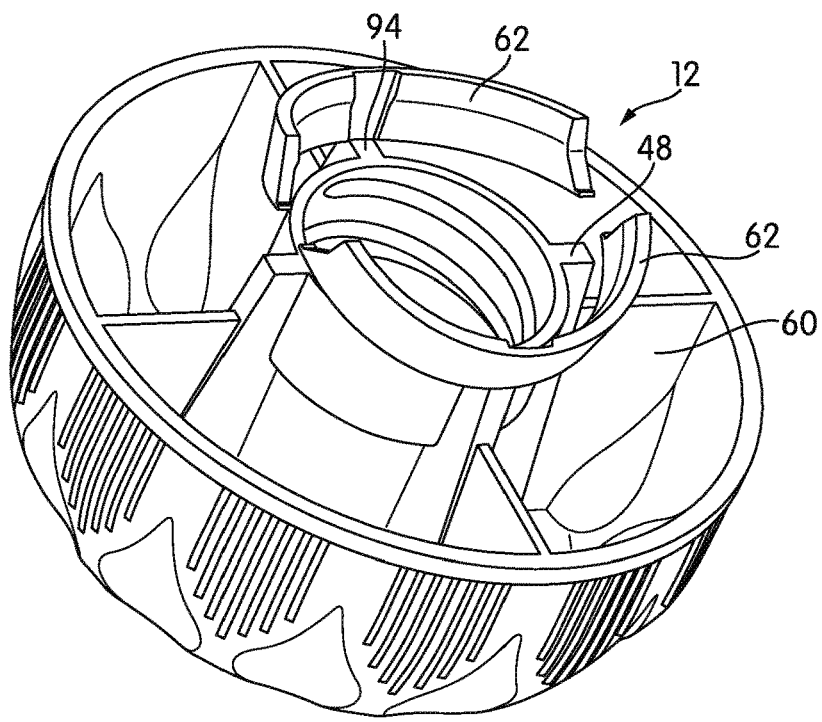
FIG. 32 is a bottom perspective view of the closure of FIG. 23 with the tamper band in an open configuration according to one embodiment.

Referring to FIG. 32, the closure 12 is shown after a user has opened the container assembly 10 and removed the closure 12 from spout 14. The bridges of material 66 over the gaps 64 are broken, separating the safety band 62 into two halves. The two hinge connectors 94 are intact, while the halves of the safety band 62 have been rotated radially outward around the points of connection between the hinge connectors 94 and the safety band 62. The frangible connectors 48 are no longer connected with the safety band 62. The halves of the safety band 62 are rotated upwards and radially outward. The appearance of the safety band 62 is noticeably different and will alert a user to the previous opening of the container assembly 10. In other embodiments, the number of gaps 64 may vary and the safety band 62 may be broken into thirds, quarters, or another number of equal parts.

Figure 33:
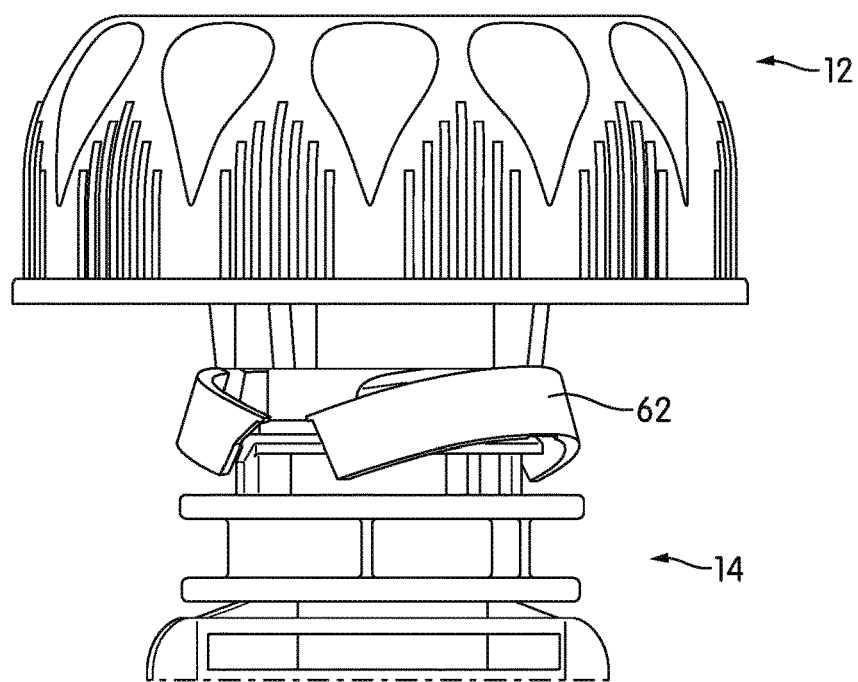
FIG. 33 is a front view of the closure and spout of FIG. 23 with the tamper band in an open configuration according to one embodiment.

Referring to FIG. 33, the closure 12 is shown after a user opened the container assembly 10 and replaced the opened closure 12 back onto the spout 14 of the container assembly 10. Without an intact bridge of material 66, the halves of the safety band 62 angle axially downwards such that the free end of safety band 62 is axially below the position of the hinged connector 94. The lower edges of the central portion of safety band 62 adjacent to the hinge connectors 94 are pushed radially outwards and axially upwards. However, the safety band 62 is still securely connected to the remaining portions of the closure 50 via the connection of hinged connector 94.

Figure 34:
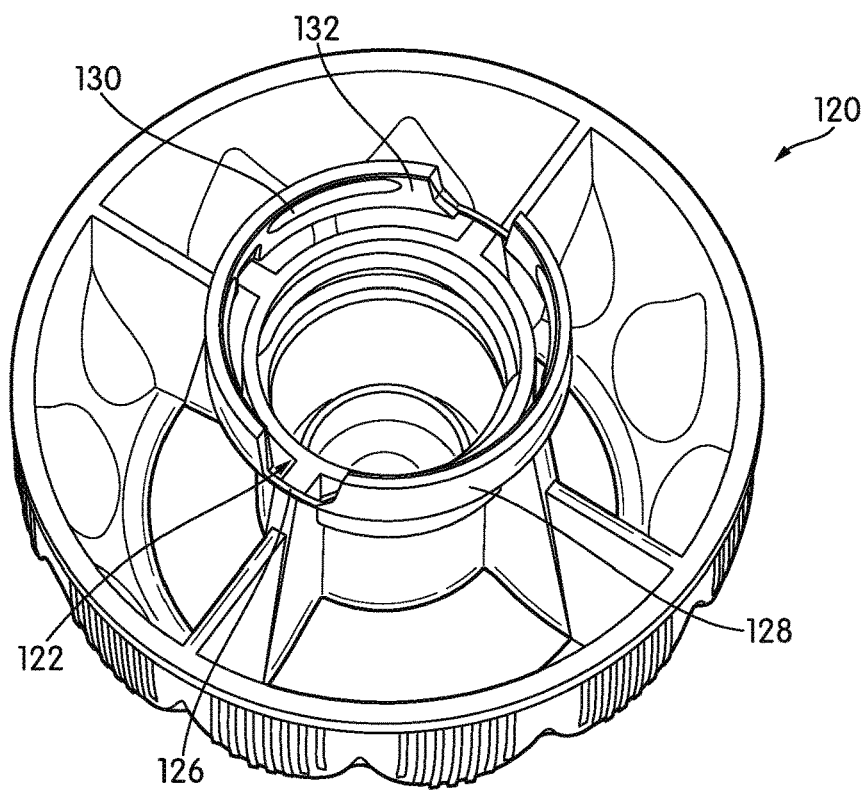
FIG. 34 is a bottom perspective view of a closure according to one embodiment.

Referring to FIG. 34, a closure 120 is shown according another embodiment. Closure 120 is substantially the same as closure 12 except for the differences discussed herein. Closure 120 includes a safety band 128 and a bridge of material 126 over the first gap 122 of the closure 120 that extends for a shorter distance in the radial direction than the bridge of material 66 of the closure 12. That is to say, the bridge of material 126 in the closure 120 is thinner than the bridge of material 66 of the closure 12. The shorter radial distance of the bridge of material 126 may allow bridge of material 126 to break more easily than the bridge of material 66 of safety band 62 of the closure 12.

In addition, closure 120 includes an internal rim 130 of the safety band 128 extending from the radially inward facing surface of safety band 128. The internal rim 130 of the safety band 128 extends around a smaller portion of the circumference of the safety band 128 than the internal rim of the closure 12. As shown the internal rim 130 of the safety band 128 does not extend the entire circumferential distance from the clockwise facing surface to the counterclockwise facing surface of a portion of the safety band 128 of the closure 120. In the embodiment shown, the internal rim 130 of the safety band 128 is not continuous in the circumferential around the inner surface of safety band 128 and includes a gap or space in rim 130 shown at 132.

Figure 35:
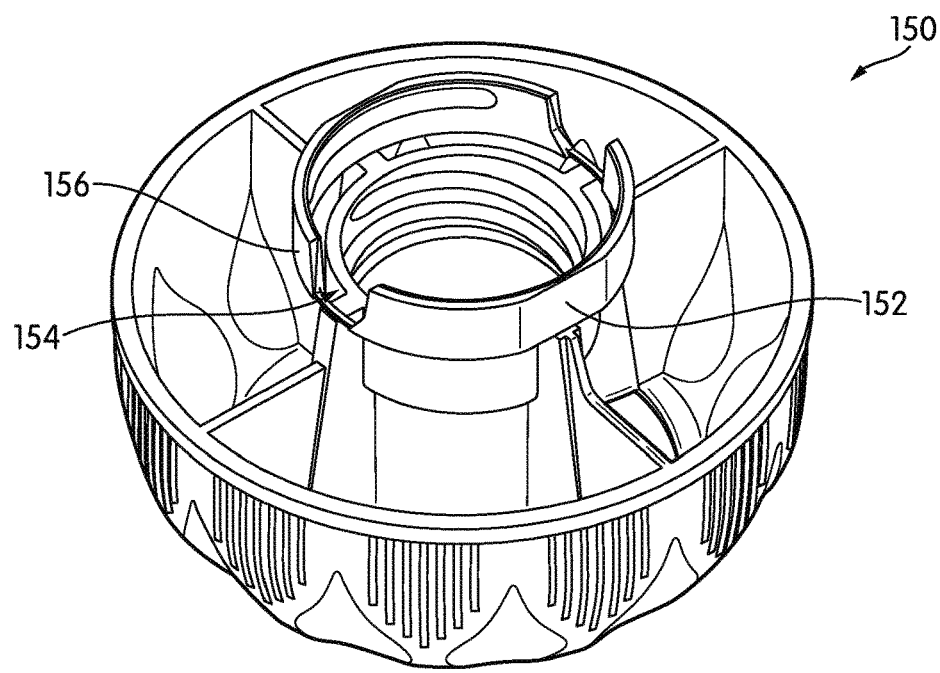
FIG. 35 is a bottom perspective view of a closure according to one embodiment.

Referring to FIG. 35, a closure 150 is shown according to an exemplary embodiment. Closure 150 is substantially the same as closure 12 except for the differences discussed herein. The exterior surface of the safety band 156 is cylindrical for the majority of the circumference of the safety band 156. However, the exterior surface of safety band 156 includes a substantially flat or planar section 152. In some embodiments, the combined circumferential length of the cylindrical portions of safety band 156 is between 240 degrees and 350 degrees of the circumference of the safety band 156 with the remaining circumferential length of safety band resulting from planar sections 152 and gaps 154. In some embodiments, the combined portions of the safety band 156 that are curved stretch around between 270 to 300 degrees of the circumference of the safety band 156.

Figure 36:
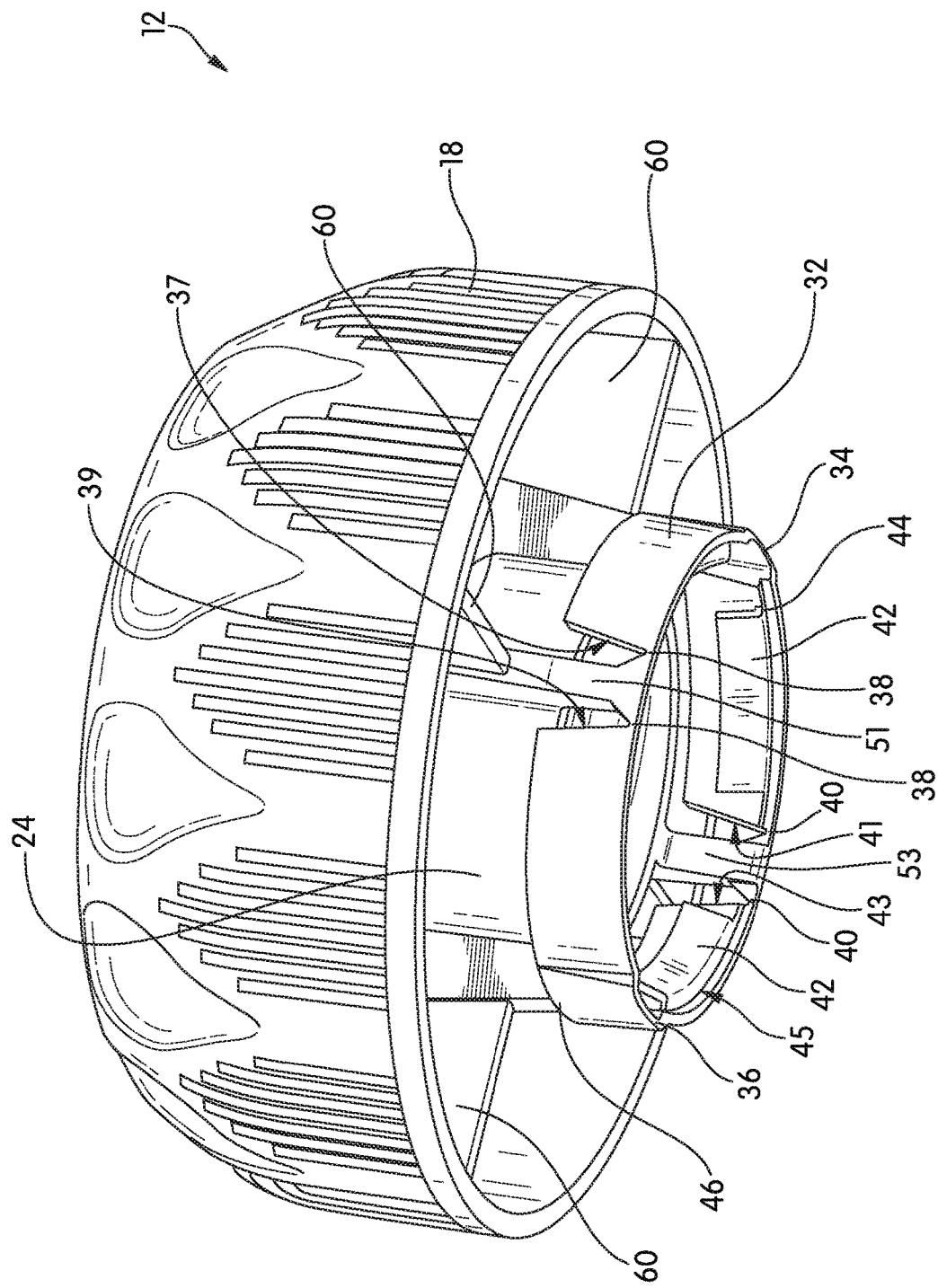
FIG. 36 is perspective view from below of the closure of one embodiment.
Figure 37:
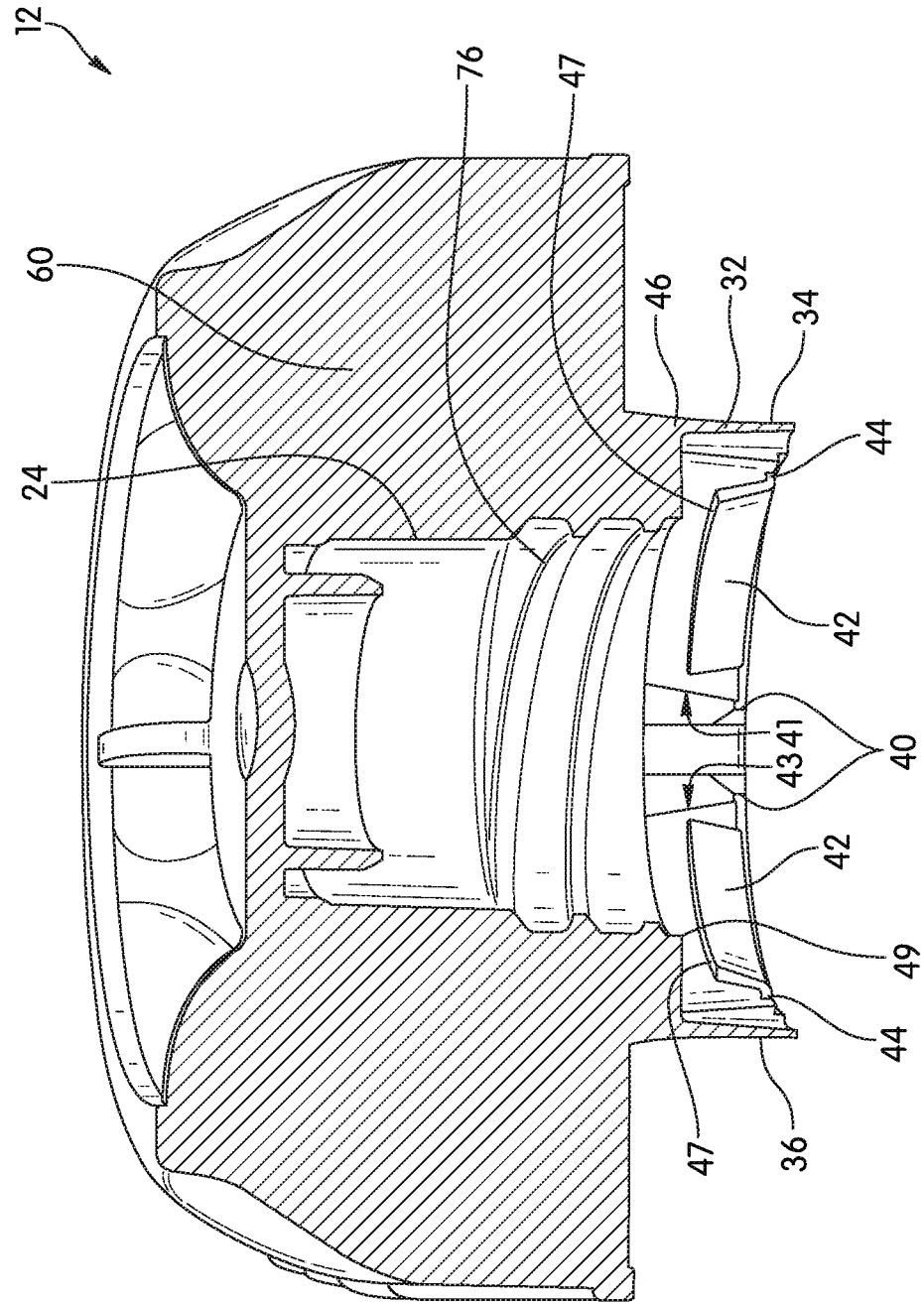
FIG. 37 is a perspective view of a section of the closure of FIG. 36 according to one embodiment.

Referring to FIG. 36 and FIG. 37, closure 12 including a safety band according to another embodiment is shown. As seen in FIG. 36, closure 12 includes a tamper band 32 extending from the lower end of central cylinder 24. Tamper band 32 includes two outer wall sections 34 and 36. A first pair of bridge sections 38 is located between first ends 37 and 39 of tamper band outer wall sections 34 and 36, respectively. A second pair of bridge sections 40 are located between second ends 41 and 43 of tamper band outer wall sections 34 and 36, respectively. Each section 34 and 36 of tamper band 32 includes two engagement structures or walls, shown as J-band sections 42, that extend radially inward away from inner surfaces of outer wall sections 34 and 36 and upward toward the upper end of closure 12.

In various embodiments, outer wall sections 34 and 36 are configured to provide a relatively compete band surrounding the base of central cylinder 24. In various embodiments, outer wall sections 34 and 36 each extend at least 120 degrees around the perimeter of central cylinder 24, specifically at least 150 degrees around the perimeter of central cylinder 24, and more specifically at least 160 degrees around the perimeter of central cylinder 24.

In the embodiment shown, J-band sections 42 are sections that are integrally molded with the rest of tamper band 32 and are connected to the lower end 45 of tamper band 32. In one embodiment, J-band sections 42 are molded in the positioning shown in FIG. 36 with a connector, shown as u-shaped curved connector section 44, molded in the u-shape shown in FIG. 36. In another embodiment, J-band sections 42 are molded extending downward from lower end 45, and following molding, J-band sections 42 are folded upward and inward relative to tamper band 32 forming u-shaped connector section 44. In either molding arrangement, connector section 44 provides the transition from the generally downwardly extending outer wall section 34 or 36 to the generally upwardly extending J-band sections 42.

As shown best in FIG. 37, J-band sections 42 are angled relative to outer wall sections 34 and 36. Further, J-band sections 42 each have an upper edge or surface 47 that defines the upper most surface of each J-band section 42. J-band sections 42 have a height (e.g., the dimension in the direction of the longitudinal axis of the closure) that is less than the heights of outer wall sections 34 and 36. In this arrangement, upper surface 47 is below both the uppermost portions of outer wall sections 34 and 36, and below the lower most edge 49 of central cylinder 24.

As shown in both FIG. 36 and FIG. 37, both outer wall sections 34 and 36 have a length in the circumferential direction that is greater than the length of J-band sections 42 in the circumferential direction. In various embodiments, the linear length of outer wall sections 34 and 36 in the circumferential direction is greater than the linear length of J-band sections 42 in the circumferential direction. In various embodiments, the angular length of outer wall sections 34 and 36 in the circumferential direction is greater than the angular length of J-band sections 42 in the circumferential direction. In specific embodiments, the differential circumferential lengths of outer wall sections 34 and 36 and of J-band sections 42 are the differential lengths between the major, radially inner surfaces of outer wall sections 34 and 36 and the major, radially outer surfaces of J-band sections 42.

FIG. 37 shows approximately one half of closure 12 in cross-section. Accordingly, as shown in FIG. 37, each half section of each of the tamper band outer wall sections 34 and 36 includes one J-band section 42. Thus, in the embodiment of closure 12 shown, tamper band 32 includes a total of four J-band sections 42. However, in other embodiments, tamper band 32 may include various numbers of J-band sections 42, such as 2, 3, 5, 6, etc. J-band sections.

Upon twist-off of closure 12, J-band sections 42 interact with cooperating structures on spout 14 as closure 12 moves upward which causes bridge sections 38 and 40 to break and which also pushes tamper band sections 34 and 36 outward. Tamper band sections 34 and 36 remain connected to the central cylinder 24 by an integrally molded hinge structure 46 (labeled in FIG. 37) that joins each tamper band section 34, 36 to at least one of central cylinder 24 and vertical stabilizers 60. In this manner, tamper band 32 remains coupled to and intact with closure 12 even after opening of closure 12.

As shown best in FIG. 36, tamper band 32 includes two tamper band posts, shown as post sections 51 and 53. Post section 51 is located in the circumferential direction between first ends 37 and 39 of tamper band outer wall sections 34 and 36, and post section 53 is located in the circumferential direction between second ends 41 and 43 of tamper band outer wall sections 34 and 36. In general, post sections 51 and 53 provide a structure that bridges 38 and 40 respectively are coupled to.

In this arrangement, the clockwise and counterclockwise facing surfaces of post sections 51 and 53 and the opposing, clockwise and counterclockwise facing surfaces of the adjacent outer wall sections 34 and 36 define spaces or gaps as shown in FIG. 3. To further provide structure to tamper band 32, each of post sections 51 and 53 are located below one of the vertical stabilizers 60. By providing a relatively robust, rigid and supported anchor point, this positioning of post sections 51 and 53 may facilitate consistent breakage of tamper band 32 at bridges 38 and 40 upon removal of closure 12 because of the relative low level of bend or distortion experienced by post sections 51 and 53 at twist off. In this arrangement, bridge sections 38 and 40 are coupled between opposing clockwise and counterclockwise surfaces of post sections 51 and 53 and of outer wall sections 34 and 36.

Figure 38:
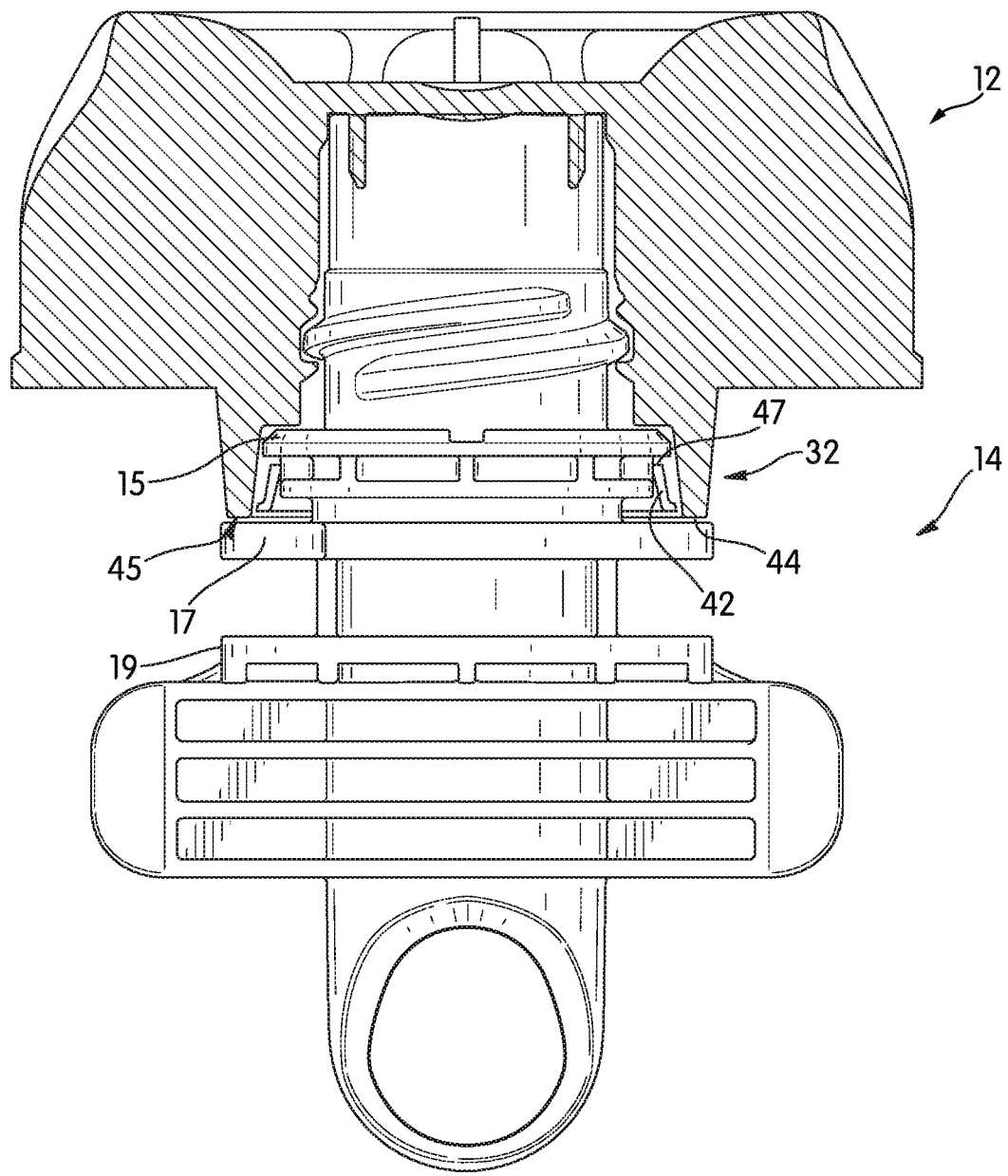
FIG. 38 is a cross-sectional view of the closure of FIG. 36 coupled to a spout according to one embodiment.

Referring to FIG. 38, closure 12 is shown coupled to spout 14. As shown in FIG. 38, when closure 12 is fully engaged on spout 14, J-band sections 42 are engaged underneath upper flange 15. In this arrangement, lower end 45 of tamper band 32 is facing middle flange 17 and there is a small amount of clearance between the lower most surface of tamper band 32 and the upper surface of middle flange 17. Further, J-band sections 42 are positioned such that upper surfaces 47 of each J-band are facing and located beneath upper flange 15.

Figure 39:
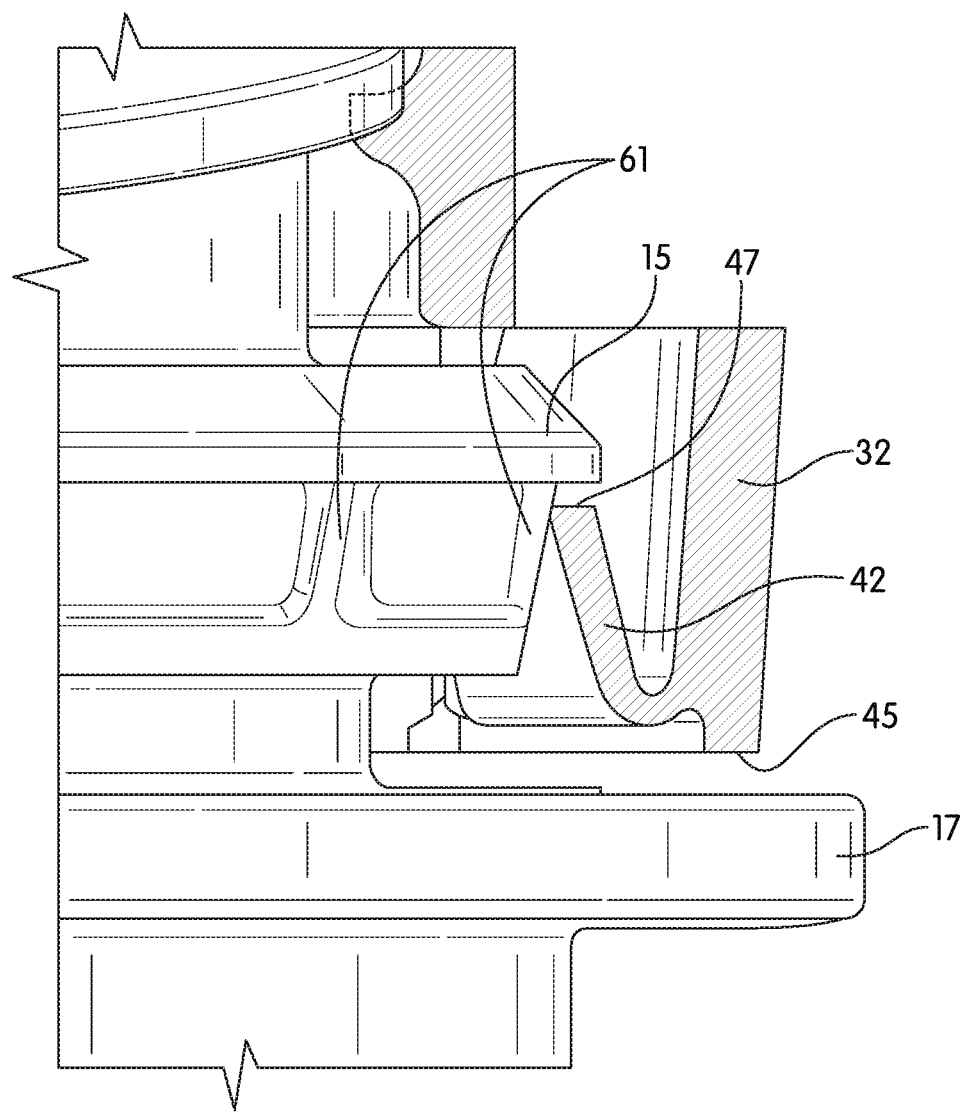
FIG. 39 is a detailed view showing interaction between a spout and a tamper band according to one embodiment.

Referring to FIG. 39, a detailed view of the interaction between J-bands 42 and spout 14 are shown. Spout 14 includes a plurality of generally vertically extending ribs 61 located below upper flange 15. Ribs 61 interact with the radially innermost section of J-band 42 during cap removal limiting the ability of J-bands 42 from tucking under upper flange 15. In this manner, ribs 61 provide a surface that allows J-bands 42 to transition over the outermost edge of upper flange 15 during cap removal.

Figure 40:
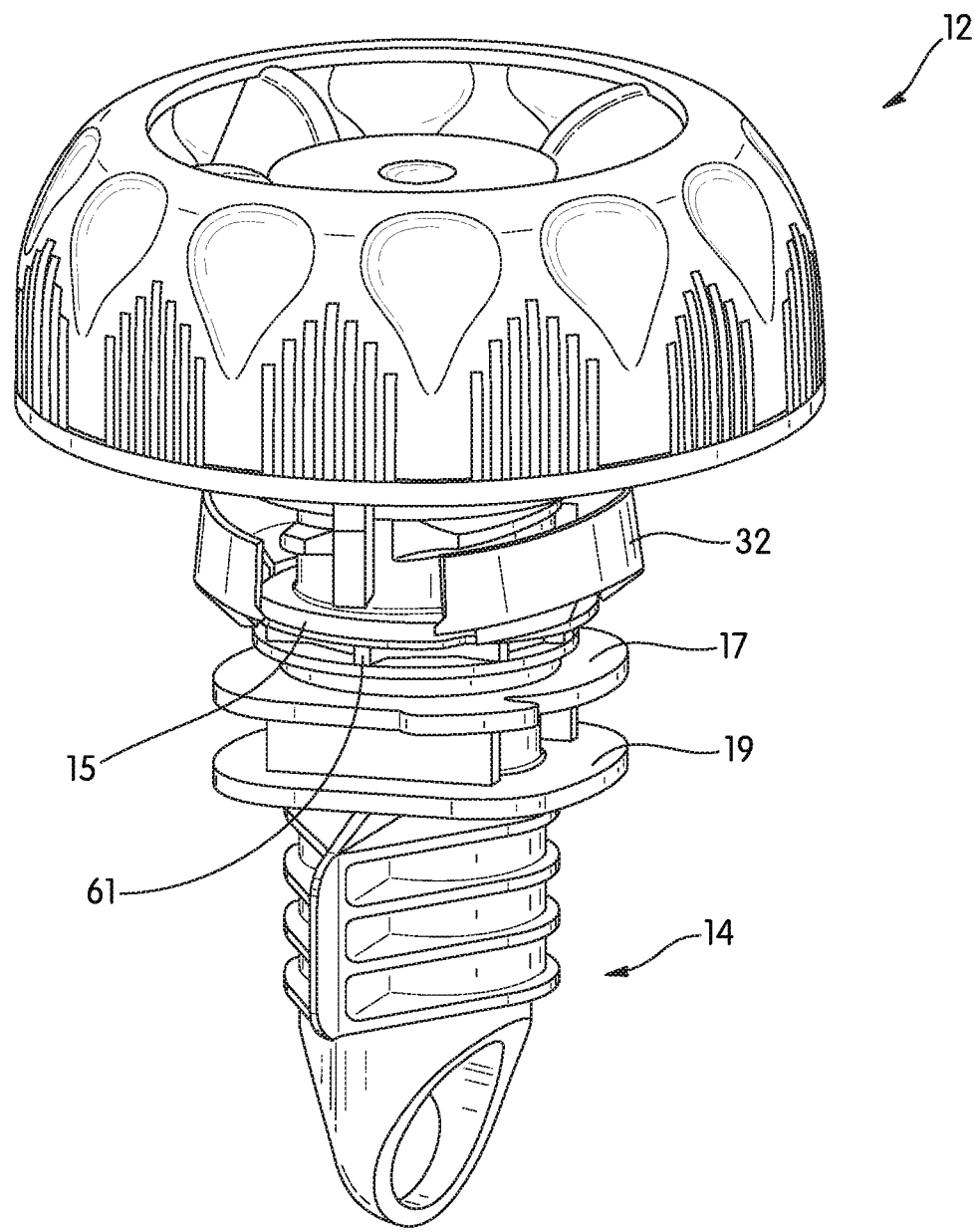
FIG. 40 is a perspective view of container closure assembly of FIG. 36 showing a broken tamper band according to one embodiment.

Referring to FIG. 40, closure 12 is shown during removal from spout 14 according to one embodiment. Upper flange 15 includes an outer surface that acts as a catch ledge. As closure 12 is removed, J-band sections 42 interact with upper flange 15 to push tamper band 32 outward and to break bridges 38 and 40. Specifically, as tamper band 32 passes over upper flange 15 upon removal of closure 12, upper flange 15 acts to spread broken tamper band 32 and pushes broken tamper band 32 radially outward. The broken sections of tamper band 32 pivot radially outward about hinges 46 under the interaction with upper flange 15 further accentuating the appearance of the broken tamper bands. The broken bridge sections 38 and 40 and the outwardly pushed tamper band 32 provides tamper indication by showing that closure 12 has previously been opened, as shown in FIG. 9.

Figure 41:
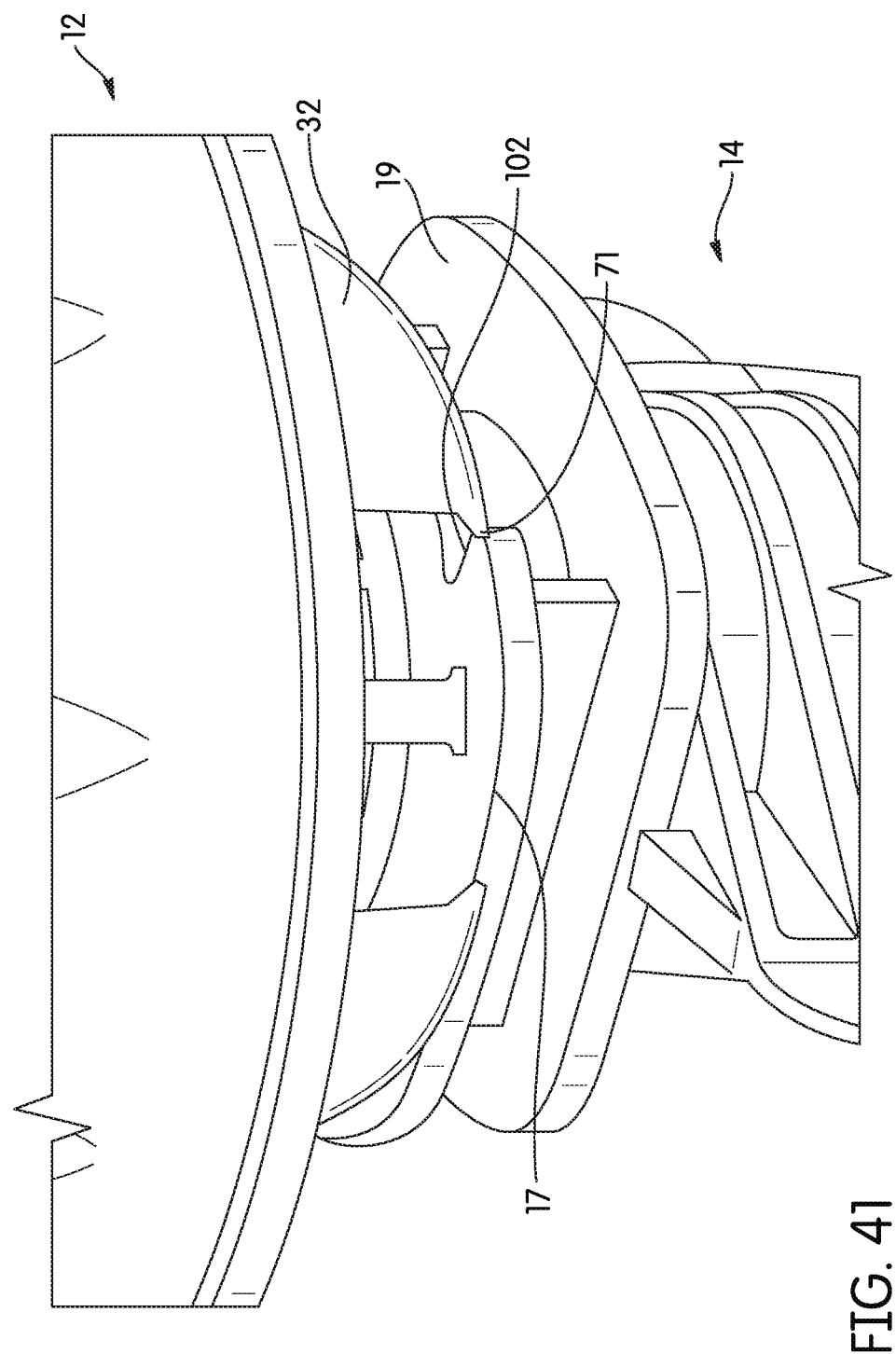
FIG. 41 is a detailed view showing interaction between a spout and a broken tamper band according to one embodiment.

Referring to FIG. 41, a detailed view of the interaction between broken tamper band 32 and spout 14 is shown according to one embodiment. As shown in FIG. 41, middle flange 17 of spout 14 includes a plurality of circumferentially facing surfaces, shown as counterclockwise radial surfaces 102. In the embodiment shown, middle flange 17 includes two counterclockwise radial surfaces 102 spaced about 180 degrees apart around the circumference of middle flange 17. After closure 12 has been first removed from spout 14, tamper band 32 is broken at bridges 38 and 40 forming free ends 71. Upon reapplication of closure 12 following opening, free ends 71 of broken tamper band 32 to engage counterclockwise radial surfaces 102 which acts to maintain tamper band 32 in a position such that it is easy to see that tamper band 32 had previously been broken.

Figure 42:
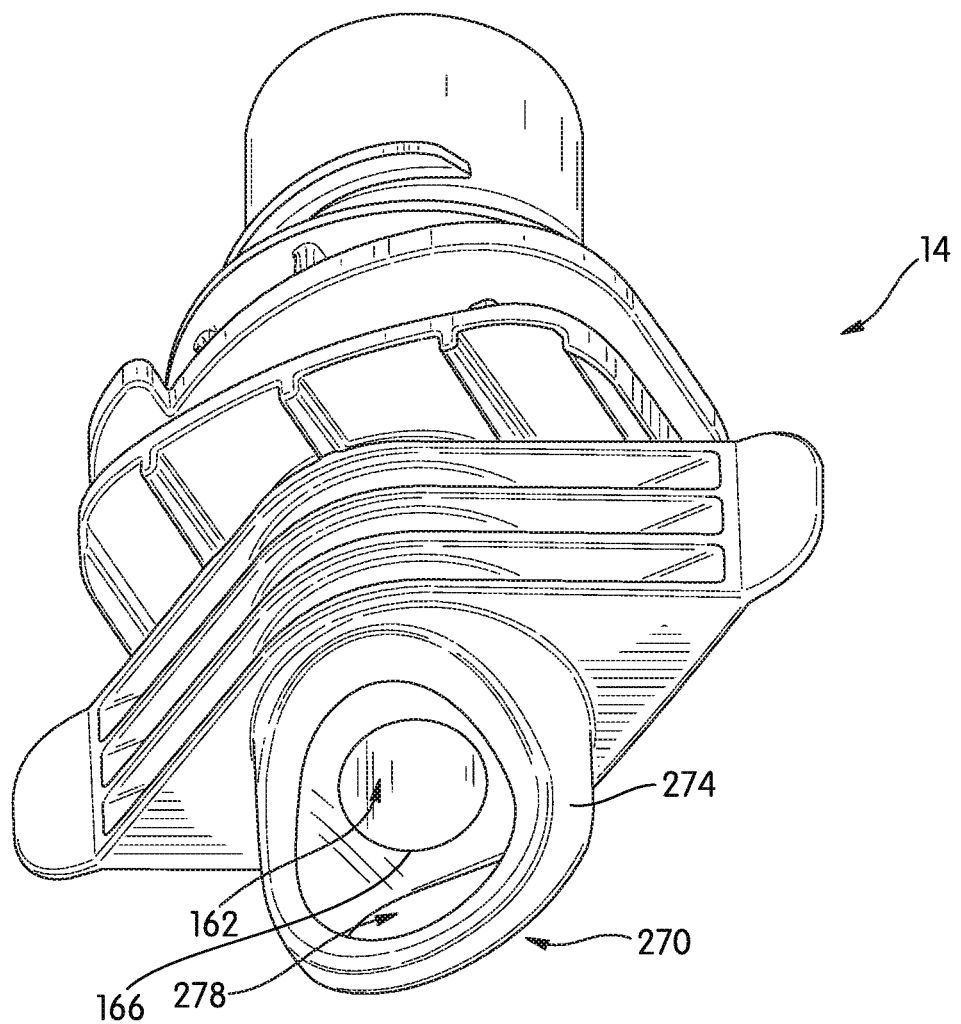
FIG. 42 is a perspective view from below of the spout of FIG. 36 according to one embodiment.
Figure 43:
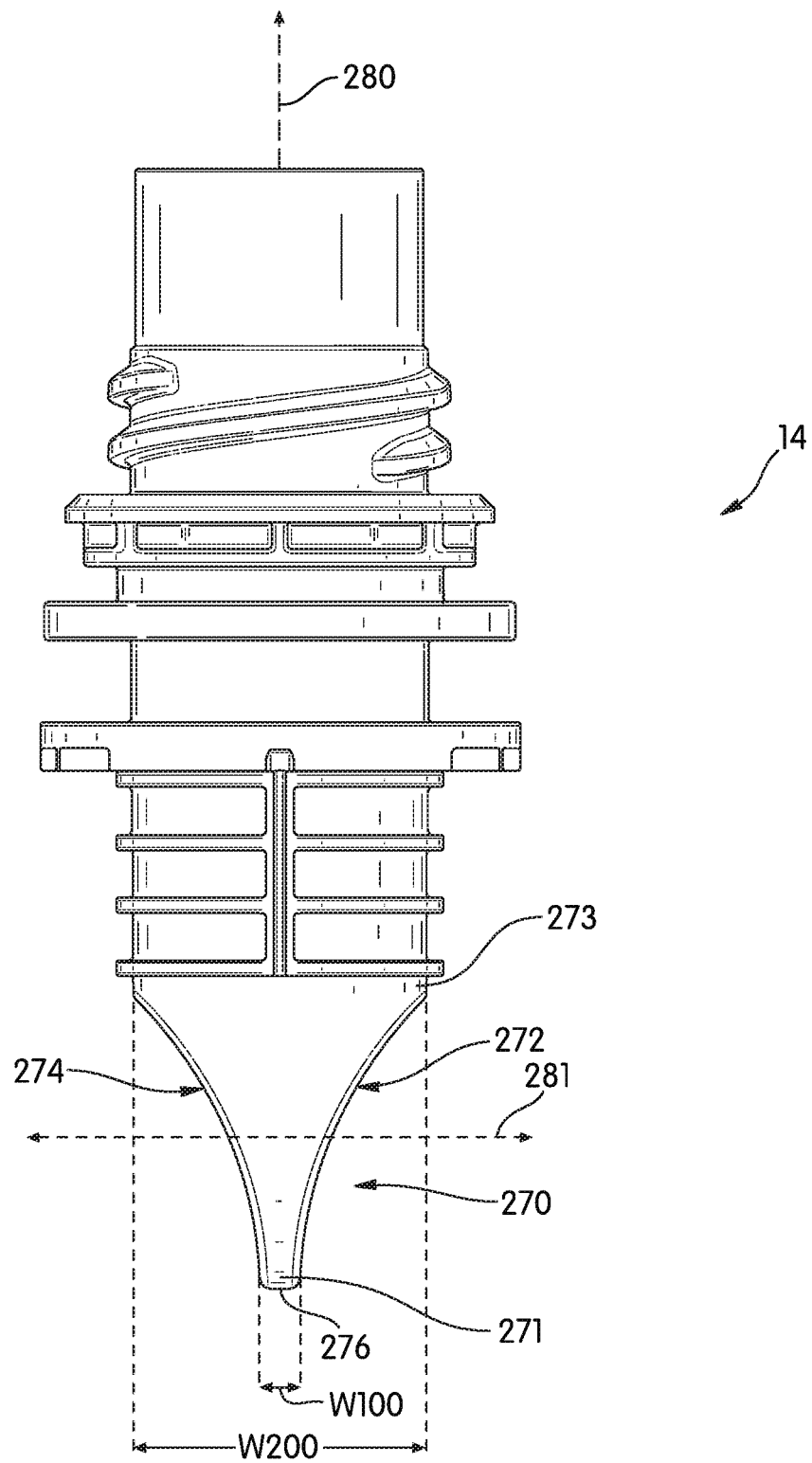
FIG. 43 is a side view of the spout of FIG. 36 according to one embodiment.

Referring to FIG. 42 and FIG. 43, in some embodiments spout 14 includes a structure surrounding the outlet opening 166 of spout 14 that acts to limit occlusion of outlet opening 166 of the spout 14. In the specific embodiment shown, spout 14 includes a structure 270 extending from a lower surface of mounting portion 140 that surrounds outlet opening 166 of spout 14 and acts to limit or prevent outlet opening 166 from being occluded by the sidewall of the container (e.g., pouch 16) to which spout 14 is attached. In general, structure 270 defines a lower channel, shown as ring shaped channel 78, and at least a portion of the entrances to channel 78 lie in a plane substantially parallel to the wings of mounting portion 140.

Referring to FIG. 43, structure 270 includes opposing surfaces 272 and 274 that taper inward toward central axis 280 and that extend downward to bottom surface 276. Channel 278 defines an axis 281 that is substantially perpendicular to both axis 280 and to a plane defined by mounting portion 140. In this arrangement, channel 278 extends between opposing surfaces 272 and 274, and opposing surfaces 272 and 274 are angled inward relative to a plane defined by mounting portion 140. Further, in various embodiments, surfaces 272 and 274 are angled inward toward axis 280.

In various embodiments as shown in FIG. 43, the width, W100, of the tip 271 of structure 270 is relatively small compared to the width, W200, of the upper end 273 of structure 270. In various embodiments, W100 is less than 50% of W200, specifically is less than 30% of W200, and more specifically is less than 20% of W200. In this arrangement, surfaces 272 and 274 generally face the inner surfaces of pouch 16 and provides an elongate ring structure that limits the ability of inner surfaces of pouch 16 to occlude or block outlet opening 166 of spout 14.

To further facilitate the occlusion limiting function of structure 270, surfaces 272 and 274 are curved surfaces that are concave relative to axis 280. In various embodiments, surfaces 272 and 274 are continuously curved surfaces that curve inward toward axis 280. Curved surfaces 272 and 274 may act to provide improved occlusion resistance relative to planar angled walls due to the changing degree of distance between the curved surface 272 and 274 and the inner wall of a container (such as pouch 16).

Figure 44:
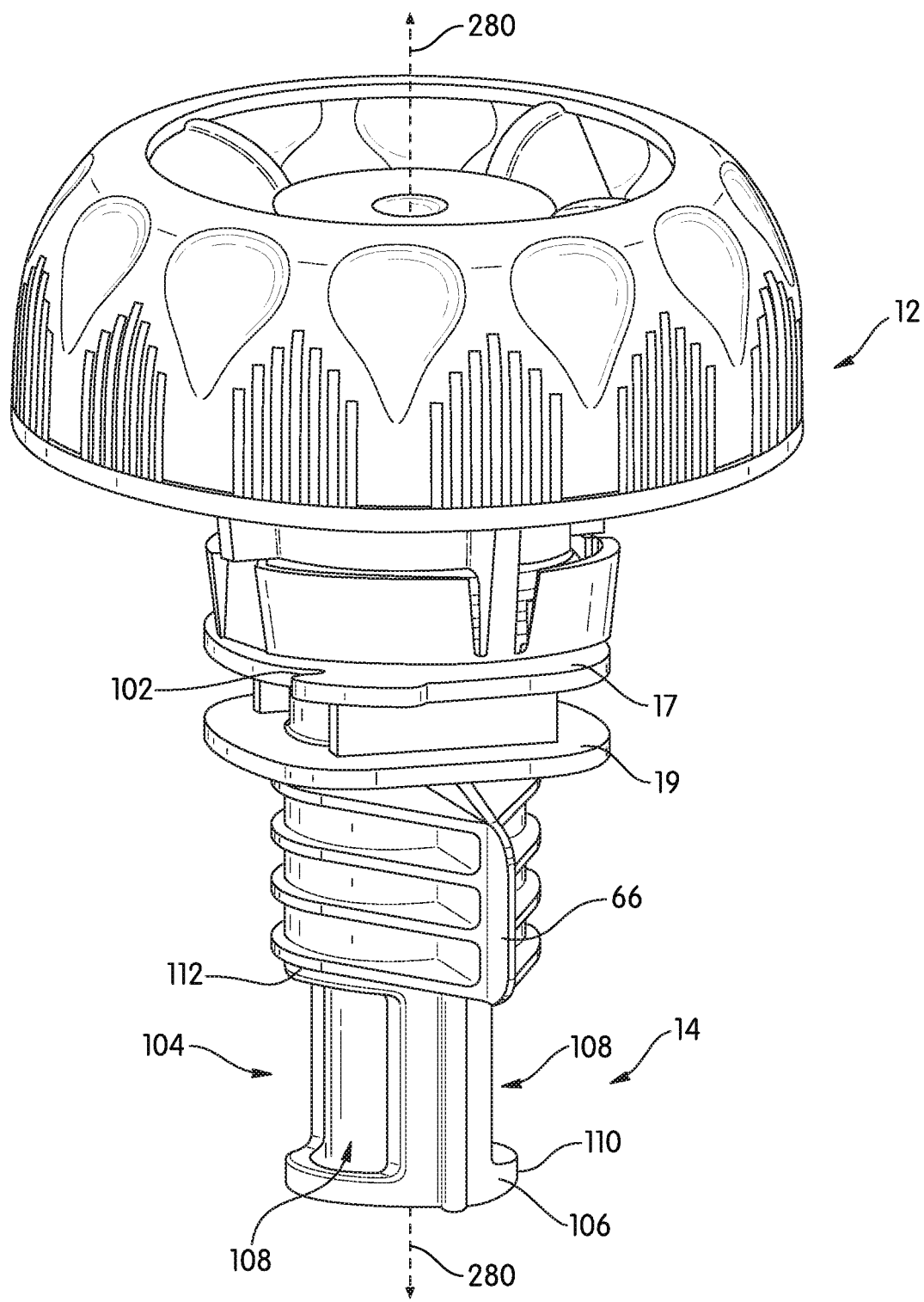
FIG. 44 is a perspective view of container closure assembly including a closure and a spout according to another embodiment.

Referring to FIG. 44, closure 12 is shown coupled to a spout 14 according to another embodiment. Spout 14 is substantially the same as spout 14 except as discussed herein. Spout 14 includes clockwise facing radial surfaces 102 on middle flange 17. Further, spout 14 includes a structure 104 that surrounds outlet opening 166 of spout 14 that acts to limit occlusion of the outlet opening 166. In general, structure 104 includes a lower end flange 106, and at least two generally rectangular, substantially vertical openings 108. Openings 108 are recessed in the direction of axis 280 relative to radial outermost surface 110 of lower end flange 106 and radial surface 112 located below mounting portion 140. In this manner, surfaces 110 and 112 act to space the walls of the container (e.g., pouch 16) from opening 108 such that the walls do not occlude opening 108.

In various embodiments, the closure 12 and/or spout 14 may be formed from a molded plastic material. In various embodiments, closure 12 and/or spout 14 may be polyethylene, polypropylene, polyethylene terephthalate, or any other suitable plastic material. In various embodiments, the closure 12 and/or spout 14 may be formed through any suitable molding method including, injection molding, compression molding, etc. In some embodiments, the entirety of the mounting portion 140 may be monolithically molded.

Referring more specifically to the function of the various embodiments of the vents discussed in detail above, the vents are configured to prevent or limit damage to or degradation of the bonding between the spout 14 and associated pouch 16 during high pressure processing ("HPP") of foods. During an HPP process, such as provided by Avure Technologies, filled containers are placed under pressures of over 80,000 psi using a fluid, such as water. By processing foods at extremely high water pressure (up to 6,000 bar/87,000 psi—more than the deepest ocean), Avure represents that its HPP machines neutralize *listeria, salmonella, E. coli* and other deadly bacteria that may be present in the contents of the containers prior to the HPP process. Unlike thermal, chemical and other high-heat treatments, HPP runs at cold temperatures to reduce altering food taste, texture or quality, or the requirement of adding of chemicals to maintain freshness or to exceed shelf-life.

One challenge with HPP is the development of containers that can be subjected to the pressures that are used during HPP. In the embodiments of the container assembly 10 having a vent as discussed in detail above, the vent allows for high pressures, (such as those used during the HPP process) to be applied to the container assembly without rupturing, degrading, or otherwise damaging the container assembly 10 during the HPP process.

Figure 45:
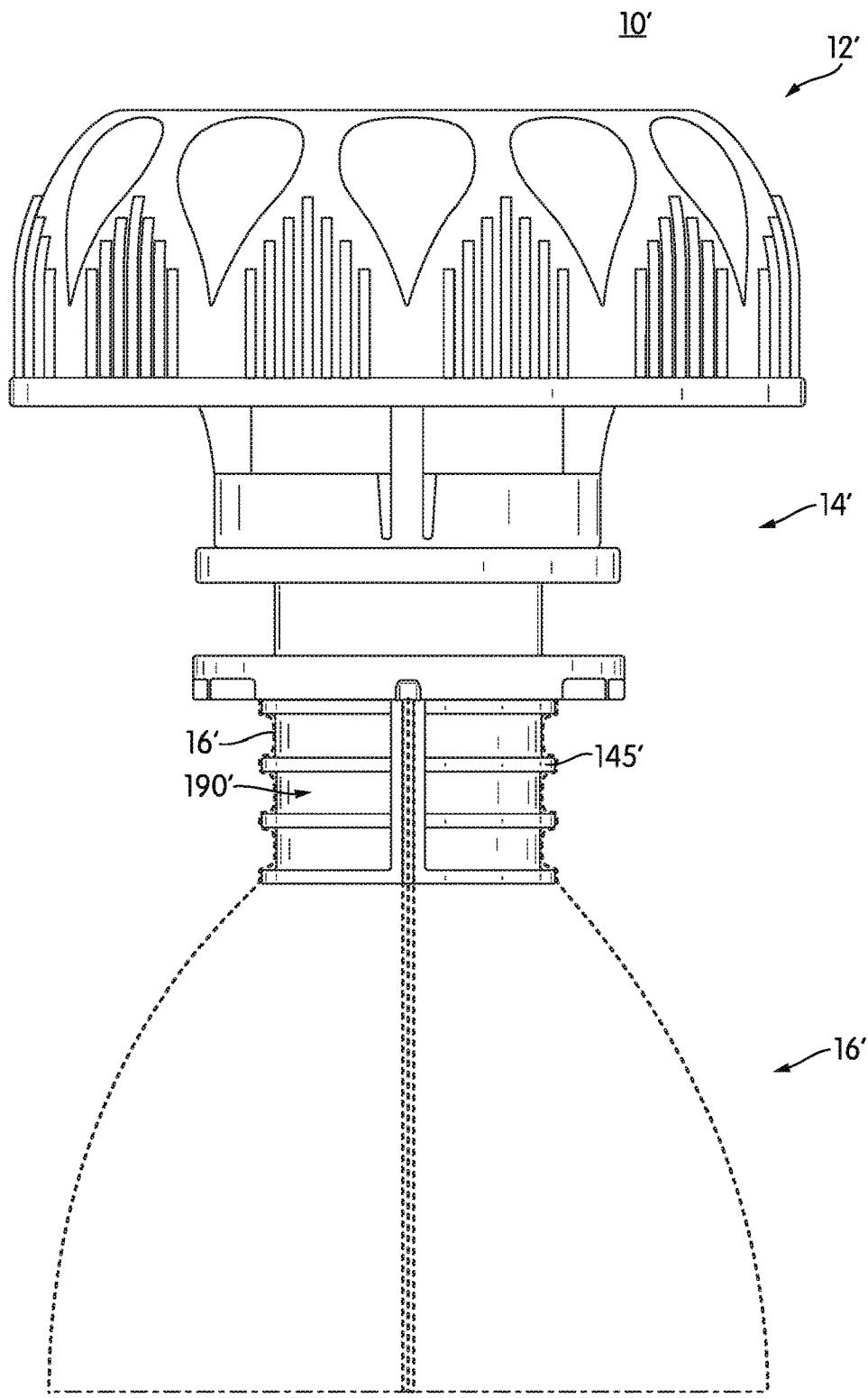
FIG. 45 illustrates a container assembly that does not include a vent structure undergoing high pressure processing.

Referring to FIG. 45, a container assembly 10' which does not include a vent is shown as the container assembly 10' undergoes HPP. During the HPP process, the ambient pressure surrounding the container assembly 10' is increased. However, because the container assembly 10' shown in FIG. 45 is formed without vents, the pressure within any cavities (e.g. spaces 190') formed between the inner surfaces of the sidewalls of the pouch 16' and the exterior surfaces of the mounting portion 140' remains unchanged. As the ambient pressure surrounding the container 10' increases, increasing forces are exerted on the outer surface of the sidewalls of pouch 16'. Because container 10' does not include any vents that allow for fluid communication between the spaces 190' and the outside of the container 10', the pressure inside of spaces 190' and the forces exerted on the inner surfaces of the sidewall of pouch 16' remain unchanged during HPP. Without vents allowing for the pressure within the spaces 190' to equalize to the increasing ambient pressure, as the forces exerted on the outer surface of the pouch 16' continue to increase and the forces acting on the external surfaces of the sidewalls of the pouch 16' become greater than the forces acting on the inner surfaces of the sidewall of the pouch 16', the pouch 16' begins to collapse into and occlude spaces 190', as illustrated in FIG. 45.

As the pouch 16' begins to collapse into and occlude spaces 190' the pouch 16' increasingly impinges on the outer perimeter of ribs 145' and bottom sealing wall 143', resulting in increased stresses on the connection between the pouch 16' and the ribs 145' and causing the original attachment formed between pouch 16' and ribs 145' to deteriorate or otherwise be adversely affected. Also, as the pouch 16' begins to collapse into and occlude spaces 190', the material forming the pouch 190' may begin to deform, also resulting in the deterioration of the original attachment between the pouch 16' and ribs 145'. In some circumstances, as the pouch 16' increasingly is forced into spaces 190', the stress on the pouch material and/or the stress of the increased forces exerted at the attachment between the pouch 16' and ribs 145' may result in the pouch 16' tearing or otherwise rupturing around the interface between the pouch 16' and mounting portion 140'.

Figure 46:
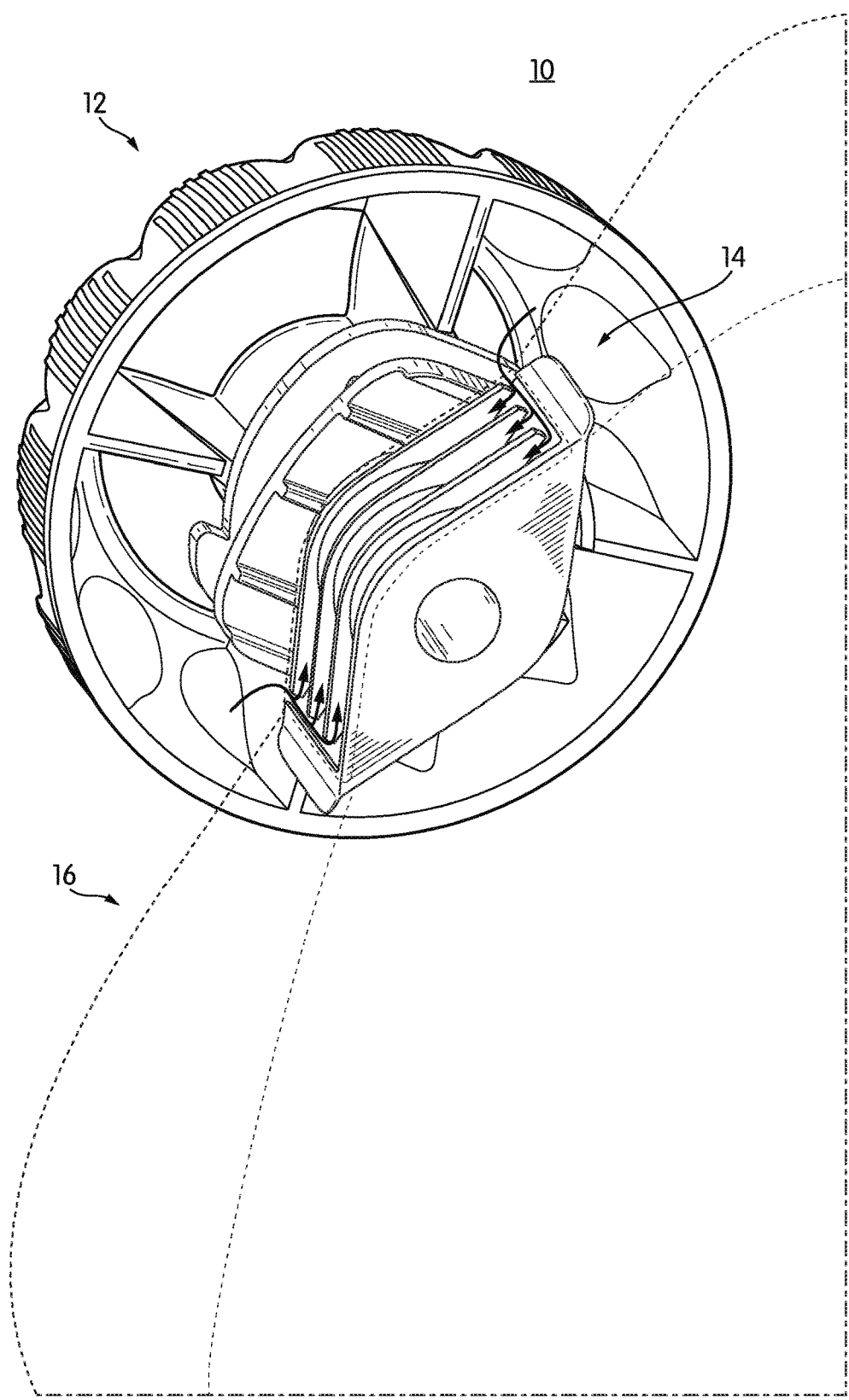
FIG. 46 illustrates a container assembly including a vent structure according to one embodiment undergoing high pressure processing.

Referring to FIG. 46, a container assembly 10 including a vent as discussed in detail above is shown as the container assembly 10 undergoes HPP. As shown by the arrows in FIG. 46, as the ambient pressure surrounding the container assembly 10 increases, vents in the container assembly allows for fluid communication between the outside the container assembly 10 gaps 149 and into spaces 190. By providing for fluid communication between the spaces 190 and the environment surrounding the outside of the container assembly 10, the pressure inside spaces 190 is able to equalize relative to the ambient pressure. Therefore, as the ambient pressure increases during HPP, the pressure inside spaces 190 is also able to correspondingly increase. As a result, the increasing forces acting on the external surface of the sidewalls of the pouch 16 resulting from the increased ambient pressure are counteracted by equal, but opposite forces acting on the internal surface of the sidewalls of the pouch 16 resulting from the corresponding increased pressure inside spaces 190. Because the forces acting on the external surface of the sidewalls of the pouch 16 are counteracted by the forces acting on the internal surfaces of the sidewall of the pouch 16, the changing pressure occurring during HPP prevents the deterioration, deformation, or other impairment of the attachment between the pouch 16 and mounting portion 140.

Although FIG. 46 illustrates a container assembly 10 including a vent structure similar to the vent structure disclosed with reference to the embodiment of FIG. 2 discussed above undergoing HPP, a container assembly 10 including a vent structure according to any of the embodiments discussed above would allow for a similar equalization of internal and ambient pressures during HPP.

Further modifications and alternative embodiments of various aspects of the invention will be apparent to those skilled in the art in view of this description. Accordingly, this description is to be construed as illustrative only. The construction and arrangements, shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

For purposes of this disclosure, the term "attached" means the joining of two components directly or indirectly to one another. Such joining may be stationary or movable in nature. Such joining may be achieved with the two members and any additional intermediate members being integrally formed as a single unitary body with one another or with the two members or the two members and any additional member being attached to one another. Such joining may be permanent in nature or, alternatively, may be removable or releasable in nature.

In various exemplary embodiments, the relative dimensions, including angles, lengths and radii, as shown in the Figures are to scale. Actual measurements of the Figures will disclose relative dimensions, angles and proportions of the various exemplary embodiments. Various exemplary embodiments extend to various ranges around the absolute and relative dimensions, angles and proportions that may be determined from the Figures. Various exemplary embodiments include any combination of one or more relative dimensions or angles that may be determined from the Figures. It should be understood that the figures illustrate the exemplary embodiments in detail, and it should be understood that the present application is not limited to the details or methodology set forth in the description or illustrated in the figures. Further, actual dimensions not expressly set out in this description can be determined by using the ratios of dimensions measured in the Figures in combination with the express dimensions set out in this description. It should also be understood that the terminology is for the purpose of description only and should not be regarded as limiting.

While the current application recites particular combinations of features in the claims appended hereto, various embodiments of the invention relate to any combination of any of the features described herein whether or not such combination is currently claimed, and any such combination of features may be claimed in this or future applications. Any of the features, elements, or components of any of the exemplary embodiments discussed above may be used alone or in combination with any of the features, elements, or components of any of the other embodiments discussed above in the implementation of the teachings of the present disclosure.

What is claimed is:

1. A container comprising:
    a pouch formed from a plastic material to define an interior for containing a substance and an open end into which the substance may be placed from the outside of the pouch;
    a fitment including a fluid-tight wall defining a flow channel through which the substance may flow with respect to the interior of the pouch;
    a sealing formation which is joined to the fitment and sealed to the material at the open end of the pouch with a fluid-tight seal to form a fluid-tight interface between the open end of the pouch and the fitment;
    a support formation which joins the fitment to the open end and supports the fitment relative to the open end such that the fitment, sealing formation, support formation and pouch material form at least one cavity at the interface; and
    a plurality of vents in one of the support formation and the pouch material which forms the cavity, the plurality of vents providing a fluid passage between the cavity and outside of the pouch such that when the pressure of a fluid surrounding the pouch is changed, the plurality of vents permit the fluid to flow relative to the cavity to equalize the pressure within the cavity and at the outside of the pouch.

2. The container of claim 1, wherein the plastic material and the sealing formation are formed from a thermoplastic material and the fluid-tight seal is formed from heated thermoplastic material.

3. The container of claim 1, wherein the fluid-tight seal is formed from an adhesive.

4. The container of claim 1, wherein the plastic material and the support formation are formed from a thermoplastic material and open end and the support formation are joined with a heated thermoplastic material.

5. The container of claim 1, wherein the support formation is joined to the pouch with an adhesive.

6. The container of claim 1, wherein the fluid tight wall extends from the interior of the pouch to a spout located at the outside of the pouch and the wall defines an exterior including treads adapted to receive a closure to produce a fluid-tight seal between the spout and the closure, the fitment, sealing formation and support formation being integrally molded from a thermoplastic material.

7. The container of claim 6, wherein the plastic material is a thermoplastic material and thermoplastic material forms the fluid-tight seal and joins the support formation to the open end.

8. A fitment for a pouch formed from a plastic material to define an interior for containing a substance and an open end into which the substance may be placed from the outside of the pouch, the fitment comprising;
    a wall having an exterior surface and an interior surface defining a flow channel extending between a first opening and a second opening;
    a sealing formation formed on the exterior surface and sealable to the material at the open end of the pouch with a fluid-tight seal to form a fluid-tight interface between the open end of the pouch and the wall;
    a support formation formed on the exterior surface and joinable to the open end to form a cavity between the wall, sealing formation, support formation and pouch material; and
    a plurality of vents in the support formation that provide a fluid passage between the cavity and outside of the pouch such that when the pressure of a fluid surrounding the pouch is changed, the plurality of vents permit the fluid to flow relative to the cavity to equalize the pressure within the cavity and at the outside of the pouch.

9. The fitment of claim 8, wherein the fitment is formed from a thermoplastic material.

10. The fitment of claim 9, wherein the wall is a cylindrical wall including a treaded portion on the exterior surface, proximate the first opening, which is configured to engage the respective threads of a closure.

11. The fitment of claim 10, wherein the cylindrical wall has a longitudinal axis extending between the openings, and the sealing formation is a planar formation laying within a plane perpendicular to the longitudinal axis and having a continuous sealing surface parallel with the longitudinal axis.

12. The fitment of claim 11, wherein the support formation lays within a plane perpendicular to the longitudinal axis and has a continuous support surface parallel with the longitudinal axis.

13. The fitment of claim 12, wherein the sealing and support formations have the same shape.

14. The fitment of claim 13, wherein the sealing and support formations have a rhombus-type shape with rounded vertices.

15. A method for sterilizing the contents of a container assembly, the method comprising:
  providing a container assembly including a pouch, a spout, and a closure, wherein the spout includes:
    a flow channel through which the contents may flow from the interior of the pouch to a location outside the pouch;
    a bottom sealing wall surrounding the flow channel, the outer perimeter of the bottom wall configured for forming a fluid-tight interface with the inner surface of the sidewall of the pouch when the pouch and spout are sealed, the contents of the pouch only being accessible to a location outside the pouch through the flow channel when the pouch and spout are sealed together; and
    one or more ribs extending radially outwardly from the flow channel and located above the bottom sealing wall;
  sealing the spout to the pouch to form a fluid-tight interface, wherein when the pouch and spout are sealed together, one or more cavities are formed, each cavity being bounded in its entirety by the inner surface of the sidewall of the pouch and the outer surface of the spout;
  providing a plurality of vents, in one of the spout and the pouch, that provide fluid communication between the one or more cavities and the outside of the pouch; and
  sterilizing the contents of the container assembly after the spout, pouch and closure have been assembled.

16. The method of claim 15, wherein the volume of each cavity remains substantially constant during the sterilization process.

17. The method of claim 15, wherein the internal pressure within each cavity is substantially the same as the ambient pressure surrounding the container during the sterilization process.

18. The method of claim 17, wherein the sterilization process is a high pressure processing (HPP) process.

19. The method of claim 18, wherein more than 50,000 psi of pressure are applied to the container assembly during the HPP sterilization process.

20. The method of claim 15, wherein the pouch and spout are each formed of a thermoplastic material.

* * * * *